(12) United States Patent
Tavakoli et al.

(10) Patent No.: US 12,097,174 B2
(45) Date of Patent: *Sep. 24, 2024

(54) METHODS AND AGENTS THAT ENHANCE MYOGENIC PROGENITOR CELL ENGRAFTMENT

(71) Applicants: President and Fellows of Harvard College, Cambridge, MA (US); The Children's Medical Center Corporation, Boston, MA (US)

(72) Inventors: Sahar Tavakoli, Cambridge, MA (US); Amy J. Wagers, Cambridge, MA (US); Leonard Zon, Brookline, MA (US)

(73) Assignees: President and Fellows of Harvard College, Cambridge, MA (US); The Children's Medical Center Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/088,756

(22) Filed: Dec. 26, 2022

(65) Prior Publication Data

US 2023/0277487 A1    Sep. 7, 2023

Related U.S. Application Data

(63) Continuation of application No. 16/931,374, filed on Jul. 16, 2020, now Pat. No. 11,534,418, which is a continuation-in-part of application No. PCT/US2019/013879, filed on Jan. 16, 2019.

(60) Provisional application No. 62/618,055, filed on Jan. 16, 2018.

(51) Int. Cl.
*A61K 31/196* (2006.01)
*A61K 31/341* (2006.01)
*A61K 31/44* (2006.01)
*A61K 31/661* (2006.01)
*A61P 21/00* (2006.01)
*C12N 5/077* (2010.01)
*G01N 33/50* (2006.01)

(52) U.S. Cl.
CPC .......... *A61K 31/196* (2013.01); *A61K 31/341* (2013.01); *A61K 31/44* (2013.01); *A61K 31/661* (2013.01); *A61P 21/00* (2018.01); *C12N 5/0652* (2013.01); *G01N 33/5061* (2013.01); *C12N 2501/999* (2013.01)

(58) Field of Classification Search
CPC ..... A61P 21/00; A61K 31/196; A61K 31/341; A61K 31/44; A61K 31/661; A61K 35/34
See application file for complete search history.

(56) References Cited

U.S. PATENT DOCUMENTS 11,534,418 B2    12/2022  Tavakoli et al.
2017/0232074 A1   8/2017  Mooney et al.

OTHER PUBLICATIONS

International Search Report from PCT/US1029/013879, dated May 23, 2019.
Liantonio, et al., "Niflumic Acid Inhibits Chloride Conductance of Rat Skeletal Muscle by Directly Inhibiting the CLC-1 Channel and by Increasing Intraceullalar Calcium," British Journal of Pharmacology, 150:235-247, (2007).
Non-Final Office Action for U.S. Appl. No. 16/931,374, dated Jan. 12, 2022.
Notice of Allowance for U.S. Appl. No. 16/931,374, dated Aug. 26, 2022.

*Primary Examiner* — Umamaheswari Ramachandran
(74) *Attorney, Agent, or Firm* — Morse, Barnes-Brown & Pendleton, P.C.; Lisa M. Warren, Esq.

(57) ABSTRACT

Disclosed herein are agents that enhance muscle stem cell engraftment, as well as methods and compositions using the same.

3 Claims, 32 Drawing Sheets

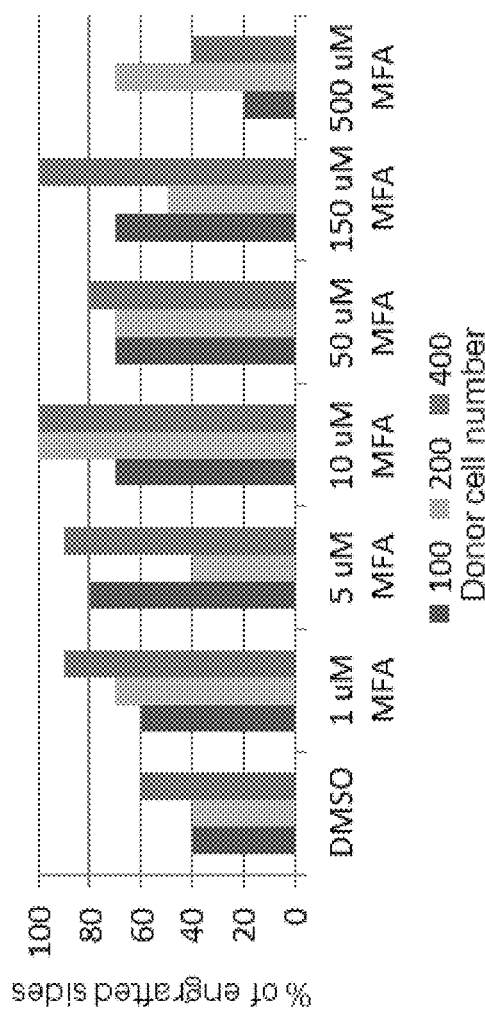
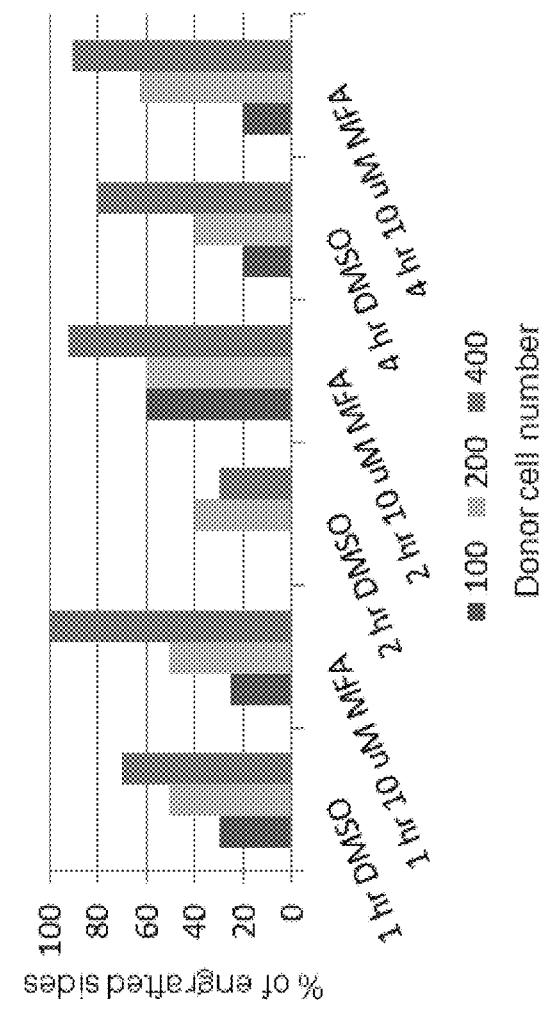
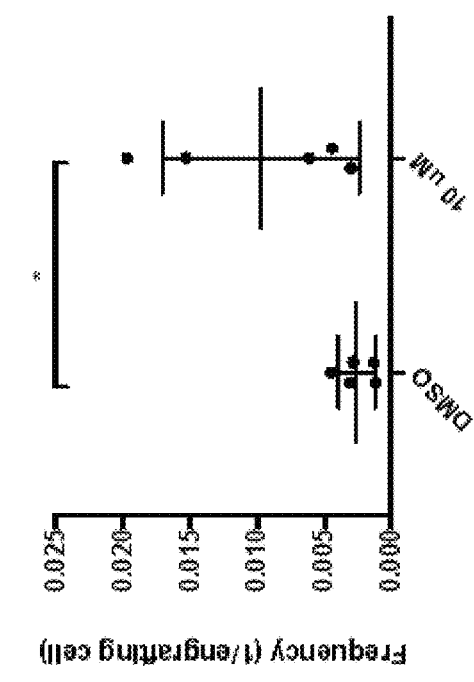
FIG. 4A Estimated engrafting cell frequency
FIG. 4B
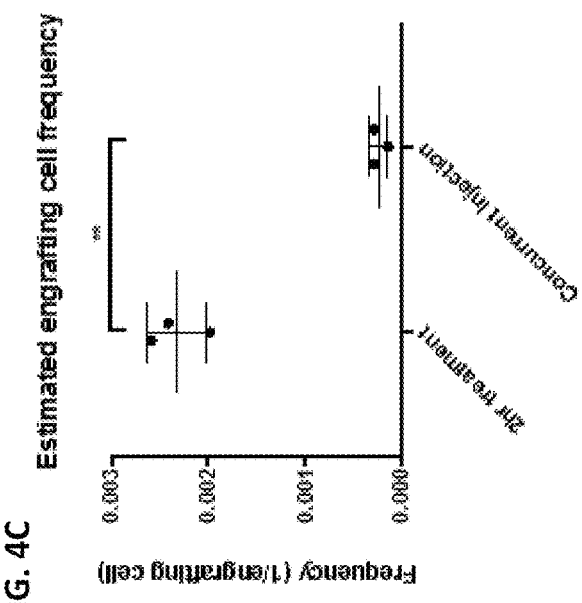
FIG. 4C Estimated engrafting cell frequency

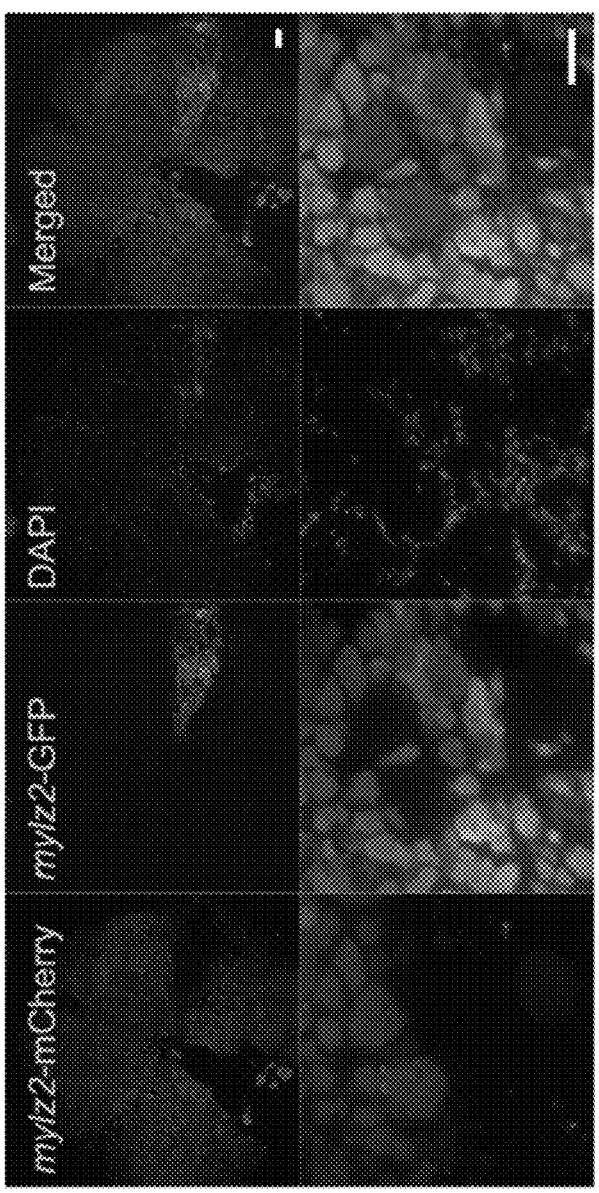
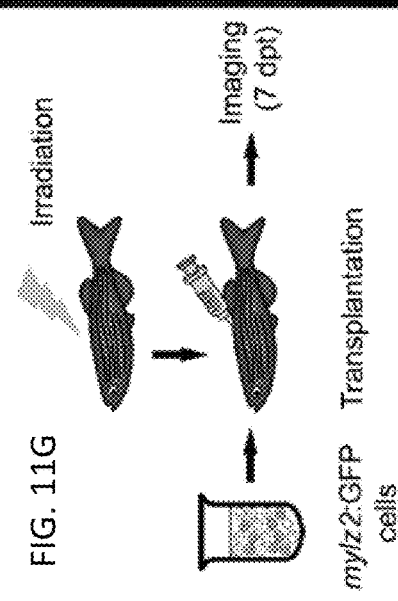
FIG. 11H
FIG. 11G

METHODS AND AGENTS THAT ENHANCE MYOGENIC PROGENITOR CELL ENGRAFTMENT

CROSS-REFERENCE TO RELATED APPLICATIONS

This application is a continuation of U.S. application Ser. No. 16/931,374, filed Jul. 16, 2020 (now U.S. Pat. No. 11,534,418), which is a continuation-in-part application of International Application No. PCT/US2019/013879, filed Jan. 16, 2019, which claims the benefit of U.S. Provisional Application No. 62/618,055, filed on Jan. 16, 2018. The entire teachings of these applications are incorporated herein by reference.

BACKGROUND OF THE INVENTION

Skeletal muscle is a highly specialized, post-mitotic tissue that must withstand chronic mechanical and physiological stress throughout life to maintain proper contractile function. The basic structural unit of skeletal muscle is the myofiber, a multinucleated and post-mitotic cell. Because myofibers are multinucleated and structurally complex, they cannot replace themselves during tissue repair through traditional cell division. Instead, myofiber repair is contingent upon the successful fusion of mononucleated muscle progenitors, called myoblasts, into de novo or residual injured or atrophied fibers.

Myoblasts are primarily generated from resident muscle stem cells, called "satellite cells," which are Pax7+/MyoD−/Myf5− mononuclear, unipotent stem cells. Satellite cells localize beneath the basal lamina of muscle fibers and generally remain mitotically quiescent in intact (uninjured) adult muscle. Satellite cells undergo activation upon muscle damage, initiating both self-renewing and differentiating divisions and producing daughter myoblasts that fuse together to build, and re-build, new muscle. Chronic muscle damage, caused by repeated injury or genetic disorders like muscular dystrophies, may deplete satellite cells and impair their function, leading to a diminished regenerative response, progressive loss of muscle mass, and reduction of strength and mobility. Transplantation-based studies in animal models have demonstrated the utility of engrafted satellite cells for regenerating diseased muscle. However, challenges in obtaining adequate numbers of satellite cells from adult skeletal muscle, in expanding these cells ex vivo or generating them from pluripotent stem cell sources, and in achieving sufficient efficiencies for engraftment of the transplanted cells, have presented significant barriers to the clinical application of such transplantation approaches.

Muscle damage or disease leads to progressive weakness and disability, and manifests in more than 100 different human disorders, including Duchenne Muscular Dystrophy (DMD), one of the most common X-linked disorders in humans. Current treatment options for muscular dystrophies are disappointingly limited and focus mainly on managing symptoms and suppressing the immune and inflammatory response. Because many dystrophies arise from inherited mutations in genes necessary for maintaining proper myofiber structure, repair potential, or contractile function, therapeutic approaches that seek to cure these disorders must include a strategy to repair or replace the mutated gene. Unfortunately, such approaches have been severely challenged by limitations imposed by the low engraftment capacity of cultured myoblasts and difficulties in engraftment measurement in vivo. Although clinical trials of myoblast transplantation into DMD patients started in the 1970s, there has been a lack of effective myoblast engraftments until the present.

SUMMARY OF THE INVENTION

Utilizing a high-throughput screening method in zebrafish, a number of agents have been identified that enhance engraftment of myogenic progenitor cells into muscle tissue, enabling more effective treatment of muscle damage and diseases, such as Duchenne Muscular Dystrophy, via myogenic progenitor cell transplant.

Some aspects of the disclosure are directed to a method of increasing the engraftment efficiency of myogenic progenitor cells (e.g., muscle stem cells, skeletal muscle progenitors, myoblasts) comprising contacting the myogenic progenitor cells with one or more agents that increase the engraftment efficiency of the myogenic progenitor cells into a subject.

In some embodiments, the agent comprises a compound that increases intracellular $Ca^{2+}$ levels in myogenic progenitor cells. In some embodiments, the compound that increases intracellular $Ca^{2+}$ levels in myogenic progenitor cells (MPCs) increases influx of extracellular $Ca^{2+}$ and/or promotes release of mitochondrial $Ca^{2+}$ stores. In some embodiments, the agent is a lipid or membrane permeable calcium ionophore (e.g., Ionomycin). In some embodiments, the agent activates a G-protein-coupled receptor on MPCs. In some embodiments, the agent is meclofenamic acid (MFA), lysophosphatidic acid (LPA), or niflumic acid (NFA). In some embodiments, the MPCs are contacted with both LPA and NFA.

In some embodiments, the myogenic progenitor cells are contacted with the one or more agents prior to transplant of the myogenic progenitor cells into a subject. In some embodiments, the myogenic progenitor cells are contacted with the one or more agents at least one hour prior to transplant of the myogenic progenitor cells into the subject. In some embodiments, the MPCs to be transplanted are from, e.g., cultured from, the same subject (autologous) or are from a different individual (allogenic). In some embodiments, the MPCs to be transplanted are obtained from induced pluripotent stem cells derived from the subject's cells or from the cells of another. In some embodiments, the MPCs to be transplanted have been genetically modified or are derived from cells that are genetically modified. In some embodiments, the genetic modification(s) corrects a defect associated with or causing a muscle condition or disease (e.g., DMD).

In some embodiments, the myogenic progenitor cells are contacted with the agent in vivo. In some embodiments, the MPCs are endogenous to the subject. In some embodiments, the MPCs are administered to the subject prior to administration of the agent or agents; in other embodiments the MPCs are administered to the subject concurrently with or after administration of the agent or agents. In some embodiments, the in vivo MPCs were previously cultured from the subject's cells or from the cells of another and administered to the subject. In some embodiments, the in vivo MPCs were obtained from induced pluripotent stem cells derived from the subject's cells or from the cells of another. In some embodiments, the in vivo MPCs have been genetically modified or are derived from cells that are genetically modified. In some embodiments, the genetic modification corrects a defect associated with or causing a muscle condition or disease (e.g., DMD). In some embodiments, the subject was treated to correct a genetic defect in vivo or ex vivo. In some embodiments, the subject was treated to increase endogenous MPC levels.

In some embodiments, the subject is a human or a zebrafish.

Some aspects of the disclosure are directed to a method of enhancing tissue culture of muscle tissue, comprising adding one or more agents that increase the engraftment efficiency of myogenic progenitor cells into the muscle tissue. In some embodiments, the agent is selected from a compound that increases intracellular $Ca^{2+}$ levels in myogenic progenitor cells (e.g., a membrane permeable calcium ionophore), lonomycin, meclofenamic acid (MFA), lysophosphatidic acid (LPA), and niflumic acid (NFA). In some embodiments, the tissue culture comprises zebrafish cells or mammalian, e.g., human cells.

Some aspects of the disclosure are directed to a method of screening for a test agent that enhances engraftment of myogenic progenitor cells comprising contacting the test agent with a population of myogenic progenitor cells, adding the contacted myogenic progenitor cells to a muscle tissue, and comparing engraftment into the muscle tissue of the contacted myogenic cells to engraftment into the muscle tissue of control myogenic progenitor cells not contacted with the test agent, thereby determining whether the test agent enhances engraftment. In some embodiments, at least one of the myogenic progenitor cells and the muscle tissue comprises a label (e.g., a fluorescent label). In some embodiments, the myogenic progenitor cells and the muscle cells are zebrafish cells, mouse cells, or human cells.

Some aspects of the disclosure are directed to a method of screening for a test agent that enhances engraftment of myogenic progenitor cells comprising contacting the test agent with a population of myogenic progenitor cells and measuring changes in gene expression as compared to a control (e.g., gene expression in uncontacted myogenic progenitor cells). In some embodiments, the test agent is identified as an enhancer of engraftment of myogenic progenitor cells if contact with the agent increases the expression of calcium dependent genes (e.g., one or more of the calcium dependent genes provided in FIG. 21) and/or decreases the expression of muscle development genes (e.g., one or more of the muscle development genes provided in FIG. 21).

Some aspects of the disclosure are directed to a composition comprising myogenic progenitor cells and one or more agents that enhance engraftment of the myogenic progenitor cells into muscle tissue.

In some embodiments, the agent comprises a compound that increases intracellular $Ca^{2+}$ levels in myogenic progenitor cells. In some embodiments, the compound that increases intracellular $Ca^{2+}$ levels in myogenic progenitor cells (MPCs) increases influx of extracellular $Ca^{2+}$ and/or promotes release of mitochondrial $Ca^{2+}$ stores (e.g., membrane permeable calcium ionophore, lonomycin). In some embodiments, the agent is a lipid (e.g., a bioactive lipid). In some embodiments, the agent activates a G-protein-coupled receptor on MPCs. In some embodiments, the agent is lonomycin, meclofenamic acid (MFA), lysophosphatidic acid (LPA), or niflumic acid (NFA). In some embodiments, the composition comprises both LPA and NFA as agents.

In some embodiments, the one or more agents comprise NFA at a concentration of about 0.1 to 150 uM. In some embodiments, the one or more agents comprise LPA at a concentration of about 0.1-10 uM LPA. In some embodiments, the one or more agents comprise MFA at a concentration of about 1-50 uM MPA. In some embodiments, the myogenic progenitor cells are human myogenic progenitor cells.

Some aspects of the disclosure are directed to a composition comprising one or more (e.g., two or more) agents (e.g., a therapeutically effective amount of one or more agents) that increase the engraftment efficiency of myogenic progenitor cells into muscle tissue of a subject and a pharmaceutically acceptable diluent or excipient. In some embodiments, the agent is selected from a compound that increases intracellular $Ca^{2+}$ levels in myogenic progenitor cells, lonomycin, meclofenamic acid (MFA), lysophosphatidic acid (LPA), and niflumic acid (NFA). In some embodiments, the composition comprises at least two, at least three, at least four, or more agents. In some embodiments, the composition comprises at least two agents selected from meclofenamic acid (MFA), lysophosphatidic acid (LPA), lonomycin, and niflumic acid (NFA). In some embodiments, the composition comprises, consists essentially of, or consists of LPA, NFA, and one or more pharmaceutically acceptable diluents and/or excipients.

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), *Current Protocols in Molecular Biology, Current Protocols in Immunology, Current Protocols in Protein Science*, and *Current Protocols in Cell Biology*, all John Wiley & Sons, N.Y., edition as of December 2008; Sambrook, Russell, and Sambrook, *Molecular Cloning: A Laboratory Manual*, $3^{rd}$ ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, NJ, 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange; $10^{th}$ ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, MD) and National Center for Biotechnology Information, National Library of Medicine (Bethesda, MD), as of May 1, 2010, available on the World Wide Web at ncbi.nlm.nih.gov/omim/ and in Online Mendelian Inheritance in Animals (OMIA), a database of genes, inherited disorders and traits in animal species (other than human and mouse), at omia.angis.org.au/contact.shtml.

All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

The above discussed, and many other features and attendant advantages of the present inventions will become better understood by reference to the following detailed description of the invention.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 4A-4C show meclofenamic acid (MFA) increases engraftment frequency. FIG. 4A) Estimated engrafting cell frequency for donor cells treated for 2 hours with 10 uM meclofenamic acid (MFA) is higher than for vehicle-treated donor cells (p=0.0367, paired t-test). Pre-transplantation treatment of donor cells with MFA increases the engraftment frequency of SMPs. FIG. 4B) Concentration and treatment time optimization of 10 uM MFA. FIG. 4C) Concurrent injection of donor cells with 10 uM MFA is not sufficient to increase engraftment frequency (p=0.0042, paired t-test).

FIG. 8A) BLI signals after transplant expressed as total radiance (p·s-1) (n=10 mice for vehicle, LPA or NFA treated). FIG. 8B) Engraftment of freshly sorted GFP/luc-labelled MuSCs (5000 cells) treated with vehicle, LPA or NFA for four hours. FIG. 8C) Transverse frozen section of TA muscle from FVB-NJ mice transplanted with 5,000 treated isolated satellite cells (Top). Enlarged area marked by the box in top row (bottom). Cell membrane (WGA, red), Nuclei (DAPI, blue) and CAG-luc-GFP (green).

FIGS. 11A-11H show the limiting Dilution Assay (LDA) experimental procedure and statistical analysis. (FIG. 11A) Outline of experimental design. Myogenic progenitor cells were generated in vitro from mylz2-GFP or mylz2-mcherry embryos. For LDA screening, cells were transplanted into pre-irradiated casper recipients (4- to 8-month-old) followed by imaging of the recipient fish at 7 dpt. (FIG. 11B) Log-fraction plot of the limiting dilution model fitted to the data in the table. The plot represents the fraction of positive responses as a function of the dose of cells delivered in each transplantation. The line slope is the log-active cell fraction and the 2 flanking dotted lines give the 95% confidence interval, as listed in the bottom table. (FIG. 11C) Images of muscle engraftment visualized by expression of the muscle-specific (mylz2-mCherry) reporter. Cells engrafted into casper fish were stably observed for as long as 1-year post-transplant. myosin light polypeptide chain 2 (Mylz2, red); dpt: days post transplantation; ypt: year post transplantation. Scale bar 500 μm. (FIG. 11D) Engrafted muscle-specific (mylz2-mCherry) cells are visible to the naked eye. myogenic factor 5 (Myf5, green) and myosin light polypeptide chain 2 (Mylz2, red). (FIG. 11E) myf5-GFP; mylz2-mCherry double-transgenic line cells were sorted into 4 subsets: myf5-GFP cells, mylz2-mCherry cells, double positive cells, and double negative cells. Each subset was evaluated for engraftment efficiency via limiting-dilution assays in 15 recipient zebrafish per donor cell type. (FIG. 11F) Muscle progenitor cells (myf5-GFP) show superior muscle engraftment in recipient fish (n=10 fish per dose). (FIG. 11G) Experimental design of the donor and recipient (4- to 8-month-old mylz2-mcherry fish) muscle cell fusion assay. (FIG. 11H) A cross section of a recipient fish at 7 dpt showing fusion of host and donor muscle fibers at the boundary of the engrafted region. The bottom row shows a zoomed image of the box in the top row. Scale bar 500 μm.

(FIG. 12A) Outline of experimental strategy. ZeMPCs were incubated with lipids for 4 hours at 28.5° C., followed by washing out of the media and drugs, harvesting the cells, and splitting into 3 cell doses (25, 75 or 200 cells/recipient) for transplantation. Treated cells were transplanted into each side of 5 pre-irradiated casper recipient fish or 5 non-irradiated prkdc-mutant recipient zebrafish (4- to 8-months-old), followed by imaging the recipient fish at 7 dpt. (FIG. 12B) Engraftment efficiency as assessed across different compound exposure times. LPA enhances the engraftment efficiency of ZeMPCs treated for 4 hours, while NFA enhances the engraftment efficiency after 2 and 4 hours of exposure. Fold increase of the engraftment efficiency was calculated as the ratio of the LPA- or NFA-treated cell potency and DMSO-treated cell potency. See also Figure S3 for cell potency values. (FIG. 12C and FIG. 12D) Engraftment efficiency of LPA-treated (FIG. 12C) or NFA-treated (FIG. 12D) ZePMCs assessed across different compound concentrations, as indicated.

(FIG. 14A) Experimental design. (FIG. 14B) Transplanted TA muscles were analyzed by BLI and histologically. Regression analysis shows a significant (n=17, P<0.0001) correlation between GFP-tagged myofibers and collected radiance via BLI in individual mice 5 weeks after transplantation. (FIG. 14C) Engraftment efficiency of 4-hour-treated mouse satellite cells with vehicle, LPA or NFA. 5,000 treated cells were injected into preinjured TA muscles and engraftment was measured by BLI 5 weeks after transplantation (n=19). (FIG. 14D) The bioluminescence image and transverse frozen section of representative low, medium, and high cell engraftments in TA muscles from FVB-NJ mice injected with 5,000 treated isolated satellite cells. Cell membrane (WGA, red), Nuclei (DAPI, blue), and CAG-luc-GFP (green). These studies used 8-16 weeks male mice. Scale bar 500 µm.

(FIG. 15A) Gene ontology (GO) enrichment analysis of differentially expressed genes in NEA-treated (right graph) or LPA-treated (left graph) mouse satellite cells. (FIG. 15B) Log 2-fold change in expression of selected genes in LPA and NFA treated mouse muscle stem cells.

(FIG. 16A) Schematic figure of swimming chamber and analysis strategy. (FIG. 16B, FIG. 16C, FIG. 16D, and FIG. 16E) Comparison of sapje-like (4- to 8-months old) swimming performance before and after transplantation. Data are expressed as means±SD and were analyzed by paired t-test (*p<0.05; **p<0.01).

(FIG. 18A) Experimental design to test the in vivo fusion of donor muscle cells together. (FIG. 18B) Cross section of a prkdc-mutant recipient zebrafish (4- to 8-months old) at 7 dpt, demonstrating fusion of the two genotypes of donor cells (GFP+mCherry+). Myosin light polypeptide chain 2 (Mylz2, red and green), and nuclei (blue). (FIG. 18C) Quantification of in vivo fusion of donor muscle cells in the recipient fish (n=3). Scale bar 100 µm.

(FIG. 20A) Experimental design of ZeMPC competitive transplantation assays using different combinations of chemical-treated or DMSO-treated ZeMPCs marked by mCherry or GFP. ZeMPCs were co-injected from mylz2-GFP and mylz2-mCherry donors into 4- to 8-months-old prkdc-mutant recipient zebrafish and imaged at 7 dpt to assess the engraftment of mylz2-mCherry (pre-transplantation treatment with DMSO) and mylz2-GFP (pre-transplantation treatment with DMSO, LPA or NFA) cells. (FIG. 20B) Engraftment efficiency of equal numbers of DMSO-treated mCherry cells vs. DMSO-treated GFP cells (left), DMSO-treated mCherry cells vs. LPA-treated GFP cells (middle) and DMSO-treated mCherry cells vs. NFA-treated GFP cells (right). DMSO-treated mylz2-mCherry ZeMPCs and mylz2-GFP ZeMPCs showed similar engraftment pattern (grey bars), whereas pre-treatment with NFA (red bars) or LPA (blue bars) provided a competitive advantage.

Figure 24:
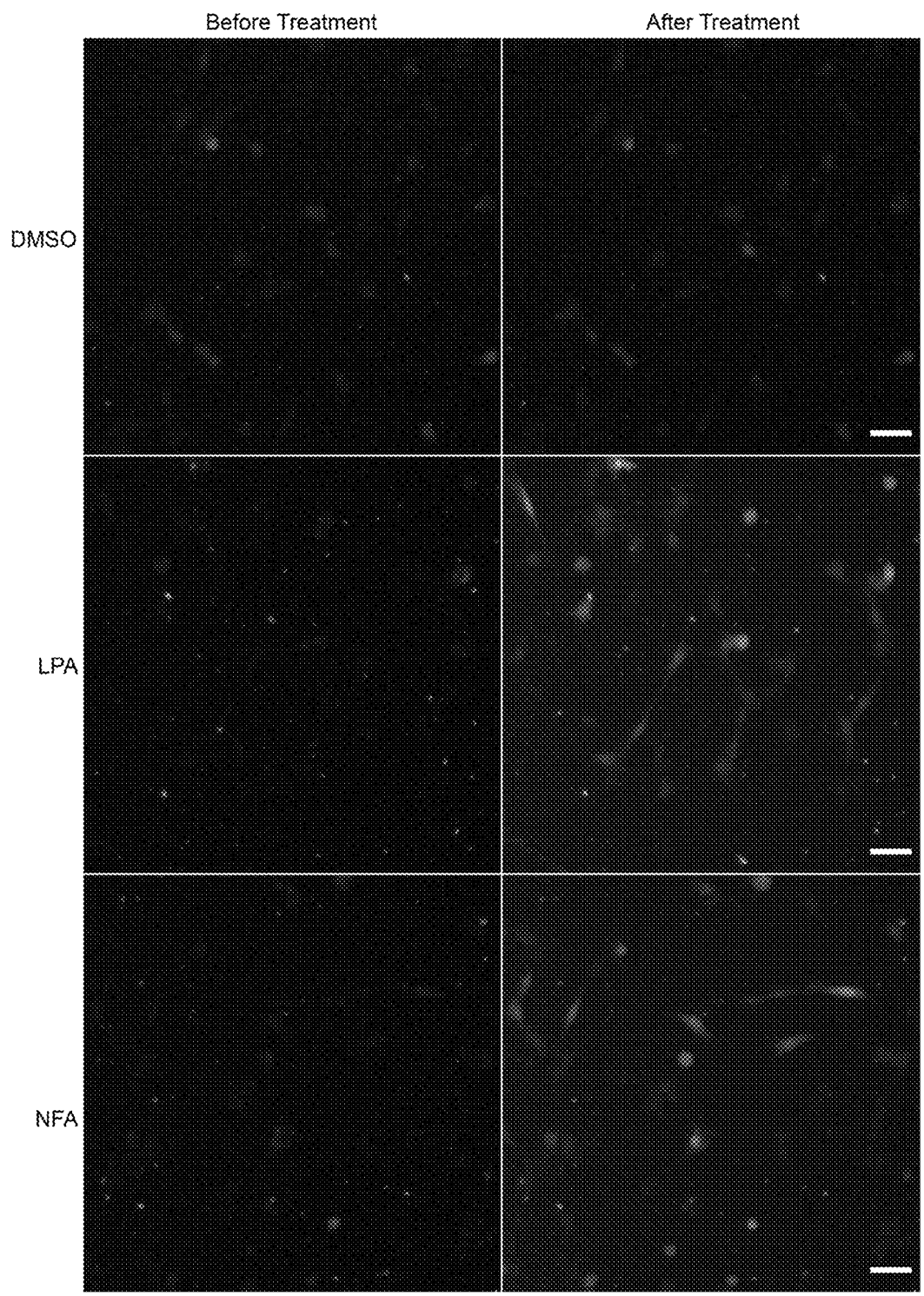

FIG. 24 shows intracellular calcium ion increases of NFA-treated and LPA-treated C2C12 cells. Fura-2, AM treated C2C12 cells were exposed to 10 μM NFA, 5 μM LPA or DMSO as vehicle control to visualize the effect on intracellular calcium ion concentration using single-cell imaging. Comparing signal intensity before loading the treatment (left column) to signal intensity 10-20 seconds after loading the treatment (right column), reveals NFA, LPA and ionomycin increase the intracellular calcium ion concentration. Scale bar 50 μm.

Figures 25A, 25B:
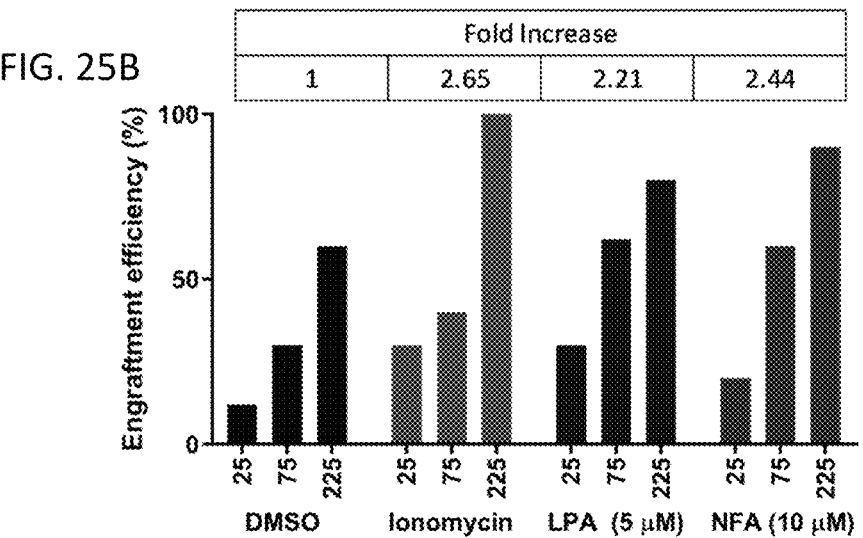

FIGS. 25A-25B show LPA and NFA increase intracellular calcium ion concentrations in mouse satellite cells. (FIG. 25A) Measurement of calcium ion concentration transients in Fluo4 AM-loaded mouse satellite cells. Each box reports the area under curve (AUC) inside the well containing the indicated concentrations of NFA, LPA, DMSO, and/or lonomycin. (FIG. 25B) Ionomycin (green bars), a positive control for increased intracellular calcium ion concentrations, enhances the engraftment efficiency of muscle cells in 4- to 8-month-old prkdc-mutant zebrafish relative to vehicle-treated controls (black bars), similar to LPA (blue bars) and NFA (red bars).

Figure 26:
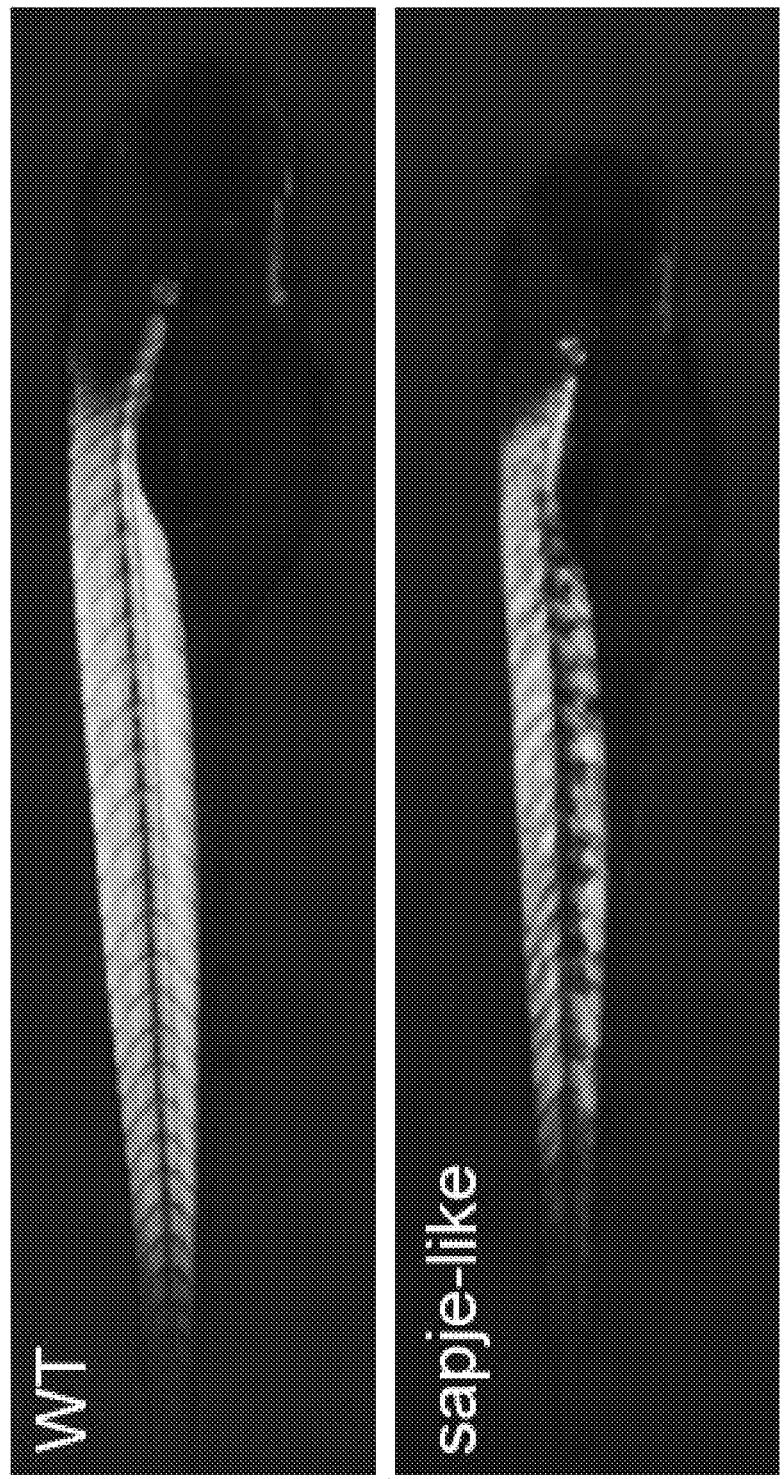

FIG. 26 shows muscle tissue visualization in sapje-like mutants and wild type (WT) fish using polarized light shows the patchy muscle phenotype in the mutants at 5 days post-fertilization (dpf).

DETAILED DESCRIPTION OF THE INVENTION

Work described herein applies an innovative zebrafish embryo culture and transplantation system to pursue imaging-based screening of chemical compounds that could be used to promote muscle progenitor cell engraftment in vivo. Specifically, it is shown herein that treatment with a number of identified agents can significantly enhance engraftment efficiency of muscle progenitor cells.

Some aspects of the disclosure are directed to a method of increasing the engraftment efficiency (e.g., in vivo engraftment efficiency) of myogenic progenitor cells comprising contacting one or more agents with the myogenic progenitor cells.

The agent may be a polypeptide, nucleic acid, lipid, or small molecule. In some embodiments, the one or more agents comprise a compound that increases intracellular $Ca^{2+}$ levels in myogenic progenitor cells. In some embodiments, the compound that increases intracellular $Ca^{2+}$ levels in myogenic progenitor cells (MPCs) increases influx of extracellular $Ca^{2+}$ and/or promotes release of mitochondrial $Ca^{2+}$ stores. In some embodiments, the one or more agents comprise a lipid. In some embodiments, the one or more agents comprise a compound that activates a G-protein-coupled receptor on MPCs. In some embodiments, the G-protein-coupled receptor is selected from one or more of LPAR1, LPAR2, LPAR3, LPAR4, LPAR5, and LPAR6. In some embodiments, the agent is a COX (e.g., COX-2) inhibitor. In some embodiments, the agent has one, two, three or four of the following properties: increases intracellular $Ca^{2+}$ levels in myogenic progenitor cells; is a lipid; activates a G-protein-coupled receptor on MPCs; and inhibits COX (e.g., COX-2). In some embodiments, the one or more agents comprise lonomycin, meclofenamic acid (MFA), lysophosphatidic acid (LPA), or niflumic acid (NFA). In some embodiments, the MPCs are contacted with both LPA and NFA as agents.

In some embodiments, the agent is a small molecule that enhances myogenic progenitor cell engraftment. The term "small molecule" refers to an organic molecule that is less than about 2 kilodaltons (kDa) in mass. In some embodiments, the small molecule is less than about 1.5 kDa, or less than about 1 kDa. In some embodiments, the small molecule is less than about 800 daltons (Da), 600 Da, 500 Da, 400 Da, 300 Da, 200 Da, or 100 Da. Often, a small molecule has a mass of at least 50 Da. In some embodiments, a small molecule is non-polymeric. In some embodiments, a small molecule is not an amino acid. In some embodiments, a small molecule is not a nucleotide. In some embodiments, a small molecule is not a saccharide. In some embodiments, a small molecule contains multiple carbon-carbon bonds and can comprise one or more heteroatoms and/or one or more functional groups important for structural interaction with proteins (e.g., hydrogen bonding), e.g., an amine, carbonyl, hydroxyl, or carboxyl group, and in some embodiments at least two functional groups. Small molecules often comprise one or more cyclic carbon or heterocyclic structures and/or aromatic or polyaromatic structures, optionally substituted with one or more of the above functional groups.

In some embodiments, the agent is a bioactive lipid. In some embodiments, bioactive lipids of the subject application include the eicosanoids (including the cannabinoids, leukotrienes, prostaglandins, lipoxins, epoxyeicosatrienoic acids, and isoeicosanoids), non-eicosanoid cannabinoid mediators, phospholipids and their derivatives such as phosphatidic acid (PA) and phosphatidylglycerol (PG), platelet activating factor (PAF) and cardiolipins as well as lysophospholipids such as lysophosphatidyl choline (LPC) and various lysophosphatidic acids (LPA). Bioactive signaling lipids also include the sphingolipids such as sphingomyelin, ceramide, ceramide-1-phosphate, sphingosine, sphingosylphosphoryl choline, sphinganine, sphinganine-1-phosphate (Dihydro-S1P) and sphingosine-1-phosphate. Sphingolipids and their derivatives represent a group of extracellular and intracellular signaling molecules with pleiotropic effects on important cellular processes. Other examples of bioactive signaling lipids include phosphatidylserine (PS), phosphatidylinositol (PI), phosphatidylethanolamine (PEA), diacylglyceride (DG), sulfatides, gangliosides, and cerebrosides.

In some embodiments, the engraftment efficiency of a population of contacted (i.e., treated) myogenic progenitor cells is increased by about 1.1-fold, 1.2-fold, 1.3-fold, 1.4-fold, 1.5-fold, 1.6-fold, 1.7-fold, 1.8-fold, 1.9-fold, 2-fold, 2.5-fold, 3-fold, 3.5-fold, 4-fold, 4.5-fold, 5-fold, 10-fold, 20-fold, or more, as compared to the engraftment efficiency of untreated myogenic progenitor cells. In some embodiments, the engraftment efficiency of the contacted (i.e., treated) myogenic progenitor cells is increased by at least 5%, at least 10%, at least 15%, at least 20%, at least 25%, at least 30%, at least 40%, at least 50%, at least 60%, at least 70%, at least 80%, at least 90%, at least 95%, at least 98%, at least 100%, at least 110%, at least 150%, at least 200%, at least 500%, at least 750%, at least 1000%, or more compared to the engraftment efficiency of untreated myogenic progenitor cells. In some embodiments, the engraftment efficiency of the contacted (i.e., treated) myogenic progenitor cells is sufficiently increased to make transplantation of myogenic progenitor cells therapeutically effective to treat a skeletal muscle condition or disease (e.g., muscular disease, neuromuscular disease).

In some embodiments, the at least one agent is contacted with the myogenic progenitor cells prior to, or simultaneously with, administration of the myogenic progenitor cells to a subject. In some embodiments, the myogenic progenitor cells are contacted with the at least one agent at least about 30 minutes, 1 hour, 1.5 hours, 2 hours, 2.5 hours, 3 hours, 3.5 hours, 4 hours, 5 hours, 6 hours, 7 hours, 8 hours, 9 hours, 10 hours, 12 hours, 24 hours, 2 days or more prior to administration (i.e., transplantation) of the myogenic progenitor cells into a subject. In some embodiments, the MPCs to be transplanted are from the subject (autologous) or are from another (allogenic). In some embodiments, the MPCs to be transplanted are cultured from the subject's cells or from the cells of another. In some embodiments, the MPCs to be transplanted are obtained from induced pluripotent stem cells derived from the subject's cells or from the cells of another. In some embodiments, the MPCs to be transplanted have been genetically modified or are derived from cells that are genetically modified. In some embodiments, the genetic modification corrects a defect associated with or causing a muscle condition or disease (e.g., DMD).

In some embodiments, the myogenic progenitor cells (MPCs) are contacted with the agent in vivo. In some embodiments, the MPCs are endogenous to the subject. In some embodiments, the MPCs have been previously administered to the subject. In some embodiments, the MPCs are administered at least about 30 minutes, 1 hour, 1.5 hours, 2 hours, 2.5 hours, 3 hours, 3.5 hours, 4 hours, 5 hours, 6 hours, 7 hours, 8 hours, 9 hours, 10 hours, 12 hours, 24 hours, 2 days or more prior to administration of the agent. In some embodiments, the agent is administered to the subject prior to administration of MPCs. In some embodiments, the agent is administered at least about 30 minutes, 1 hour, 1.5 hours, 2 hours, 2.5 hours, 3 hours, 3.5 hours, 4 hours, 5 hours, 6 hours, 7 hours, 8 hours, 9 hours, 10 hours, 12 hours, 24 hours, 2 days or more prior to administration of the MPCs. In some embodiments, the MPCs were previously cultured from the subject's cells or from the cells of another. In some embodiments, the MPCs were obtained from induced pluripotent stem cells derived from the subject's cells or from the cells of another. In some embodiments, the MPCs have been genetically modified or are derived from cells that are genetically modified. In some embodiments, the genetic modification corrects a defect associated with or causing a muscle condition or disease (e.g., DMD). In some embodiments, the subject was treated to correct a genetic defect in vivo or ex vivo. In some embodiments, the subject was treated to increase endogenous MPC levels.

Methods of correcting a genetic defect in vivo or ex vivo are known in the art. In some embodiments, a genetic defect can be corrected using sequence-targeting nucleases. The sequence-targeting nucleases that can be used in the methods disclosed herein are not limited and may be any sequence-targeting nucleases disclosed herein. In some embodiments, the sequence-targeting nuclease is a Zinc-Finger Nuclease (ZFN), a Transcription activator-like effector nuclease (TALEN), a Cas nuclease (e.g., Cas9 nuclease), or a functional fragment or functional variant thereof.

There are currently four main types of sequence-targeting nucleases (i.e., targetable nucleases, site specific nucleases) in use: zinc finger nucleases (ZFNs), transcription activator-like effector nucleases (TALENs), and RNA-guided nucleases (RGNs) such as the Cas proteins of the CRISPR/Cas Type II system, and engineered meganucleases. ZFNs and TALENs comprise the nuclease domain of the restriction enzyme FokI (or an engineered variant thereof) fused to a site-specific DNA binding domain (DBD) that is appropriately designed to target the protein to a selected DNA sequence. In the case of ZFNs, the DNA binding domain (DBD) comprises a zinc finger DBD. In the case of TALENs, the site-specific DBD is designed based on the DNA recognition code employed by transcription activator-like effectors (TALEs), a family of site-specific DNA binding proteins found in plant-pathogenic bacteria such as *Xanthomonas* species.

The Clustered Regularly Interspaced Short Palindromic Repeats (CRISPR) Type II system is a bacterial adaptive immune system that has been modified for use as an RNA-guided endonuclease technology for genome engineering. The bacterial system comprises two endogenous bacterial RNAs called crRNA and tracrRNA and a CRISPR-associated (Cas) nuclease, e.g., Cas9. The tracrRNA has partial complementarity to the crRNA and forms a complex with it. The Cas protein is guided to the target sequence by the crRNA/tracrRNA complex, which forms a RNA/DNA hybrid between the crRNA sequence and the complementary sequence in the target. For use in genome modification, the crRNA and tracrRNA components are often combined into a single chimeric guide RNA (sgRNA or gRNA) in which the targeting specificity of the crRNA and the properties of the tracrRNA are combined into a single transcript that localizes the Cas protein to the target sequence so that the Cas protein can cleave the DNA. The sgRNA often comprises an approximately 20 nucleotide guide sequence complementary or homologous to the desired target sequence followed by about 80 nt of hybrid crRNA/tracrRNA. One of ordinary skill in the art appreciates that the guide RNA need not be perfectly complementary or homologous to the target sequence. For example, in some embodiments it may have one or two mismatches. The genomic sequence which the gRNA hybridizes is typically flanked on one side by a Protospacer Adjacent Motif (PAM) sequence although one of ordinary skill in the art appreciates that certain Cas proteins may have a relaxed requirement for a PAM sequence. The PAM sequence is present in the genomic DNA but not in the sgRNA sequence. The Cas protein will be directed to any DNA sequence with the correct target sequence and PAM sequence. The PAM sequence varies depending on the species of bacteria from which the Cas protein was derived. Specific examples of Cas proteins include Cas1, Cas2, Cas3, Cas4, Cas5, Cas6, Cas7, Cas8, Cas9 and Cas10. In some embodiments, the site specific nuclease comprises a Cas9 protein. For example, Cas9 from *Streptococcus pyogenes* (Sp), *Neisseria meningitides, Staphylococcus aureus, Streptococcus thermophiles*, or *Treponema denticola* may be used. The PAM sequences for these Cas9 proteins are NGG, NNNNGATT, NNAGAA, NAAAAC, respectively. In some embodiments, the Cas9 is from *Staphylococcus aureus* (saCas9).

A number of engineered variants of the site-specific nucleases have been developed and may be used in certain embodiments. For example, engineered variants of Cas9 and FokI are known in the art. Furthermore, it will be understood that a biologically active fragment or variant can be used. Other variations include the use of hybrid site specific nucleases. For example, in CRISPR RNA-guided FokI nucleases (RFNs) the FokI nuclease domain is fused to the amino-terminal end of a catalytically inactive Cas9 protein (dCas9) protein. RFNs act as dimers and utilize two guide RNAs (Tsai, Q S, et al., Nat Biotechnol. 2014; 32(6): 569-576). Site-specific nucleases that produce a single-stranded DNA break are also of use for genome editing. Such nucleases, sometimes termed "nickases" can be generated by introducing a mutation (e.g., an alanine substitution) at key catalytic residues in one of the two nuclease domains of a site specific nuclease that comprises two nuclease domains (such as ZFNs, TALENs, and Cas proteins). Examples of such mutations include D10A, N863A, and H840A in SpCas9 or at homologous positions in other Cas9 proteins. A nick can stimulate HDR at low efficiency in some cell types. Two nickases, targeted to a pair of sequences that are near each other and on opposite strands can create a single-stranded break on each strand ("double nicking"), effectively generating a DSB, which can optionally be repaired by HDR using a donor DNA template (Ran, F. A. et al. Cell 154, 1380-1389 (2013). In some embodiments, the Cas protein is a SpCas9 variant. In some embodiments, the SpCas9 variant is a R661A/Q695A/Q926A triple variant or a N497A/R661A/Q695A/Q926A quadruple variant. See Kleinstiver et al., "High-fidelity CRISPR-Cas9 nucleases with no detectable genome-wide off-target effects," Nature, Vol. 529, pp. 490-495 (and supplementary materials) (2016); incorporated herein by reference in its entirety. In some embodiments, the Cas protein is C2c1, a class 2 type V-B CRISPR-Cas protein. See Yang et al., "PAM-Dependent Target DNA Recognition and Cleavage by C2c1 CRISPR-Cas Endonuclease," Cell, Vol. 167, pp. 1814-1828 (2016); incorporated herein by reference in its entirety. In some embodiments, the Cas protein is one described in US 20160319260 "Engineered CRISPR-Cas9 nucleases with Altered PAM Specificity" incorporated herein by reference.

The method of administering the at least one agent to the subject (e.g., contacting myogenic progenitor cells with the at least one agent in vivo) is not limited. In some embodiments, the at least one agent is administered orally, subcutaneously, topically, intramuscularly or intravenously to the subject. In specific embodiments, the at least one agent is administer intramuscularly or intravenously to the subject. The at least one agent can be administered regularly, for example, 1, 2, 3, or more times a day, weekly, bi-weekly, or monthly. In other embodiments, the at least one agent is administered continuously to the subject (e.g., by release from an implant, pump, sustained release formulation, intravenous drip, etc.). The dose of the agent to be administered can depend on multiple factors, including weight of the subject, frequency of administration, etc. Determination of dosages is routine for one of ordinary skill in the art.

The myogenic progenitor cells are not limited. In some embodiments, the myogenic progenitor cells are derived from stem cells (embryonic stem cells, induced pluripotent stem cells). In some embodiments, the stem cells are from the subject or are from another individual. In some embodiments, the stem cells are induced from cells obtained from the subject or are induced from cells obtained from another individual. In some embodiments, the myogenic progenitor cells are obtained from the subject. In some embodiments, the subject is subjected to a treatment to increase endogenous myogenic progenitor cells prior to obtaining myogenic progenitor cells from the subject. In some embodiments, the myogenic progenitor cells obtained from the subject are treated to correct a genetic defect prior to transplant into the subject. In some embodiments, cells obtained from a subject that are induced to obtain myogenic progenitor cells are treated to correct a genetic defect prior to transplant into the subject. In some embodiments, the myogenic progenitor cells are primate cells (human cells or non-human primate cells), rodent (e.g., mouse, rat, rabbit, hamster) cells, canine, feline, bovine, or other mammalian cells. In some embodiments, the myogenic progenitor cells are piscine (e.g., zebrafish) cells.

The subject is not limited. In some embodiments, the subject is a mammal, e.g. a human, non-human primate, rodent (e.g., mouse, rat, rabbit), ungulate (e.g., ovine, bovine, equine, caprine species), canine, or feline. In some embodiments, the subject is a zebrafish. In some embodiments, a human subject is between newborn and 6 months old. In some embodiments, a human subject is between 6 and 24 months old. In some embodiments, a human subject is between 2 and 6, 6 and 12, or 12 and 18 years old. In some embodiments a human subject is between 18 and 30, 30 and 50, 50 and 80, or greater than 80 years old. In some embodiments, the subject is at least about 50, 60, 65, 70, 75, 80, 85, or 90 years of age. In some embodiments, a subject is an adult. For purposes hereof a human at least 18 years of age is considered an adult. In some embodiments a subject is an embryo. In some embodiments a subject is a fetus. In certain embodiments the subject is a pregnant female in order to treat or cause a biological effect on an embryo or fetus in utero.

Non-limiting examples of "skeletal muscle conditions or diseases" as used herein include atrophy, bony fractures associated with muscle wasting or weakness, cachexia, denervation, diabetes, dystrophy, exercise-induced skeletal muscle fatigue, fatigue, frailty, inflammatory myositis, metabolic syndrome, neuromuscular disease, obesity, post-surgical muscle weakness, post-traumatic muscle weakness, sarcopenia, toxin exposure, wasting, and weakness.

As used herein, "frailty" is a syndrome characterized by meeting at least one of the following five attributes: unintentional weight loss, muscle weakness, slow walking speed, exhaustion, and low physical activity.

As used herein, "cachexia" means a state often associated with cancer or other serious diseases or conditions, (e.g., chronic obstructive pulmonary disease, chronic kidney disease), that is characterized by progressive weight loss, muscle atrophy and fatigue, due to the deletion of adipose tissue and skeletal muscle.

As used herein, "post-surgical muscle weakness" refers to a reduction in the strength of one or more muscles following surgical procedure. Weakness may be generalized (i.e., total body weakness) or localized to a specific area, side of the body, limb, or muscle.

As used herein, "post-traumatic muscle weakness" refers to a reduction in the strength of one or more muscles following a traumatic episode (e.g., bodily injury). Weakness may be generalized (e.g., total body weakness) or localized to a specific area, side of the body, limb, or muscle.

As used herein, "neuromuscular disease" means any disease or condition that affects any part of the nerve and muscle. Neuromuscular disease encompasses critical illness polyneuropathy, prolonged neuromuscular blockade, acute myopathy as well as acute inflammatory demyelinating polyradiculoneuropathy, amyotrophic lateral sclerosis (ALS), autonomic neuropathy, Charcot-Marie-Tooth disease and other hereditary motor and sensory neuropathies, chronic inflammatory demyelinating polyradiculoneuropathy, dermatomyositis/polymyositis, diabetic neuropathy, dystrophinopathies, endocrine myopathies, focal muscular atrophies, hemifacial spasm, hereditary neuropathies of the Charcot-Marie-Tooth disease type, inclusion body myositis, Kennedy disease, Lambert-Eaton myasthenic syndrome, muscular dystrophy (e.g., limb-girdle, Duchenne, Becker, myotonic, facioscapulohumeral, etc.), metabolic myopathies, metabolic neuropathy, multifocal motor neuropathy with conduction blocks, myasthenia gravis, neuropathy of Friedreich Ataxia, neuropathy of leprosy, nutritional neuropathy, periodic paralyses, primary lateral sclerosis, restrictive lung disease, sarcoidosis and neuropathy, Schwartz-Jampel Syndrome, spinal muscular atrophy (SMA), stiff person syndrome, thyroid disease, traumatic peripheral nerve lesions, vasculitic neuropathy, among others.

As used herein, "sarcopenia" means a loss of skeletal muscle mass, quality, and strength. Often sarcopenia is associated with aging, but may also occur in association with HIV infection and a variety of chronic conditions. Sarcopenia may lead to frailty, for example, in the elderly. Sacropenia also encompasses a condition or symptom associated with sacropenia including, but not limited to loss of skeletal muscle mass, muscle weakness, fatigue, disability, and morbidity.

In some embodiments, the subject would benefit from increased muscle strength or mass. In some embodiments, the subject has reduced muscle mass due to aging. In some embodiments, the subject has a muscular dystrophy. In some embodiments, the muscular dystrophy is selected from myotonic muscular dystrophy, Duchenne muscular dystrophy (DMD), Becker muscular dystrophy, limb-girdle muscular dystrophy, facioscapulohumeral muscular dystrophy, congenital muscular dystrophy, oculopharyngeal muscular dystrophy, distal muscular dystrophy, and Emery-Dreifuss muscular dystrophy. In some embodiments, the muscular dystrophy is Becker muscular dystrophy or Duchenne muscular dystrophy.

In some embodiments, the at least one agent is contacted with the myogenic progenitor cells at a concentration effective to increase engraftment efficiency by any amount described herein. In some embodiments, the concentration of NFA as an agent contacted with the myogenic progenitor cells is in the range of 0.1 µM to 10 mM, 0.1 µM to 1 mM, 0.1 µM to 500 µM, 0.1 µM to 200 µM, 0.1 µM to 150 µM, 0.3 µM to 50 µM, or about 10 µM to 20 µM. In some embodiments, a concentration of about 0.3 µM, about 15 µM or about 150 µM NFA is contacted with the myogenic progenitor cells. In some embodiments, the concentration of LPA as an agent contacted with the myogenic progenitor cells is in the range of 0.1 µM to 10 mM, 0.1 µM to 1 mM, 1 µM to 500 µM, 1 µM to 100 µM, 1 µM to 10 µM, 2 µM to 6 µM, or about 3 µM to 5 µM. In some embodiments, a concentration of about 0.1 µM, about 0.3 µM, about 1 µM, about 4 µM LPA, or about 10 µM is contacted with the myogenic progenitor cells. In some embodiments, the concentration of Ionomycin as an agent contacted with the myogenic progenitor cells is in the range of 0.1 µM to 10 mM, 0.1 µM to 1 mM, 0.1 µM to 500 µM, 0.1 µM to 200 µM, 0.1 µM to 150 µM, 0.3 µM to 50 µM, or about 10 µM to 20 µM. In some embodiments, a concentration of about 0.3 µM, about 15 µM or about 150 µM of Ionomycin is contacted with the myogenic progenitor cells.

In some embodiments, both NFA and LPA as agents are contacted with the myogenic progenitor cells. In some embodiments, the ratio of concentration of NFA to LPA contacted with the myogenic progenitor cells is about 3 to 1 (e.g., about 0.3 µM NFA to 0.1 µM LPA, about 0.6 µM NFA to 0.2 µM LPA, about 3 µM NFA to 1 µM LPA). In some embodiments, the ratio of concentration of NFA to LPA contacted with the myogenic progenitor cells is about 10 to 1, 3 to 1, 2 to 1, 1 to 1, 1 to 2, 1 to 3, or 1 to 10. In some embodiments, a concentration of about 0.1 to 100 µM NFA and about 0.1 µM to 100 µM LPA is contacted with the myogenic progenitor cells. In some embodiments, a concentration of about 0.1 to 10 µM NFA and about 0.1 µM to 10 µM LPA is contacted with the myogenic progenitor cells.

In some embodiments, the myogenic progenitor cells are contacted with the concentrations of NFA and LPA as set forth in Table 1.

Some aspects of the disclosure are directed to a method of enhancing tissue culture of muscle tissue, comprising adding one or more agents that increase the engraftment efficiency of myogenic progenitor cells into the muscle tissue. The one or more agents are not limited and may be any agents as described herein. In some embodiments, the agent is selected from a compound that increases intracellular $Ca^{2+}$ levels in myogenic progenitor cells, Ionomycin, meclofenamic acid (MFA), lysophosphatidic acid (LPA), and niflumic acid (NFA). In some embodiments, the tissue culture comprises zebrafish cells, mouse cells, or human cells. In some embodiments, the tissue culture comprises mouse cells. In some embodiments, the tissue culture comprises tissue obtained from a subject as described herein. In some embodiments, the tissue culture contains a concentration of LPA and/or NFA as described herein. In some embodiments, the tissue culture contains a concentration of Ionomycin as described herein. The myogenic progenitor cells are not limited and may be any myogenic progenitor cells as described herein. In some embodiments, the tissue culture is used to repair or replace muscle tissue in a subject.

Some aspects of the disclosure are directed to a method of screening for a test agent that enhances engraftment of myogenic progenitor cells comprising contacting the test agent with a population of myogenic progenitor cells, adding the contacted myogenic progenitor cells to a muscle tissue, and comparing engraftment into the muscle tissue of the contacted myogenic cells to engraftment into the muscle tissue of control myogenic progenitor cells not contacted with the test agent, thereby determining whether the test agent enhances engraftment. In some embodiments, at least one of the myogenic progenitor cells and the muscle tissue comprises a label (e.g., a fluorescent label). In some embodiments the fluorescent label is a green fluorescent protein, red fluorescent protein, or infrared fluorescent protein.

The myogenic progenitor cells are not limited and may be any myogenic progenitor cells described herein. The muscle cells are not limited and may be from, or derived from, any subject described herein. In some embodiments, the myogenic progenitor cells and the muscle cells are zebrafish cells. In some embodiments, the myogenic progenitor cells and the muscle cells are from a human. In some embodiments, the myogenic progenitor cells and the muscle cells are from a mouse.

Some aspects of the disclosure are directed to a method of screening for a test agent that enhances engraftment of myogenic progenitor cells comprising contacting the test agent with a population of myogenic progenitor cells and measuring changes in gene expression as compared to a control (e.g., gene expression in uncontacted myogenic progenitor cells). In some embodiments, the test agent is identified as an enhancer of engraftment of myogenic progenitor cells if contact with the agent increases the expression of calcium dependent genes (e.g., one or more of the calcium dependent genes provided in FIG. 21) and/or decreases the expression of muscle development genes (e.g., one or more of the muscle development genes provided in FIG. 21).

Figure 21:
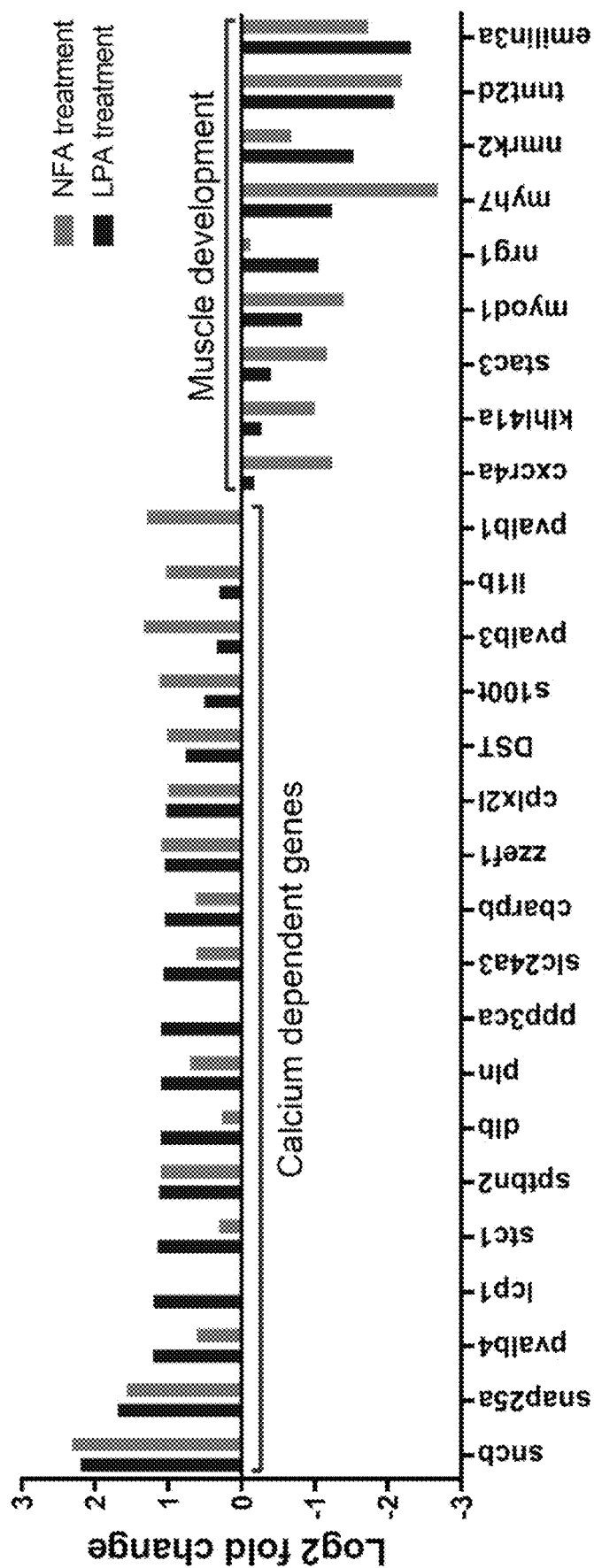
FIG. 21 shows differential gene expression pattern reveals the upregulation of calcium ion-dependent genes in treated ZeMPCs. Log 2-fold change in expression of selected genes in LPA and NFA treated ZeMPCs.

In some embodiments, the test agent is identified as an enhancer of engraftment of myogenic progenitor cells if contact with the agent increases the expression of 1, 2, 3, 4, 5, 6, 7, 8, 9, 10, 11, 12, 13, 14, 15, 16, 17, or all 18 calcium dependent genes selected from the calcium dependent genes listed in FIG. 21 or a functionally equivalent, homologous, or orthologous gene thereto (e.g., a functionally equivalent, homologous, or orthologous gene in a non-zebrafish cell). In some embodiments, the test agent is identified as an enhancer of engraftment of myogenic progenitor cells if contact with the agent increases the expression of 1, 2, 3, 4, 5, 6, 7, 8, or all 9 muscle development genes selected from the muscle development genes listed in FIG. 21 or a functionally equivalent, homologous, or orthologous gene thereto (e.g., a functionally equivalent, homologous, or orthologous gene in a non-zebrafish cell). In some embodiments, the test agent is identified as an enhancer of engraftment of myogenic progenitor cells if it increases the expression of sncb or snap25a by about 10-fold, 50-fold, 100-fold, or more. In some embodiments, the test agent is identified as an enhancer of engraftment of myogenic progenitor cells if it decreases the expression of tnnt2d or emilin3a by about 10-fold, 50-fold, 100-fold, or more.

The myogenic progenitor cells are not limited and may be any myogenic progenitor cells described herein. The muscle cells are not limited and may be from, or derived from, any subject described herein. In some embodiments, the myogenic progenitor cells and the muscle cells are zebrafish cells. In some embodiments, the myogenic progenitor cells and the muscle cells are from a human. In some embodiments, the myogenic progenitor cells and the muscle cells are from a mouse.

Some aspects of the disclosure are directed to a composition comprising myogenic progenitor cells and one or more agents that enhance engraftment of the myogenic progenitor cells into muscle tissue.

The agents are not limited and may be any agent described herein. In some embodiments, the one or more agents comprise a compound that increases intracellular $Ca^{2+}$ levels in myogenic progenitor cells. In some embodiments, the compound that increases intracellular $Ca^{2+}$ levels in myogenic progenitor cells (MPCs) increases influx of extracellular $Ca^{2+}$ and/or promotes release of mitochondrial $Ca^{2+}$ stores. In some embodiments, the one or more agents comprise a lipid. In some embodiments, the one or more agents comprise a membrane permeable calcium ionophore (e.g., Ionomycin). In some embodiments, the one or more agents comprise a compound that activates a G-protein-coupled receptor on MPCs. In some embodiments, the one or more agents comprise Ionomycin, meclofenamic acid (MFA), lysophosphatidic acid (LPA), or niflumic acid (NFA). In some embodiments, the composition comprises both LPA and NFA as agents.

In some embodiments, the concentration of NFA as an agent is in the range of 0.1 μM to 10 mM, 0.1 μM to 1 mM, 0.1 μM to 500 μM, 0.1 μM to 200 μM, 0.1 μM to 150 μM, 0.3 μM to 50 μM, or about 10 μM to 20 μM. In some embodiments, the concentration of NFA as an agent is about 0.3 μM, about 15 μM or about 150 μM NFA. In some embodiments, the concentration of LPA as an agent is in the range of 0.1 μM to 10 mM, 0.1 μM to 1 mM, 1 μM to 500 μM, 1 μM to 100 μM, 1 μM to 10 μM, 2 μM to 6 μM, or about 3 μM to 5 μM. In some embodiments, the concentration of LPA as an agent is about 0.1 μM, about 0.3 μM, about 1 μM, about 4 μM LPA, or about 10 μM. In some embodiments, the one or more agents comprise MFA at a concentration of about 1-50 uM MPA. In some embodiments, the concentration of Ionomycin as an agent contacted with the myogenic progenitor cells is in the range of 0.1 μM to 10 mM, 0.1 μM to 1 mM, 0.1 μM to 500 μM, 0.1 μM to 200 μM, 0.1 μM to 150 μM, 0.3 μM to 50 μM, or about 10 μM to 20 μM. In some embodiments, a concentration of about 0.3 μM, about 15 μM or about 150 μM of Ionomycin is contacted with the myogenic progenitor cells.

In some embodiments, the ratio of concentrations of NFA to LPA in the composition is about 3 to 1 (e.g., about 0.3 μM NFA to 0.1 μM LPA, about 0.6 μM NFA to 0.2 μM LPA, about 3 μM NFA to 1 μM LPA). In some embodiments, the ratio of concentrations of NFA to LPA in the composition is about 10 to 1, 3 to 1, 2 to 1, 1 to 1, 1 to 2, 1 to 3, or 1 to 10. In some embodiments, the composition comprises a concentration of about 0.1 to 100 μM NFA and about 0.1 μM to 100 μM LPA. In some embodiments, the composition comprises a concentration of about 0.1 to 10 μM NFA and about 0.1 μM to 10 μM LPA. In some embodiments, the composition comprises concentrations of NFA and LPA as set forth in Table 1. In some embodiments, the composition further comprises Ionomycin.

The myogenic progenitor cells are not limited and may be any myogenic progenitor cells described herein. The muscle cells are not limited and may be from, or derived from, any subject described herein. In some embodiments, the myogenic progenitor cells and the muscle cells are zebrafish cells. In some embodiments, the myogenic progenitor cells and the muscle cells are from a human. In some embodiments, the myogenic progenitor cells and the muscle cells are from a mouse.

Some aspects of the disclosure are directed to a composition comprising one or more agents that increase the engraftment efficiency of myogenic progenitor cells into muscle tissue of a subject, and a pharmaceutically acceptable diluent or excipient. The agents are not limited and may be any agent described herein. In some embodiments, the agent is selected from a compound that increases intracellular $Ca^{2+}$ levels in myogenic progenitor cells, meclofenamic acid (MFA), lysophosphatidic acid (LPA), and niflumic acid (NFA). In some embodiments, the composition comprises at least two, at least three, at least four, or more agents. In some embodiments, the composition comprises at least two agents selected from Ionomycin, meclofenamic acid (MFA), lysophosphatidic acid (LPA), and niflumic acid (NFA). In some embodiments, the composition comprises, consists essentially of, or consists of LPA, NFA and one or more pharmaceutically acceptable diluents and/or excipients.

The preparation of a pharmacological composition that contains active ingredients dissolved or dispersed therein is well understood in the art and generally need not be limited based on formulation. Typically such compositions are prepared as injectable either as liquid solutions or suspensions, however, solid forms suitable for solution, or suspension, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents, and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic, and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine, and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline.

Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the invention that will be effective in the treatment of a particular disorder or condition will depend on the nature of the disorder or condition, and can be determined by standard clinical techniques.

In some embodiments, an agent as described herein can be administered by controlled- or delayed-release means. Controlled release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Chemg-ju, Controlled-release Dosage Form Design, 2 (Technomic Publishing, Lancaster, Pa.: 2000).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like.

Advantageously, controlled-release formulations can be used to control an agent's onset of action (e.g., enhancement of MPC engraftment), duration of action, plasma levels within the therapeutic window, and peak blood levels. In particular, controlled or extended-release dosage forms or formulations can be used to ensure that the maximum effectiveness of an agent is achieved while minimizing potential adverse effects and safety concerns, which can occur both from under-dosing an agent (i.e., going below the minimum active levels) as well as exceeding the toxicity level for the agent.

Most controlled-release formulations are designed to initially release an amount of an agent that promptly produces the desired therapeutic effect (e.g., enhancement of MPC engraftment), and gradually and continually release other amounts of drug to maintain this level of therapeutic or prophylactic effect over an extended period of time. In order to maintain this constant level of agent in the body, the agent must be released from the dosage form at a rate that will replace the amount of agent being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B 1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In some embodiments, the technology described herein relates to a syringe comprising a therapeutically effective amount of a composition e.g. a pharmaceutical preparation comprising an agent as described herein.

As used herein, the phrase "therapeutically effective amount", "effective amount" or "effective dose" refers to an amount that enhances engraftment of myogenic progenitor cells. In some embodiments, a therapeutically effective amount enhances engraftment efficiency of myogenic progenitor cells by about 1.1-fold, 1.2-fold, 1.3-fold, 1.4-fold, 1.5-fold, 1.6-fold, 1.7-fold, 1.8-fold, 1.9-fold, 2-fold, 2.5-fold, 3-fold, 3.5-fold, 4-fold, 4.5-fold, 5-fold, 10-fold, 20-fold, or more as compared to the engraftment efficiency of untreated myogenic progenitor cells. In some embodiments, a therapeutically effective amount enhances engraftment efficiency of myogenic progenitor cells by at least 5%, at least 10%, at least 15%, at least 20%, at least 25%, at least 30%, at least 40%, at least 50%, at least 60%, at least 70%, at least 80%, at least 90%, at least 95%, at least 98%, at least 100%, at least 110%, at least 150%, at least 200%, at least 500%, at least 750%, at least 1000%, or more compared to the engraftment efficiency of untreated myogenic progenitor cells. In some embodiments, a therapeutically effective amount enhances engraftment efficiency of myogenic progenitor cells to a sufficient level to make transplantation of myogenic progenitor cells effective to treat a skeletal muscle condition or disease (e.g., muscular disease, neuromuscular disease).

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

In some embodiments, the methods further comprise administering a composition described herein along with one or more additional agents, biologics, drugs, or treatments beneficial to a subject suffering from a disorder or disease.

The above other therapeutic agents, when employed in combination with the chemical entities described herein, may be used, for example, in those amounts indicated in the Physicians' Desk Reference (PDR) or as otherwise determined by one of ordinary skill in the art.

For convenience, certain terms employed herein are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention. Unless otherwise defined, all technical and scientific terms used herein have the meaning commonly understood by one of skill in the art.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The term "statistically significant" or "significantly" refers to statistical significance and generally means a "p" value greater than 0.05 (calculated by the relevant statistical test). Those skilled in the art will readily appreciate that the relevant statistical test for any particular experiment depends on the type of data being analyzed. Additional definitions are provided in the text of individual sections below.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); The ELISA guidebook (Methods in molecular biology 149) by Crowther J. R. (2000); Immunology by Werner Luttmann, published by Elsevier, 2006. Definitions of common terms in molecular biology can also be found in Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001) and Davis et al., Basic Methods in Molecular Biology, Elsevier Science Publishing, Inc., New York, USA (1995) which are both incorporated by reference herein in their entireties.

As used herein, "treat," "treatment," "treating," or "amelioration" when used in reference to a disease, disorder or medical condition (e.g., a skeletal muscle condition or disease), refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, alleviation of one or more symptom(s), diminishment of extent of the deficit, stabilized (i.e., not worsening) state as compared to that expected in the absence of treatment.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or prior publication, or for any other reason. All statements as to the date or representation as to the contents of these documents is based on the information available to the applicants and does not constitute any admission as to the correctness of the dates or contents of these documents.

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more active agents, additives, ingredients, optional agents, types of organism, disorders, subjects, or combinations thereof, can be excluded.

Where the claims or description relate to a composition of matter, it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., it is to be understood that methods of making compositions useful for performing the method, and products produced according to the method, are aspects of the invention, unless otherwise indicated or unless it would be evident to one of ordinary skill in the art that a contradiction or inconsistency would arise.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately".

"Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated".

EXAMPLES

Example 1

Figure 1:
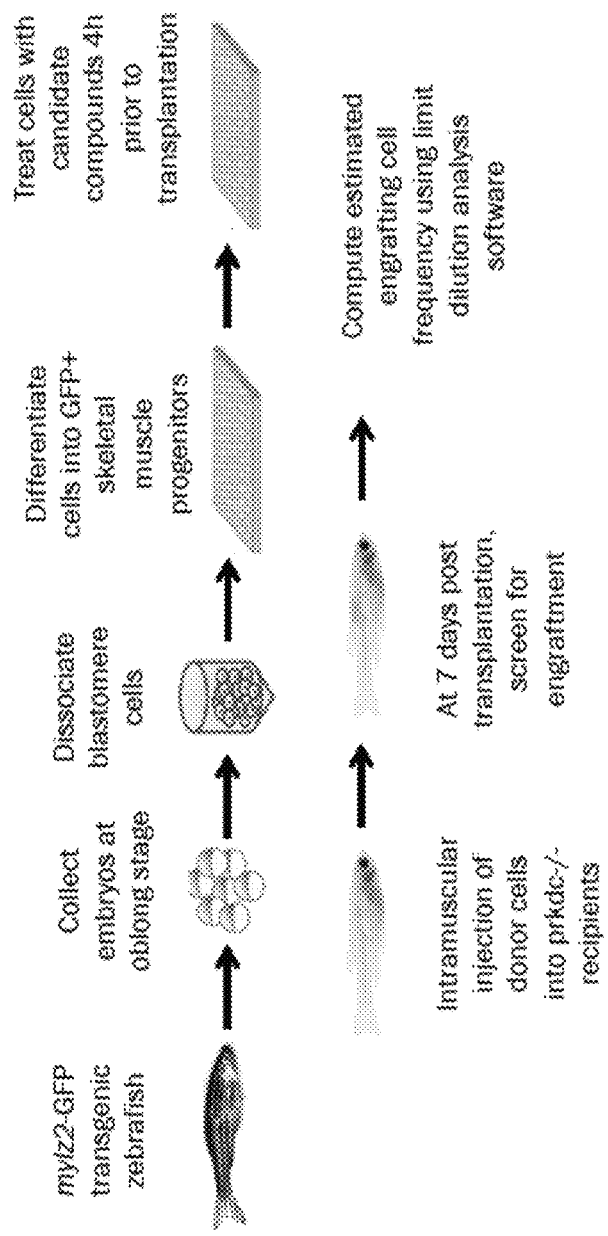
FIG. 1 shows an in vivo screen of candidate small molecules in zebrafish allows for the rapid identification of molecules that increase SMP (i.e., skeletal muscle progenitors, myogenic progenitor cells, MPCs) engraftment frequency. Donor cells were derived from embryos that contained a GFP cassette driven by the promoter for mylz2, a muscle-specific structural protein. Recipients were optically clear, immunocompromised adult prkdc-/- zebrafish. To perform a limiting dilution assay, three doses (n=100, 200, and 400 cells) were administered per treatment (n=10 engraftment events per treatment-dose combination). The estimated engrafting cell frequency was calculated using the Extreme Limiting Dilution Analysis (ELDA, Hu et. al. 2009), which provides the most likely estimate (MLE) of engrafting cell frequency.
Figure 2:
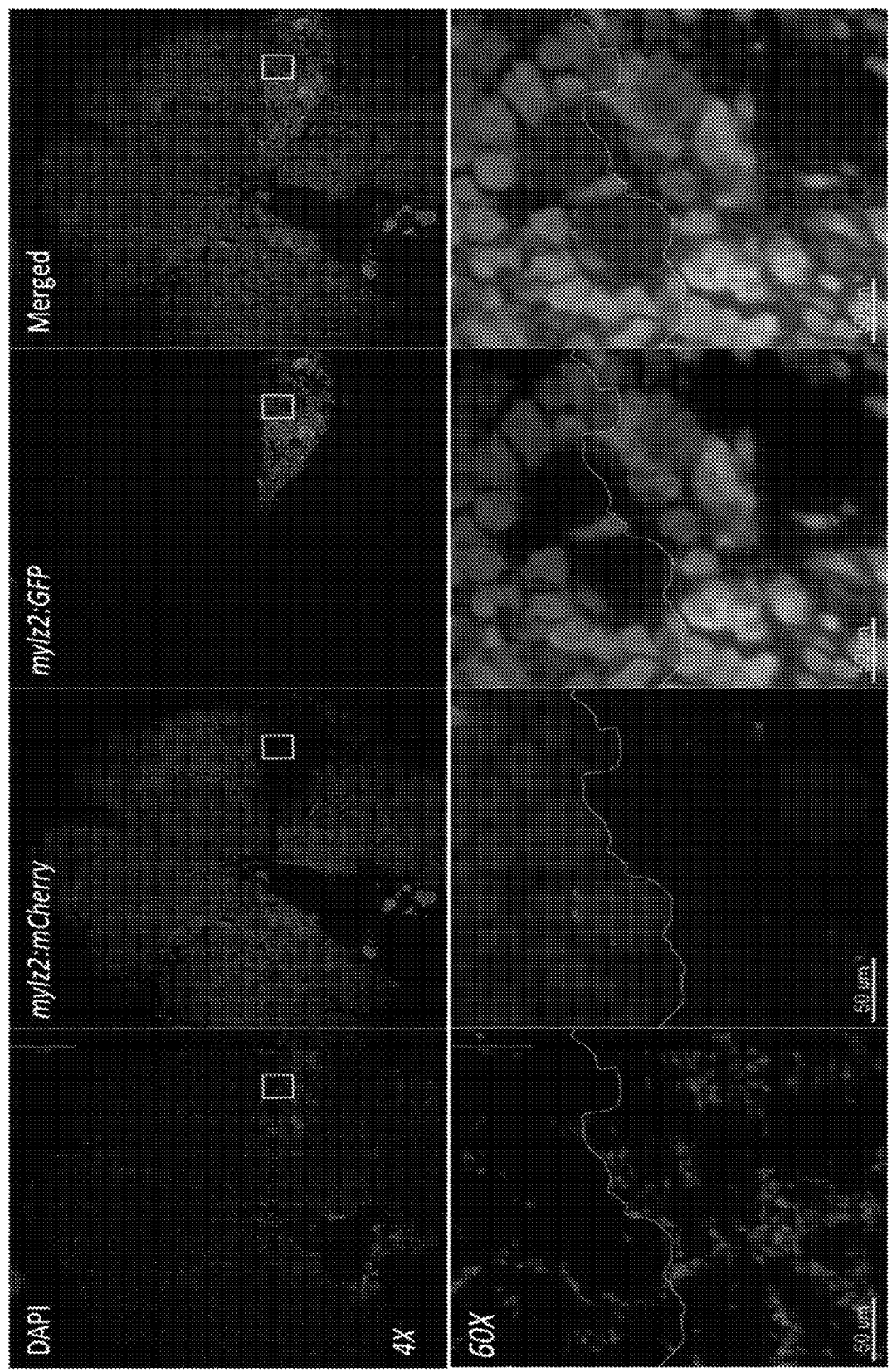
FIG. 2 is a photomicrograph showing chimeric muscle tissue from zebrafish. This chimeric tissue harbors 2 batches of cells with different origins and genetic makeup. The GFP$^{+ve}$ cells originated from the donor transplanted cells that carry the mylz2:GFP cassette in their genome and engrafted in the recipient fish with mCherry expression in its muscle cells. Top row shows 4× magnification and bottom row shows 60× magnification. The yellow line shows the boundary of engrafted regions at 2 weeks post transplantation. mylz2:mCherry (Red), mylz2:GFP (Yellow) and DAPI (Blue). Scale bar=50 μm.
Figure 3:
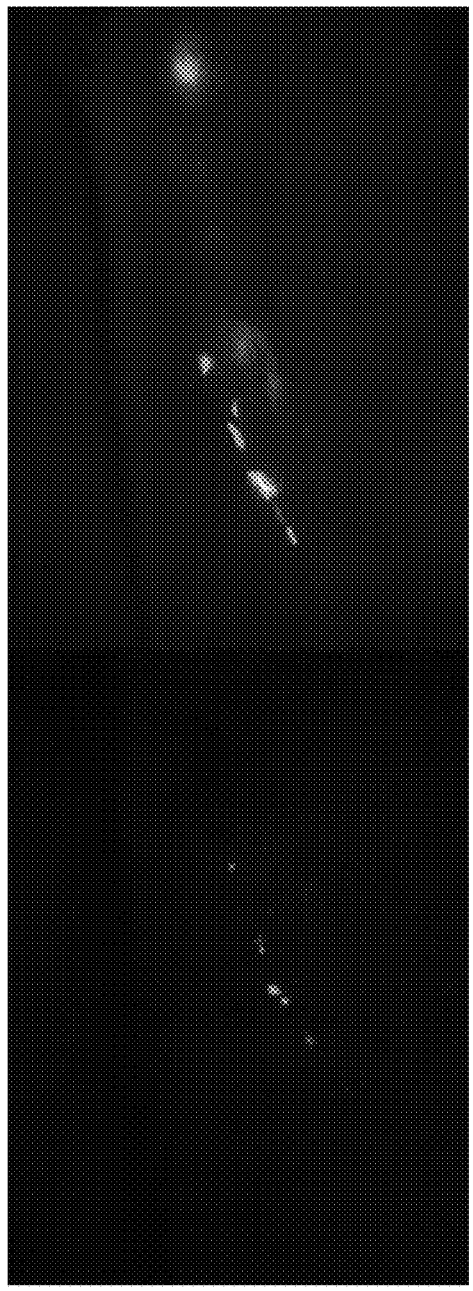
FIG. 3 shows the size of the engraftment patch in zebrafish increases during the 7 days post transplantation (n=100 cells, representative images). As muscle fibers are post-mitotic, this increase is likely due to fusion of myonuclei from transplanted rnylz2-negative SMPs.
Figure 3:
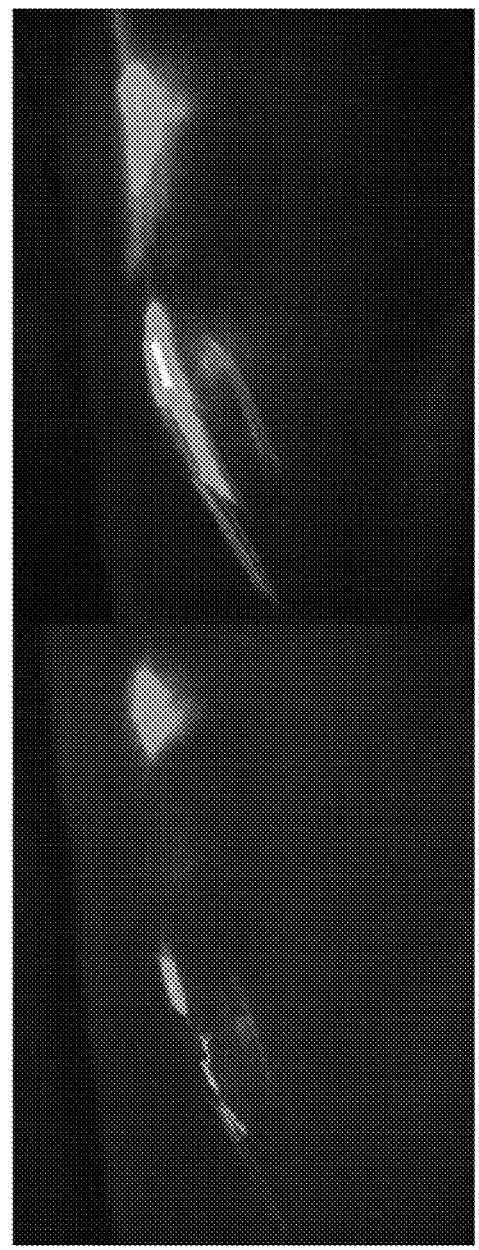

Here, it was aimed to address critical challenges with muscle progenitor cell engraftment by applying an innovative zebrafish embryo culture and transplantation system to pursue imaging-based screening of chemical compounds that could be used to promote muscle progenitor cell engraftment in vivo (FIG. 1, FIG. 2, FIG. 3). The efforts to date have focused on a well-annotated library of 230 bioactive lipids. The choices were narrowed down to lipids as it has been shown in different studies that lipids enhance hematopoiesis and adult marrow engraftment. Furthermore, a common cell membrane receptor drug target, G-protein-coupled receptors (GPCRs) are lipid-dependent.

Figure 5:
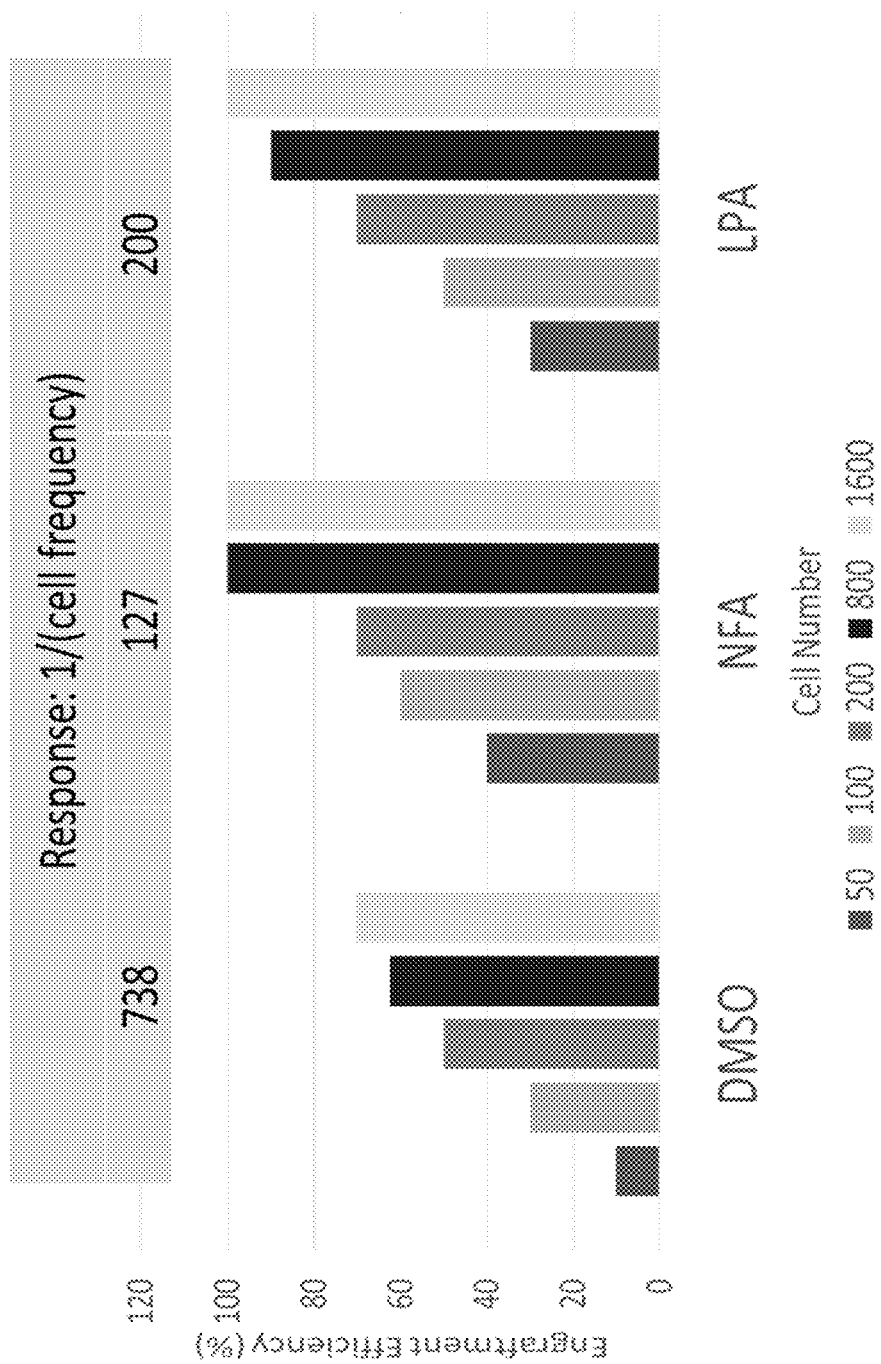
FIG. 5 provides graphs showing improved engraftment efficiency in muscle. Donor cells were divided into 3 groups and treated with DMSO (vehicle), niflumic acid (NFA), or lysophosphatidic acid (LPA) ex vivo. Cells from each group were divided into 5 subgroups with different cell numbers (50 cells, 100 cells, 200 cells, 800 cells or 1600 cells), followed by transplantation into the recipient fish. N=10 per subgroup. Treatment duration=4 hours.

Given that this group of 230 lipids is too many to be examined in mice, transplantation efficiency was instead examined via limit-dilution assays in 15 recipient zebrafish per compound after a brief (4 hour) ex vivo chemical exposure. Positive hits from this primary screening were rescreened in replicate transplantation experiments incorporating dose response testing. Results to date include robust and reproducible effects of 2 lipid biomolecules, lysophosphatidic acid (LPA) and niflumic acid (NFA), in increasing the engraftment capacity of transplanted myogenic progenitors in recipient adult zebrafish (FIG. 5). Further, MFA was also found to increase the engraftment capacity of transplanted myogenic progenitors in recipient adult zebrafish (FIGS. 4A-4C).

Figure 6:
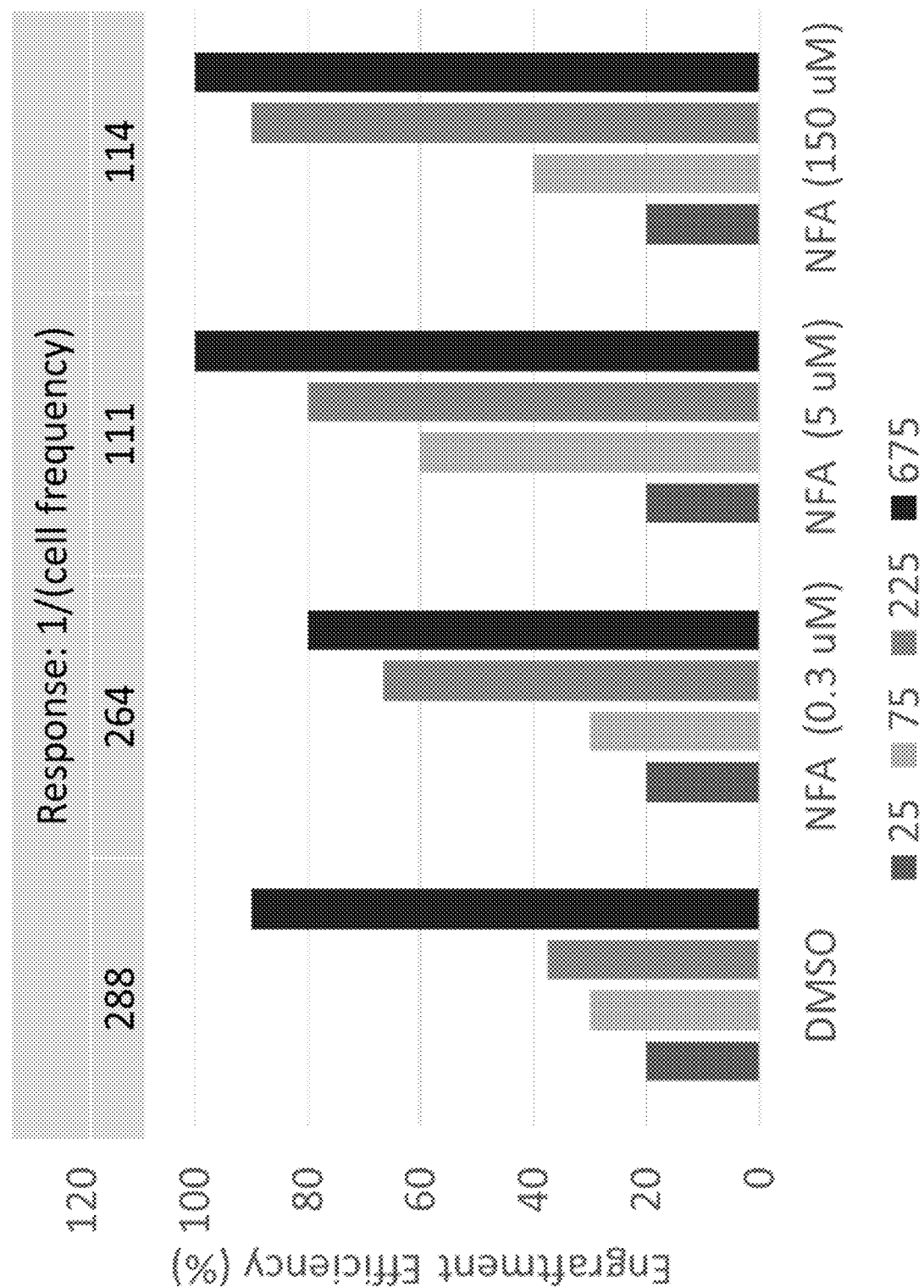
FIG. 6 shows the results of a dose response assay. The donor cells were divided into 4 groups and treated with DMSO (vehicle), 0.3 uM NFA, 5 uM NFA or 150 uM NFA ex vivo. Cells from each group were divided into 4 subgroups with different cell numbers (25 cells, 75 cells, 225 cells or 675 cells), followed by transplantation into recipient fish. N=10 per subgroup. Treatment duration=4 hours.
Figure 7:
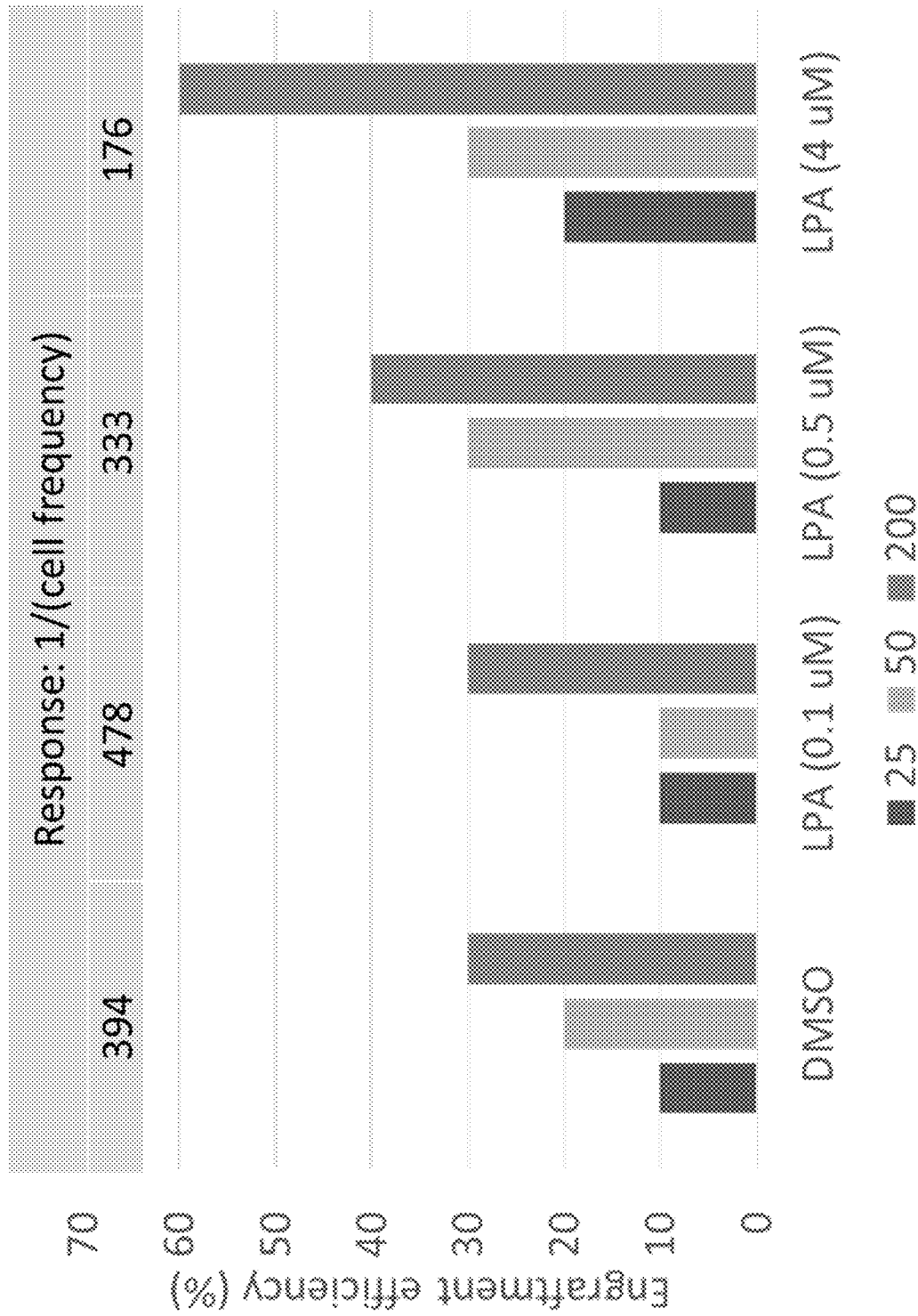
FIG. 7 shows the results of a dose response assay. The donor cells were divided into 4 groups and treated with DMSO (vehicle), 0.1 uM LPA, 0.5 uM LPA or 4 uM LPA ex vivo. Cells from each group were divided into 4 subgroups with different cell numbers (25 cells, 75 cells, 225 cells or 675 cells), followed by transplantation into recipient fish. N=10 per subgroup. Treatment duration=4 hours.

Next, limit-dilution assays were used to find the optimized concentration of LPA and NFA, as well as the concentration of either NFA or LPA that does not affect engraftment efficiency. FIG. 6 and FIG. 7 show that treating cells with 0.3 uM NFA, 0.1 uM LPA or 0.3 uM LPA did not change the engraftment efficiency in comparison to the engraftment efficiency of control DMSO treated cells. However, treating cells with either 15 uM NFA or 4 uM LPA increased engraftment efficiency. Limit dilutions assays were also used to determine optimized concentrations and treatment time of MFA for engraftment efficiency. 10 µM of MFA for 2 hours prior to injection was found to optimally increase engraftment (FIGS. 4A-4C).

LPA and NFA were also combined at different concentrations to examine the additive effects of these two molecules. Interestingly, the combination of these two molecules, at concentrations that were not individually effective, increased engraftment efficiency significantly (Table 1).

TABLE 1

Engraftment efficiencies of donor cells with different treatments combinations.

| Treatment | Response: 1/(cell frequency) |
|---|---|
| DMSO | 692 |
| 0.3 uM NFA + 0.1 uM LPA | 155 |
| 0.3 uM NFA + 0.3 uM LPA | 177 |
| 0.3 uM NFA + 1 uM LPA | 234 |
| 0.3 uM NFA + 10 uM LPA | 234 |
| 0.3 uM LPA + 0.1 uM NFA | 91.6 |
| 0.3 uM LPA + 0.3 uM NFA | 201 |
| 0.3 uM LPA + 1 uM NFA | 166 |
| 0.3 uM LPA + 10 uM NFA | 166 |

Figure 8B:
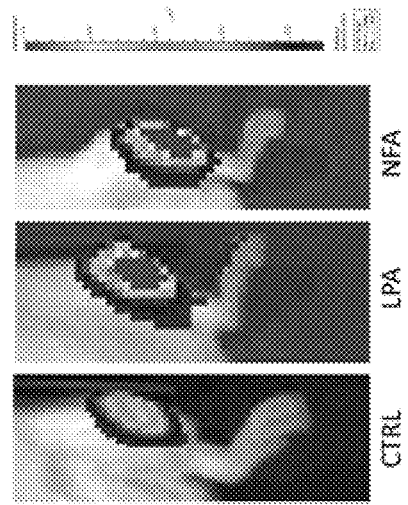
FIGS. 8A-8C show NFA and LPA treatment of murine muscle satellite cells enhance engraftment efficiency.
Figure 8A:
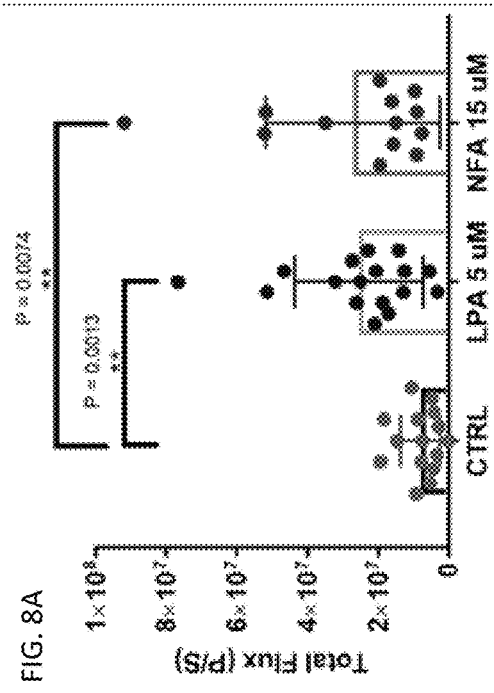
Figure 8C:
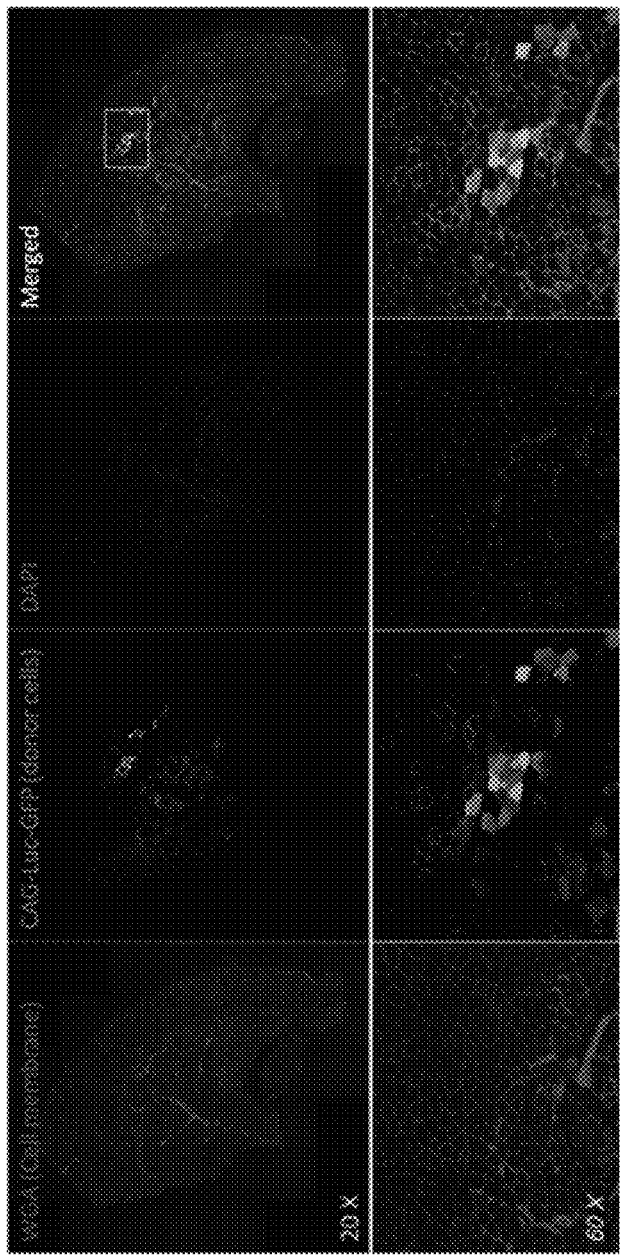

Importantly, the pro-myogenic effects of LPA and NFA appear to be conserved in mammalian regenerative myogenesis, as mouse muscle progenitors similarly exposed to these compounds before transplantation showed enhanced engraftment efficiency in comparison to the non-treated and vehicle-exposed cells using a bioluminescence imaging (BLI) model. Specifically, BLI radiance (mean±SEM) for muscle precursors treated with 10 µM NFA or 5 µM LPA prior to transplant were 27,236,923±6,849,754 p/s (n=13) and 25,637,059±4,410,195 p/s (n=17), respectively, in comparison to 8,214,000±1,462,346 p/s (n=15) vehicle-treated cells (1-way ANOVA between vehicle-treated group and either NFA or LPA treated group, p≤0.01) (FIGS. 8A-8C).

Figure 9:
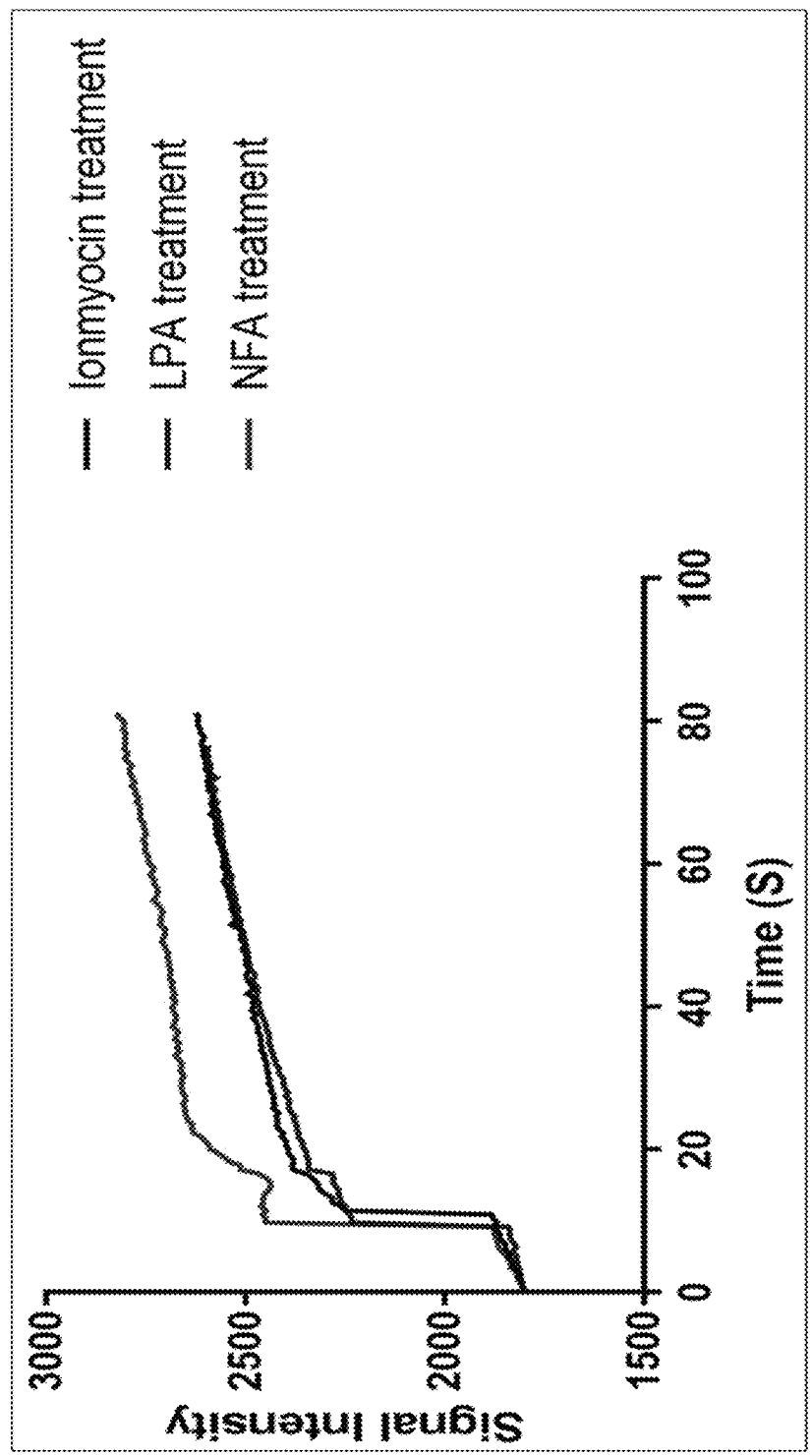
FIG. 9 shows that LPA and NFA increase intracellular $Ca^{+2}$ in muscle progenitor cells. Measurement of $Ca2+$ transients was performed in fura-2 AM-loaded cells.

It was further demonstrated that both LPA and NFA stimulate increases in cytoplasmic Ca2+ concentration: LPA by increasing influx of extracellular $Ca^{2+}$ and NFA by promoting release of mitochondrial $Ca^{2+}$ stores. Thus, it is possible that the enhanced engraftment capacity of muscle progenitor cells exposed to these compounds involves a common $Ca^{2+}$-dependent signaling events (FIG. 9).

Figure 10:
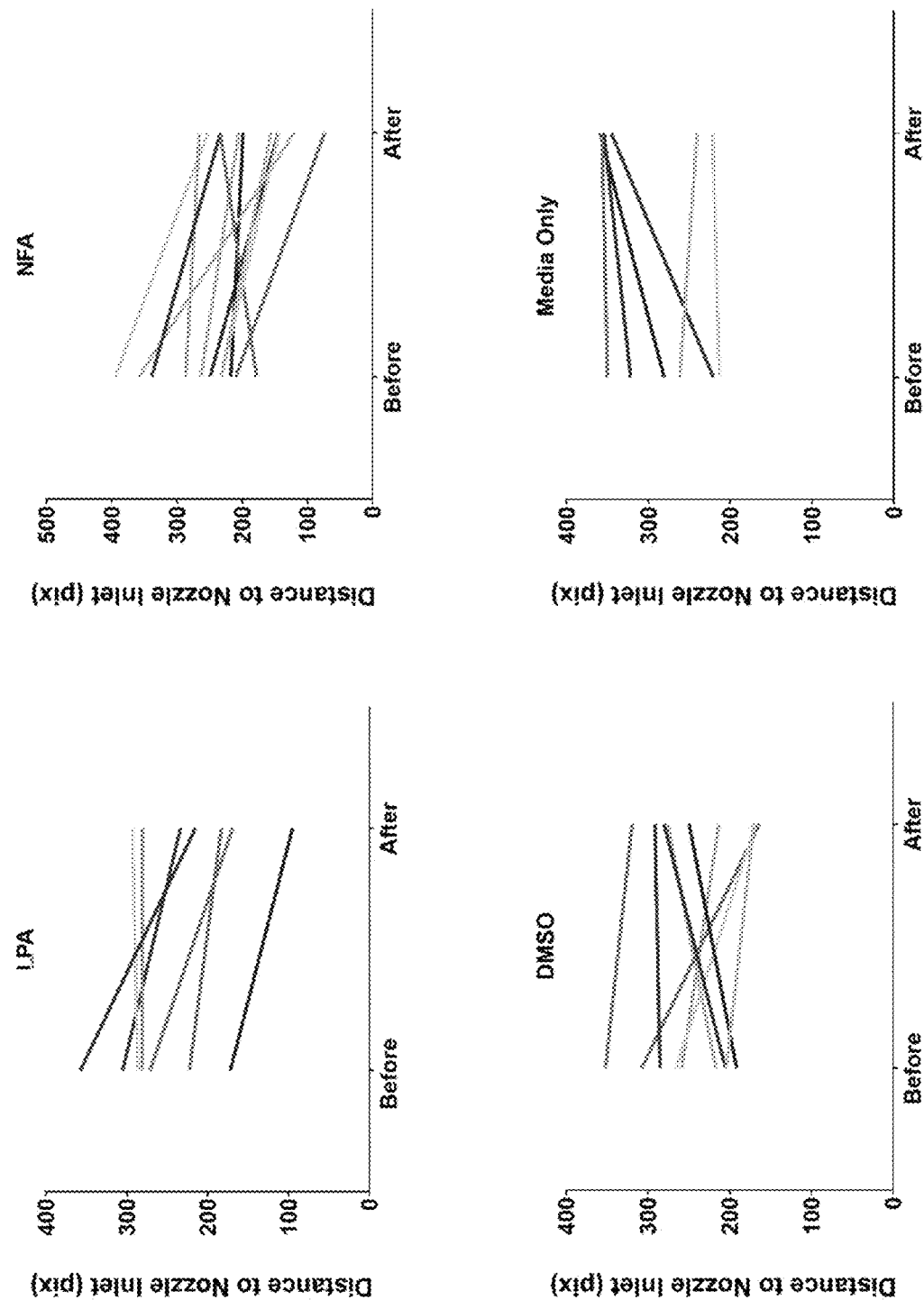
FIG. 10 shows that engrafted cells improve the swimming performance in mutant zebrafish. Swimming performance in sapje-like (sap$^{c/100}$) fish, a dystrophin mutant representing human Duchenne's muscular dystrophy, was assessed before and after transplantation with LPA (top left), NFA (top right), or DMSO (bottom left) treated muscle progenitor cells. Sham (media) treated fish are shown in the bottom right.

The functionality of the engrafted muscle cells was evaluated by swimming performance of sapje-like fish before and after transplantation of muscle progenitor cells. The sapje-like (sap$^{c/100}$) fish, a dystrophin mutant and an excellent model representing human Duchenne's muscular dystrophy, demonstrates symptoms of muscle degeneration. However, recipient fish transplanted with NFA- or LPA-treated cells exhibited better swimming performance and improved swimming ability against a water current, as compared to fish engrafted with control DMSO vehicle treated cells (FIG. 10).

Overall, the success of this cross-species approach to uncovering conserved pathways regulating muscle regeneration suggests new opportunities for treating muscle disease by enhancing myogenic contributions of transplanted and endogenous muscle progenitors.

Example 2

This Example both re-presents certain data from Example 1 and provides additional data.

Stem cell transplantation presents a potentially curative strategy for genetic disorders of skeletal muscle, but this approach is limited due to the deleterious effects of cell expansion in vitro and poor engraftment efficiency. In an effort to overcome this hurdle, it was sought to identify molecular signals that enhance the myogenic activity of cultured muscle progenitors. Here, it is reported that the development and application of a cross-species small molecule screening platform employing zebrafish and mouse, which enables rapid, direct evaluation of the effects of chemical compounds on the engraftment of transplanted muscle precursor cells. Using this system, a library of bioactive lipids was screened to identify those that could increase myogenic engraftment in zebrafish and mice. These efforts identified two lipids, lysophosphatidic acid (LPA) and niflumic acid (NFA), both linked to activation of intracellular calcium ion flux, which showed conserved, dose-dependent and synergistic effects in promoting muscle engraftment across these vertebrate species.

More specifically, a novel screening approach was devised that combines the ability to rapidly and cost-effectively assess the impact of defined chemical compounds on the engraftment efficiency of muscle progenitors in vivo in zebrafish. Next, these compounds were validated using mouse muscle satellite cells (Cerletti et al., 2008; Sherwood et al., 2004). The throughput and accessibility of this model allowed evaluation of 188 compounds sourced from the ICCB Known Bioactives Library, focusing primarily on lipid mediators, a relatively understudied class of biomolecules that can play key roles in enhancing cell migration and promoting regenerative function (Li et al., 2015; Oh et al., 2016). These efforts identified two small molecules, lysophosphatidic acid (LPA) and niflumic acid (NFA), which increased the engraftment efficiency and muscle-forming activity of transplanted myogenic progenitors in both zebrafish and in mice. RNA sequencing and calcium ion imaging studies further revealed that both compounds alter the expression patterns of ion transport genes and increase intracellular calcium concentrations, suggesting that the effects of these lipids are mediated via regulation of calcium-dependent second messenger systems (Berridge et al., 2000). Finally, supporting the potential translational relevance of these compounds, improved physiologic function in swimming performance tests of dystrophic zebrafish (Guyon et al., 2009) transplanted with NFA-treated or LPA-treated muscle precursors was documented.

The novel cross-species approach developed in this study has uncovered previously unknown inducers of skeletal muscle cell engraftment and suggests new potential opportunities for muscle cell therapy as a treatment option for degenerative muscle disorders.

Results

Establishing transplantation parameters for zebrafish muscle cells using a limiting dilution assay.

Figure 11A:
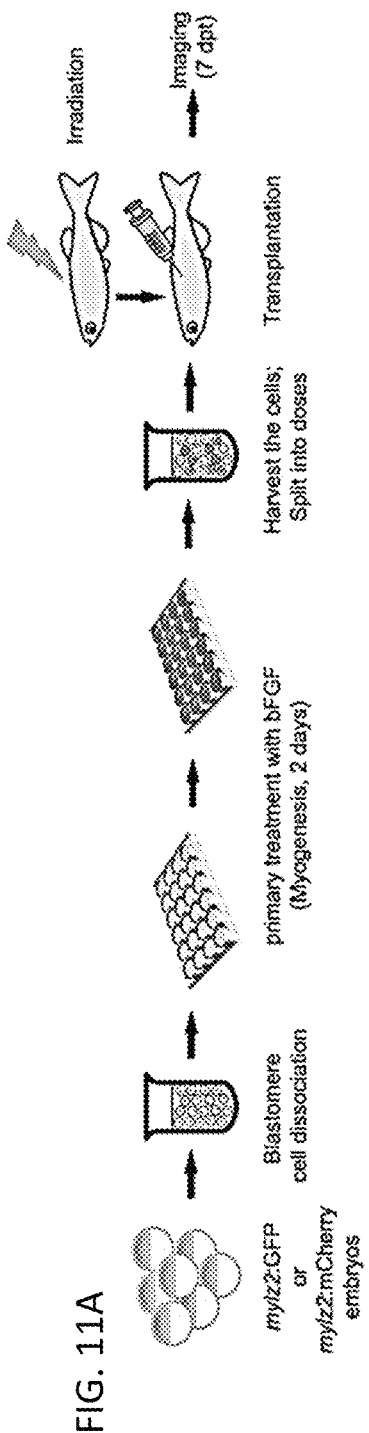
Figure 11C:
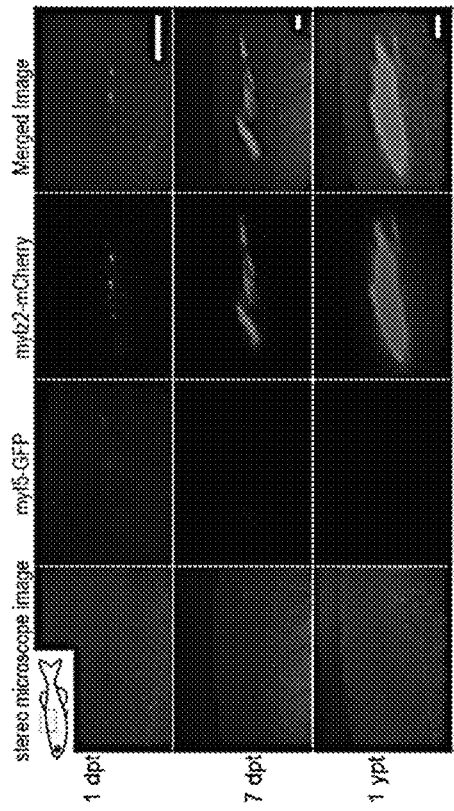
Figure 11B:
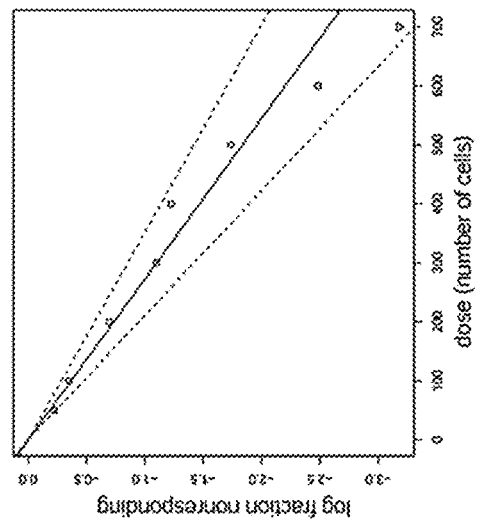
Figure 11D:
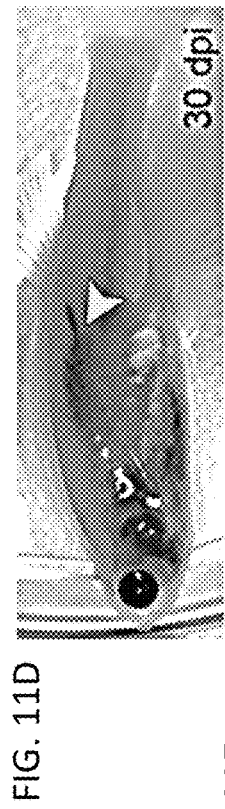
Figure 17:
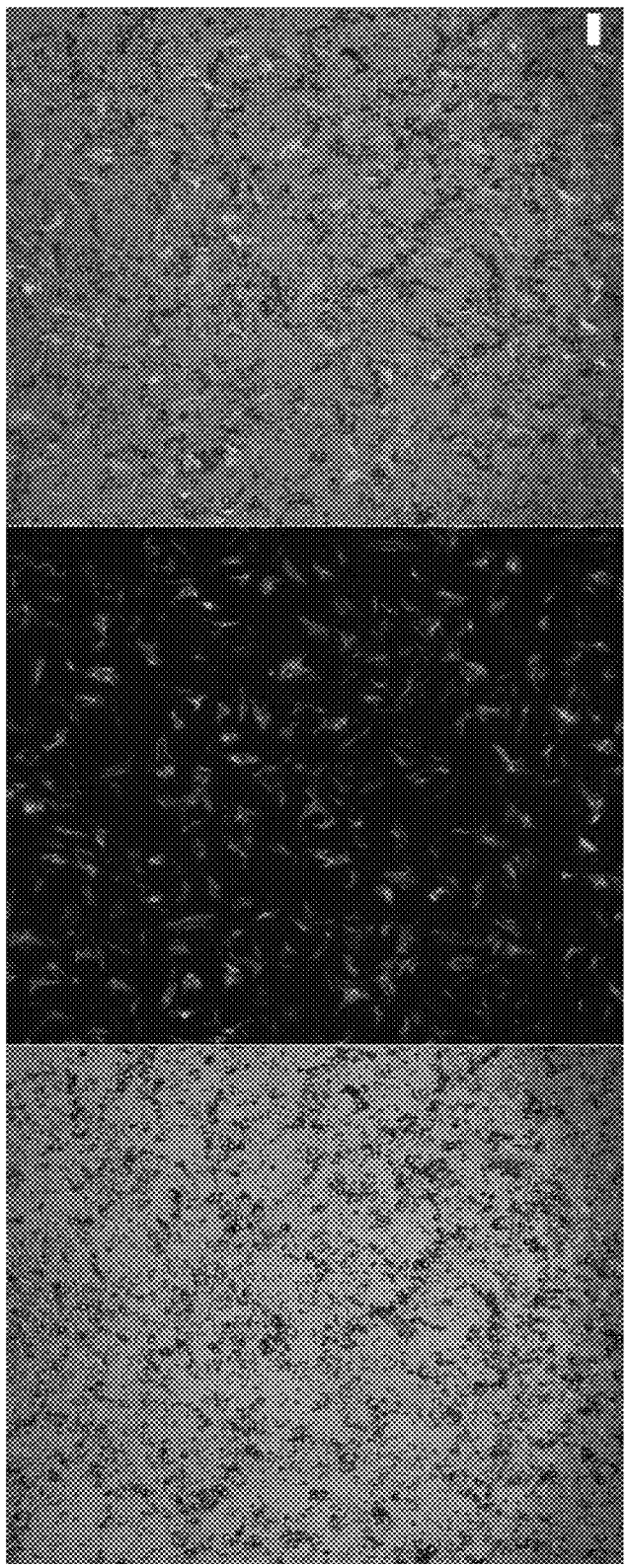
FIG. 17 shows Zebrafish in vitro expanded muscle cells. The mylz2-GFP transgenic line identifies myotubes in developing zebrafish embryos and in vitro expanded muscle cells. Myosin light polypeptide chain 2 (Mylz2, green). Scale bar 200 µm.

Zebrafish myogenic progenitor cells (ZeMPCs) were generated by in vitro culture of blastomeres from mylz2-GFP (FIG. 17) or mylz2-mCherry zebrafish embryos by adaptation of published protocols (Xu et al., 2013), with mylz2 serving as a marker of terminally differentiated muscle cells marker (Ju et al., 2003). ZeMPCs were transplanted into the flank muscles on both sides of transparent casper zebrafish recipients (FIG. 11A). The optimal number of transplanted cells for screening was determined by performing an extreme limiting dilution analysis (ELDA) (Hu and Smyth, 2009) for engraftment. At 7 days post-transplantation (dpt), engraftment success was assessed by in vivo fluorescent stereo microscopy to detect GFP or mCherry-tagged donor-engrafted myofibers in the recipient fish. Notably, persistence of donor-engrafted muscle cells was observed in recipient fish for up to one-year post-transplantation (FIGS. 11C and 11D). These initial studies yielded a 100% successful engraftment rate in fish receiving 700 ZeMPCs, and a 30% successful engraftment rate in fish receiving 100-cell transplants (Table 2). Using ELDA software (Hu and Smyth, 2009), it was calculated that 1 out of 272 ZeMPCs produced under these conditions successfully engrafted, with a 95% confidence interval of 1 out of 211 to 352 in vitro expanded ZeMPCs (FIG. 11B). However, it is noted that the ELDA-determined frequency of engrafting cells varies slightly across different ZeMPC derivations, likely due to subtle fluctuations in the efficiency or expansion of these embryo-derived cells in culture. To account for this, independent ELDA assessments for both experimental and control conditions was included in each subsequent transplantation experiment and always used the same freshly derived ZeMPCs for the different treatment groups within an individual experiment.

TABLE 2

Limiting dilution data showing the frequency of transplanted ZeMPCs, tested fish, responses and calculated engraftment efficiency for ELDA.

| Dose (Number of Transplanted Cells) | Tested (Total Number of Transplanted fish) | Response (Total Number of Engraftment) | Engraftment Efficiency (%) |
| --- | --- | --- | --- |
| 50 | 5 | 1 | 20% |
| 100 | 17 | 5 | 29% |
| 200 | 16 | 8 | 50% |
| 300 | 15 | 10 | 67% |
| 400 | 17 | 12 | 71% |
| 500 | 17 | 14 | 82% |
| 600 | 12 | 11 | 92% |
| 700 | 12 | 12 | 100% | myf5-expressing myogenic progenitors exhibit superior engraftment efficiency.

Figure 11F:
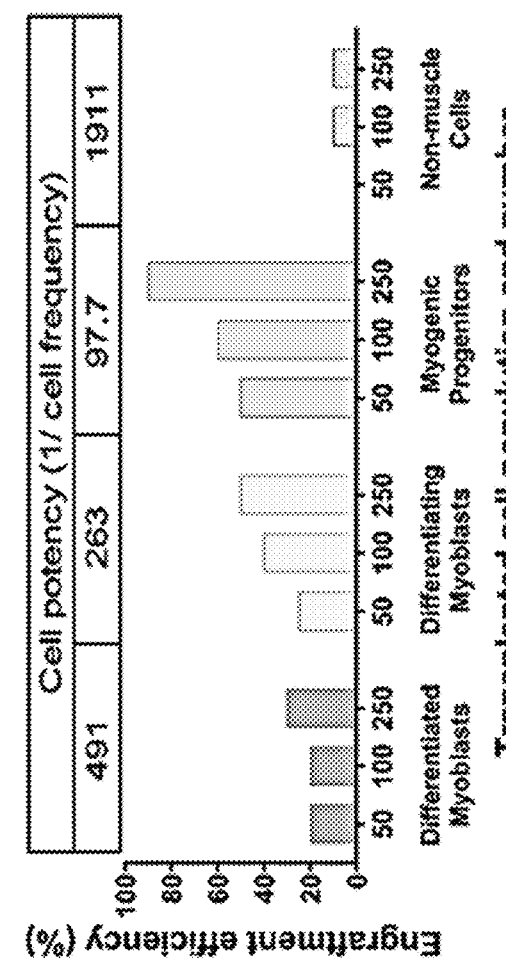
Figure 11E:
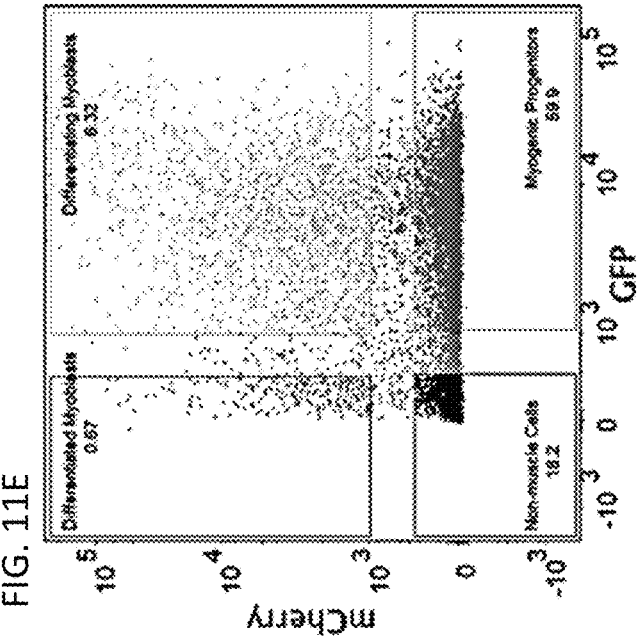

To define the myogenic cell sub-population(s) that supports high efficiency engraftment in zebrafish muscle, myf5-GFP; mylz2-mCherry double transgenic embryos were generated, dissociated, and cultured with bFGF. The in vitro expanded muscle cells at Day 2 were purified into 4 populations of cells by fluorescence-activated cell sorting (FACS): myf5-GFP+mylz2-mCherry–cells, myf5-GFP–mylz2-mCherry+cells, myf5-GFP+mylz2-mCherry+cells, and myf5-GFP–mylz2-mCherry– cells (FIG. 11E). Based on their myogenic marker expression, these sorted cells represent myogenic progenitors, terminally differentiated muscle cells, differentiating myoblasts, and other non-muscle cell types, respectively. Cells from each sorted population were transplanted intramuscularly into 10 individual casper recipients at each of 3 doses—50 cells, 100 cells, and 250 cells—to enable limiting dilution analysis. At 7 dpt, fish were anesthetized and prepared for imaging. The engrafting cell frequency was highest for myf5-GFP+ mylz2-mCherry–cells (1 out of 97.7), indicating that myogenic progenitor cells engrafted more readily relative to the other populations evaluated (FIG. 11F).

Transplanted embryo-derived zebrafish muscle cells fuse with recipient muscle cells.

Figure 18A:
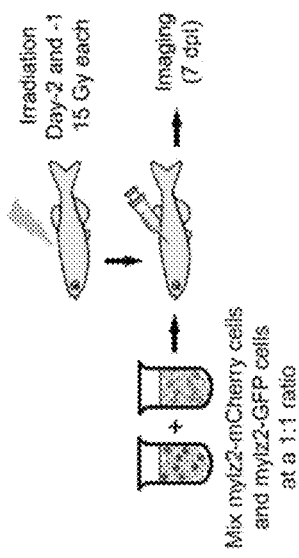
FIGS. 18A-18C show in vivo fusion of donor muscle cells together.
Figure 18B:
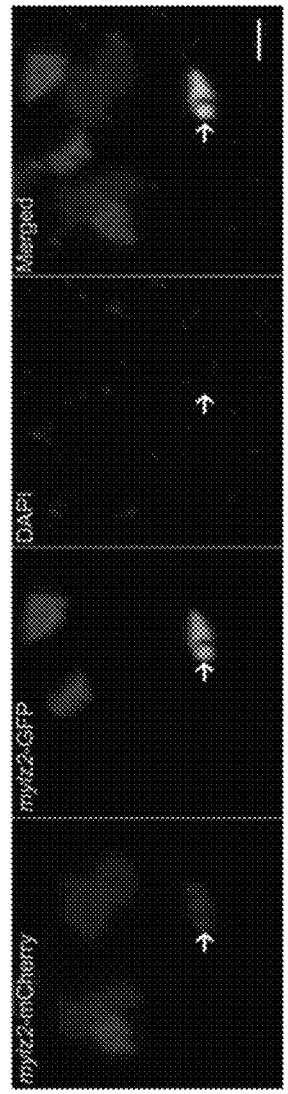
Figure 18C:
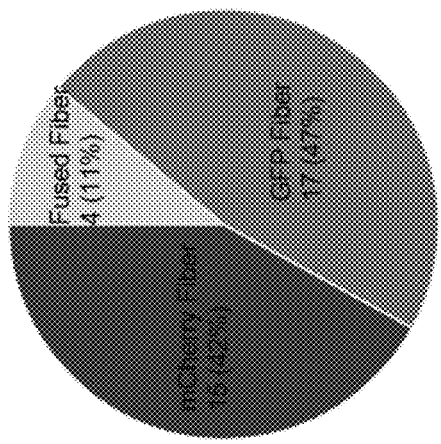

To determine the manner by which transplanted donor ZeMPC cells contribute to muscle regeneration in vivo, whether by de novo myogenesis or by fusion with endogenous myocytes, 1 million in vitro generated muscle cells from mylz2-GFP embryos were transplanted into mylz2-mCherry adult fish (FIG. 11H). At 7 dpt, the recipient fish were euthanized, and the dissected muscle was fixed, sectioned, stained with DAPI, and prepared for imaging to discriminate donor-derived (GFP+), host-derived (mCherry+) and hybrid (GFP+ and mCherry+) muscle cells. A cross section of one recipient fish flank shows both mylz2-mCherry-tagged recipient muscle cells and mylz2-GFP-tagged donor cells (FIG. 11I). Although the cells at the center of the engrafted patch express only GFP, cells at the border are marked with both GFP and mCherry (FIG. 11I, bottom row), indicating that the transplanted muscle cells are capable of both de novo myogenesis and fusion with recipient muscle. To further test the in vivo fusion capacity of transplanted donor cells, in vitro expanded muscle cells from mylz2-mCherry embryos and mylz2-GFP embryos were mixed prior to transplant at a 1:1 ratio and then immediately transferred into casper recipients (FIG. 18A). At 7 dpt, the recipients were euthanized, and the dissected muscle was fixed, sectioned, stained with DAPI, and prepared for imaging. A cross section of the recipient fish flank shows both mylz2-mCherry and mylz2-GFP single-color fibers, as well as double-positive (mylz2-mCherry and mylz2-GFP) hybrid fibers (FIG. 18B). In this experiment, single-color fibers were equivalently distributed among GFP-positive (47%) and mCherry-positive (42%) fibers, with 11% of fibers exhibiting both GFP and mCherry, a clear demonstration of the fusogenic ability of transplanted donor cells (FIG. 18C).

Figure 12A:
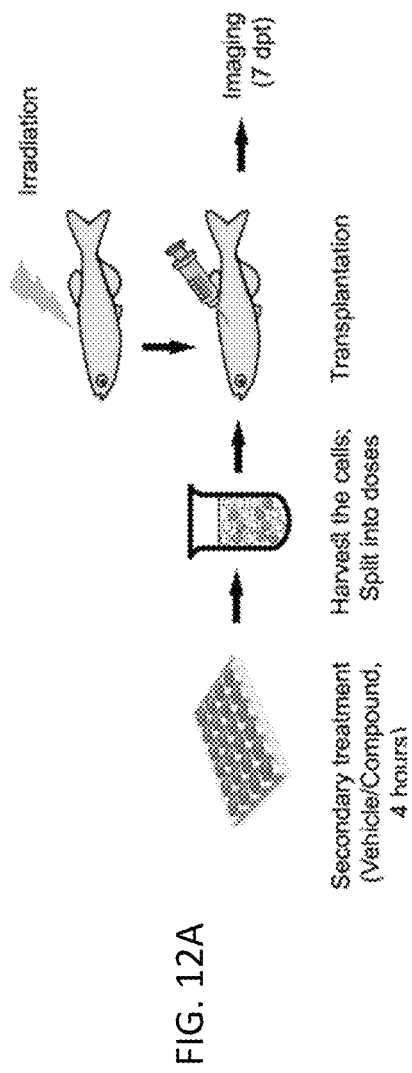
FIGS. 12A-12D shows that ex vivo exposure to NFA or LPA enhances the engraftment efficiency of zebrafish muscle cells in vivo.
Figure 12B:
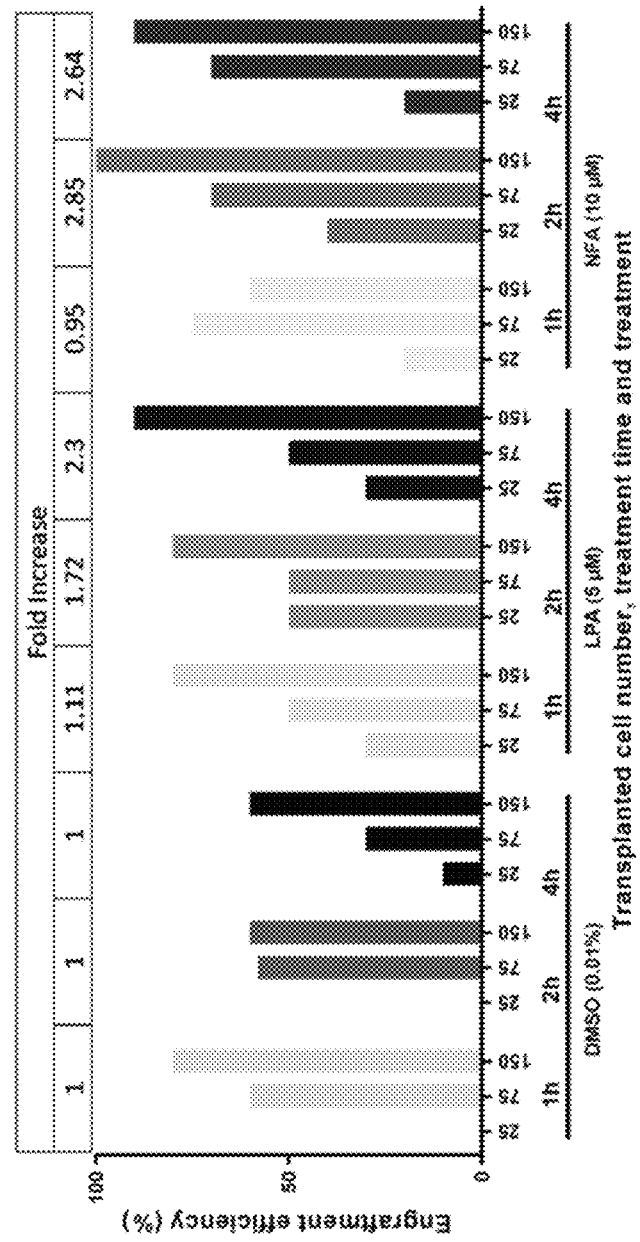
Figure 20A:
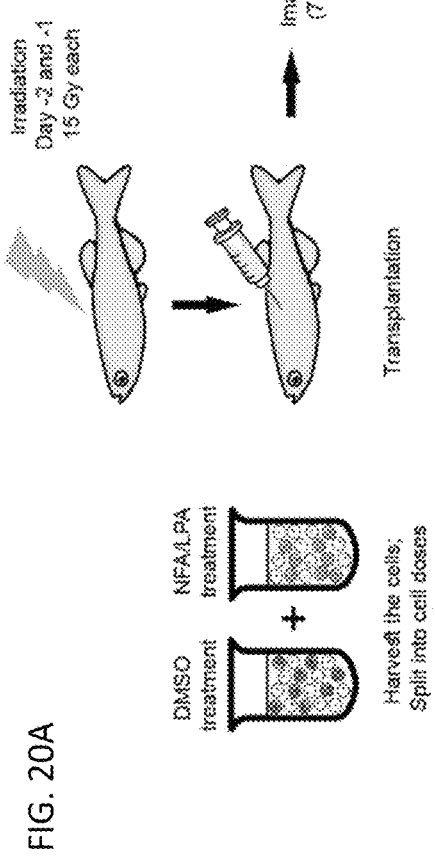
FIGS. 20A-20B show ZeMPC competitive transplantation assays results.
Figure 20B:
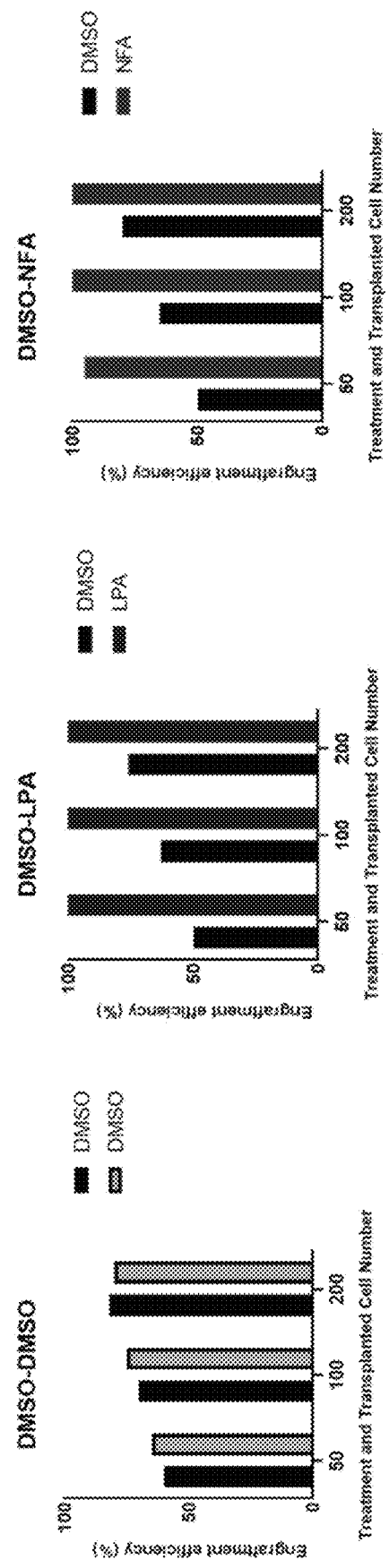

Screening for Compounds that Improve Myogenic Progenitor Cell Engraftment Efficiency Lipids are frequently found to enhance cell migration and homeostasis in blood and muscle tissue (Cencetti et al., 2014; Lahvic et al., 2018; Li et al., 2015; Oh et al., 2016), and so it was elected to screen mainly bioactive lipids in efforts to identify compounds that enhance ZeMPCs engraftment efficiency in vivo. Myogenic progenitor cells were treated for 4 hours with one of the 188 unique lipid compounds contained in the ICCB Known Bioactives Library. Compound-treated cells were then harvested and transplanted intramuscularly into both flanks of 5 different casper recipient fish, with transplants performed at each of 3 transplanted cell doses (25, 75 or 150 cells). In these studies, recipient fish received split-dose irradiation of 15 Gy at 2 days and 1 day prior to transplantation to suppress any immune responses to the transplanted cells. Engraftment efficiency was measured by imaging casper recipients at 7 dpt (FIG. 18A). Any compounds that increased engraftment efficiency (ELDA-calculated cell potency) by at least 2 times that of the simultaneously assessed control group were further evaluated using an irradiation-free transplantation model (Moore et al., 2016). For this secondary screening approach, cells were transplanted into prkdc$^{D3612fs}$ casper fish, which are deficient in mature T and B cells, and assayed engraftment efficiency in the recipient fish 7 days post-transplantation. Two compounds were identified, lysophosphatidic acid (LPA) and niflumic acid (NFA), which increased ZeMPC engraftment efficiency in both of these assay systems (FIG. 12B). Both of these compounds also increased ZeMPC engraftment efficiencies in competitive transplantation assays, with compound-treated cells showing an approximate 2-fold advantage as compared to DMSO-treated control cells (FIG. 20A-20B).

Dose Titration of NFA and LPA for Enhancing Myogenic Progenitor Cell Engraftment Efficiency To further assess the effects of LPA and NFA on ZeMPC engraftment efficiency, cells were treated with each compound for different durations and at different concentrations.

Figure 12C:
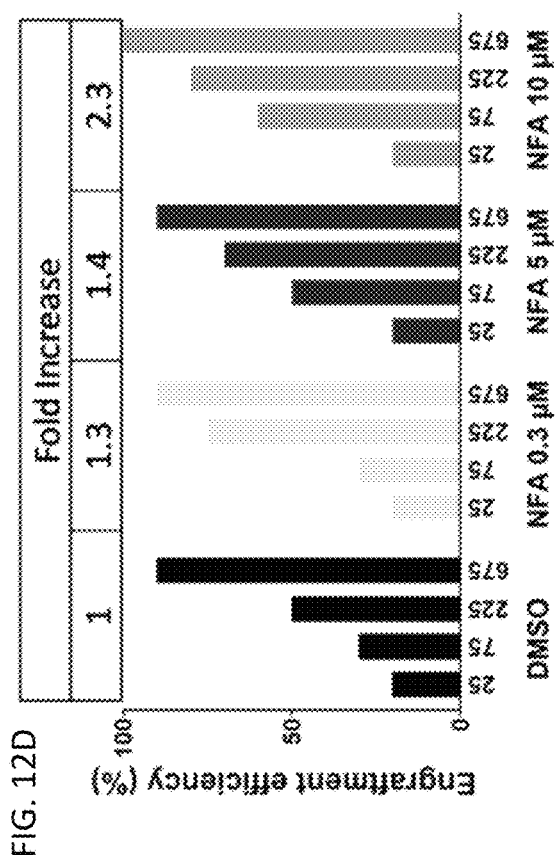
Figure 12D:
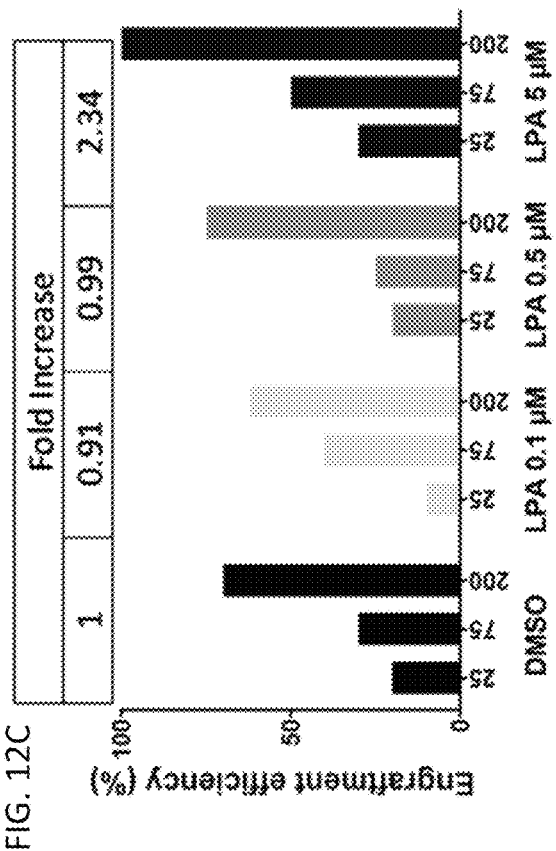
Figure 19:
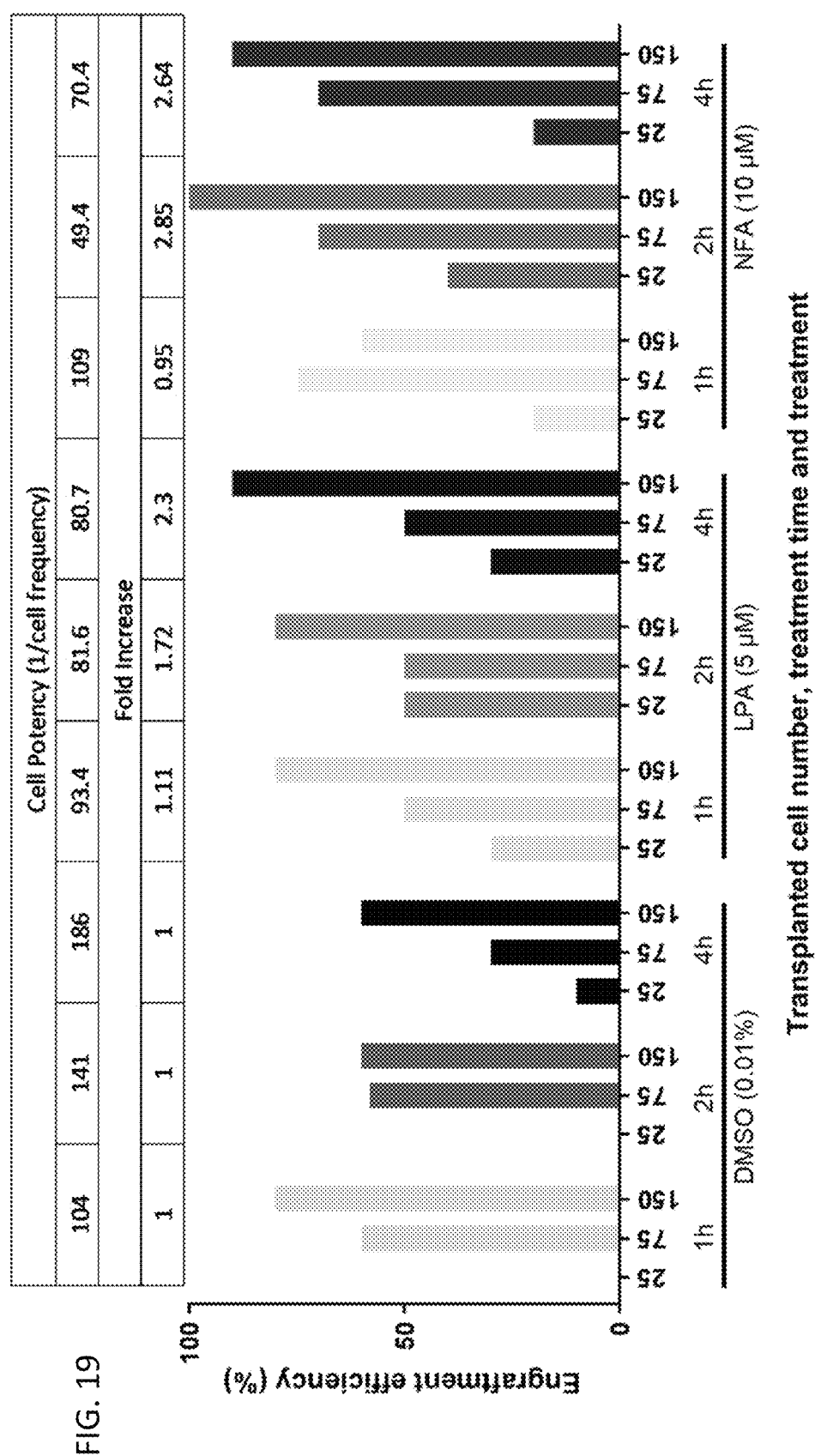
FIG. 19 shows NFA and LPA treatments enhance the engraftment efficiency of zebrafish muscle cells in vivo. The purpose of the LDA is to test whether the different treatments have the same engrafting cell proportions. Using ELDA software the treated cell potency, which indicates the number of transplanted cells required for engraftment (top table), was measured. Fold increase of the engraftment efficiency was calculated as the ratio of the LPA- or NFA-treated cell potency and DMSO-treated cell potency; Fold increase of the engraftment efficiency describes how much the engraftment efficiency changed in comparison to the experimental control group (DMSO) for 1, 2, and 4 hours of LPA/NFA treatment in comparison to 1, 2, and 4 hours of DMSO treatment, respectively (bottom table).

Longer DMSO treatment time resulted in lower engraftment efficiency, where 1 out of 104, 141, and 186 transplanted cells were engrafted after 1, 2, and 4 hours of DMSO treatment, respectively (FIG. 19). These data suggest that under control conditions, ZeMPCs lose engraftment potential during prolonged in vitro incubation. In contrast, LPA-treated ZeMPCs showed progressively increased engraftment efficiency, over time and at each experimental time point, when compared to control. Treatment of ZeMPCs for 1, 2 or 4 hours with LPA increased the engraftment efficiency to 1.11, 1.72 and 2.3 times that of DMSO-treated cells, respectively (FIG. 12B). Similarly, while one-hour NFA-treatment did not alter ZeMPC engraftment, engraftment efficiencies were increased to 2.85 and 2.64 times higher than did DMSO-treated cells after 2 or 4 hours of treatment, respectively (FIG. 12B). engraftment efficiencies of cells treated with different concentrations of DMSO (as vehicle control), LPA, or NFA (FIGS. 12C and 12D) were also tested. Treatment of ZeMPCs with 5 µM LPA or 10 µM NFA yielded the highest engraftment efficiencies relative to vehicle-treated controls—2.34 times higher engraftment efficiency with 5 µM LPA treatment and 2.37 times higher engraftment efficiency with 10 µM NFA treatment. Treatment with 0.1 µM LPA or 0.3 µM NFA did not alter the engraftment efficiency of the treated cells (FIGS. 12C and 12D). Together, these data confirm the positive effects of both LPA and NFA on engraftment by ZeMPCs and indicate the optimal treatment time (4 hours) to drive robust in vivo myogenic contributions from transplanted cells treated with these compounds.

NFA and LPA have Additive Effects on Engraftment Efficiency

Figure 13:
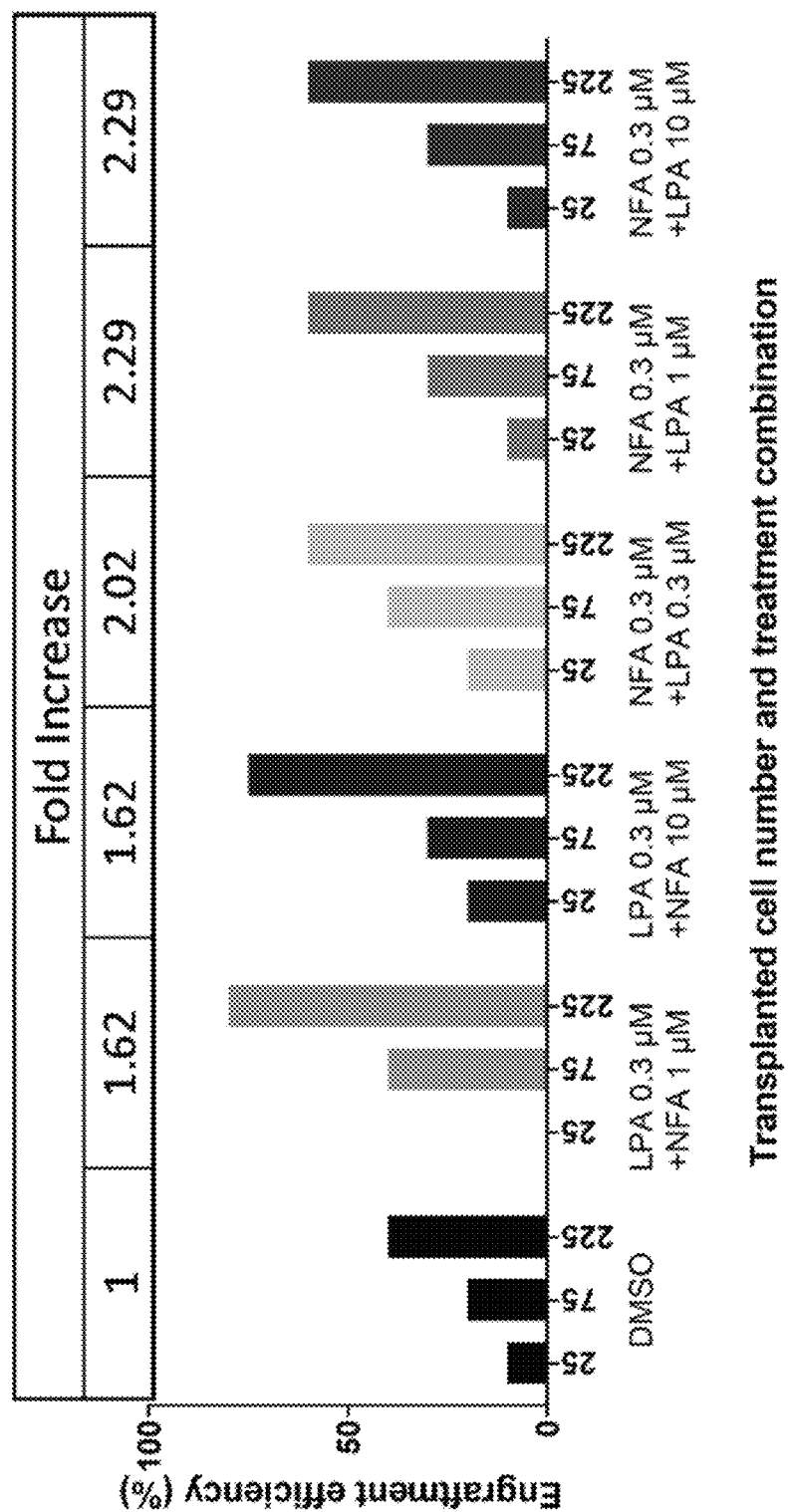
FIG. 13 shows that NFA and LPA have an additive effect on muscle progenitor cell engraftment efficiency in zebrafish. Engraftment efficiency in prkdc-mutant recipient zebrafish (4- to 8-months-old) of ZeMPCs treated for 4 hours with the indicated concentrations and combinations of NFA and LPA, or with DMSA (vehicle) as control. Fold increase of the engraftment efficiency was calculated as the ratio of the LPA and NFA combo-treated cell potency and DMSO-treated cell potency.

To determine whether a combination of NFA and LPA might show additive or synergistic effects on ZeMPC engraftment efficiency, different concentrations of NFA and LPA were combined for pre-transplantation treatment. Using the limiting dilution assay described above, it was found that treatment with 0.1 µM LPA, a concentration equivalent to serum LPA levels in human (Michalczyk et al., 2017), did not result in any change in ZeMPC engraftment efficiency. Engraftment of myogenic progenitors treated with 0.3 µM NFA similarly showed no difference in engraftment rate compared to that of vehicle-treated controls. However, cells treated with either 0.3 µM LPA in combination with 1 µM or 10 NFA, or with 0.3 µM NFA in combination with 0.3 µM or 10 µM LPA, showed 1.6- to 2.3-fold higher engraftment efficiencies relative to the experimental control (FIG. 13). Indeed, exposure to 0.3 µM NFA combined with 0.3 µM LPA nearly doubled engraftment efficiency compared to vehicle alone, while treatment with the same concentrations of these compounds individually had minimal effects (see FIG. 12). These data suggest that NFA and LPA have additive effects on myogenic progenitor activity, since combination of NFA and LPA at concentrations that are ineffective individually increases ZeMPC engraftment efficiency.

NFA and LPA Treatment Increase Mouse Satellite Cell Engraftment Efficiency

Figure 14A:
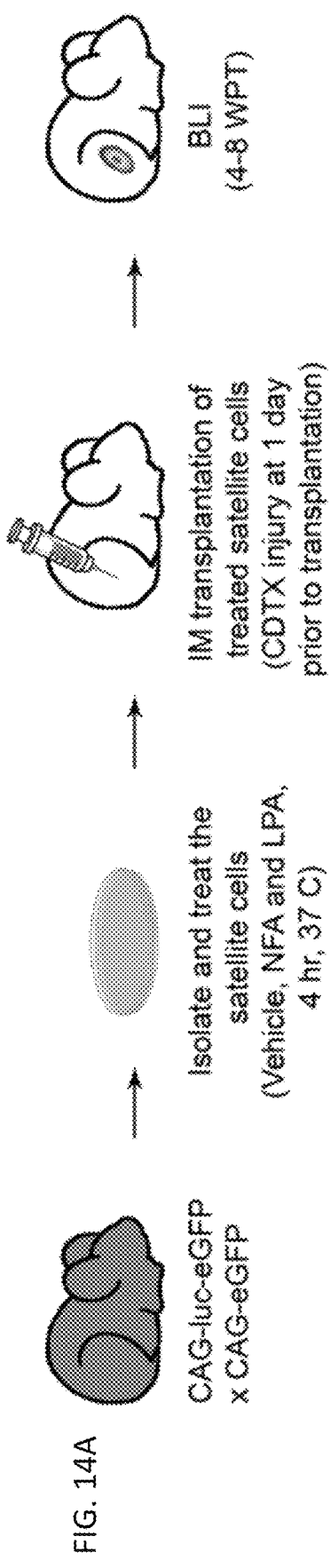
FIGS. 14A-14D show that NFA and LPA treatments enhance the engraftment efficiency of mouse satellite cells.
Figure 14C:
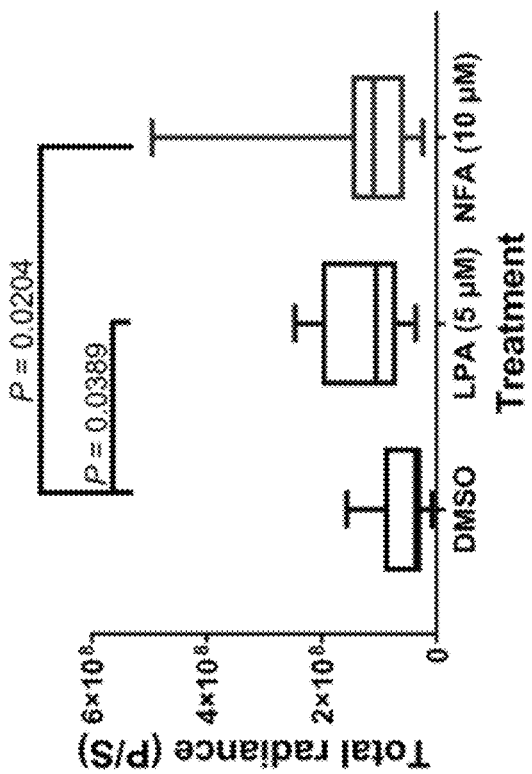
Figure 14B:
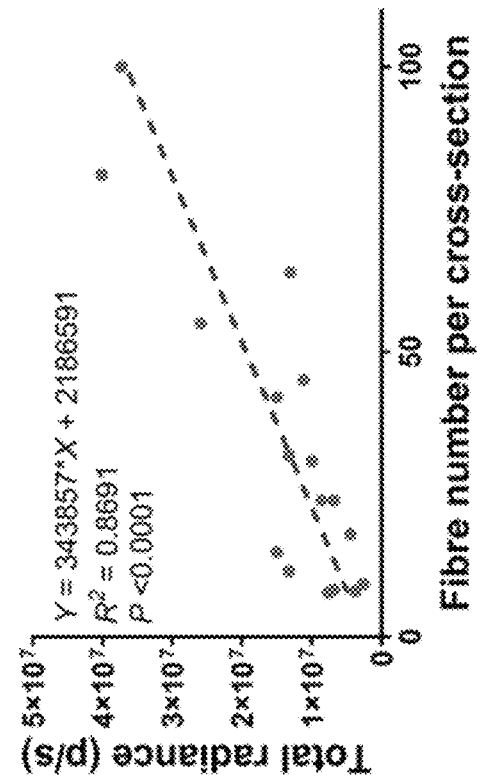

To test whether the effects of NFA and LPA on myogenic progenitor cell engraftment potential might be conserved across vertebrate biology, the effects of these compounds on mouse satellite cells transplanted into pre-injured recipient tibialis anterior (TA) muscles were next assessed. Satellite cells were isolated as CD45-Sca1-Mac1-CXCR4+β1-integrin+myofiber-associated cells (Castiglioni et al., 2014; Cerletti et al., 2012; Cerletti et al., 2008; Maesner et al., 2016; Sherwood et al., 2004; Sinha et al., 2014; Xu et al., 2013) from FVB-Tg(CAG-luc,-GFP); FVB-Tg(CAG-GFP) double transgenic mice using a published protocol (Maesner et al., 2016; Sherwood et al., 2004; Xu et al., 2013) (FIG. 14A). Use of these mice as satellite cell donors allows for tracking of muscle engraftment in intact animals, via bioluminescence imaging (BLI) of the luciferase (luc) transgene (Ho et al., 2017), as well as terminal analysis of engrafted fiber number by immunofluorescence for GFP (Cerletti et al., 2008). The BLI approach in particular is ideal for measuring engraftment efficiency in this study because it mirrors this zebrafish transplant system and because it allows sensitive, quantitative detection of engrafted cells with dramatically reduced analysis time compared to typical immunohistological approaches. In addition, the accuracy of this model was validated in initial studies in which recipient FVB mice were pre-injured by injection of cardiotoxin (CDTX), to stimulate a regenerative response (Cerletti et al., 2008), one day prior to intramuscular transfer of 5000 satellite cells. Recipients were then imaged by BLI, and subsequently euthanized to harvest the injected TA muscles. The harvested muscle tissue was fixed and imaged to quantify the number of GFP+ myofibers. A strong correlation ($R^2=0.869$) was observed in these studies between the number of GFP+ myofibers in the recipient TA and the luminescence signal captured via BLI (FIG. 14B). These data further confirm the accuracy of BLI measurements in assessing muscle engraftment efficiencies (Judson et al., 2018; Sacco et al., 2008) and justify the use of BLI as an accurate readout for comparing engraftment efficiencies in mice transplanted with vehicle- or compound-treated cells.

Figure 14D:
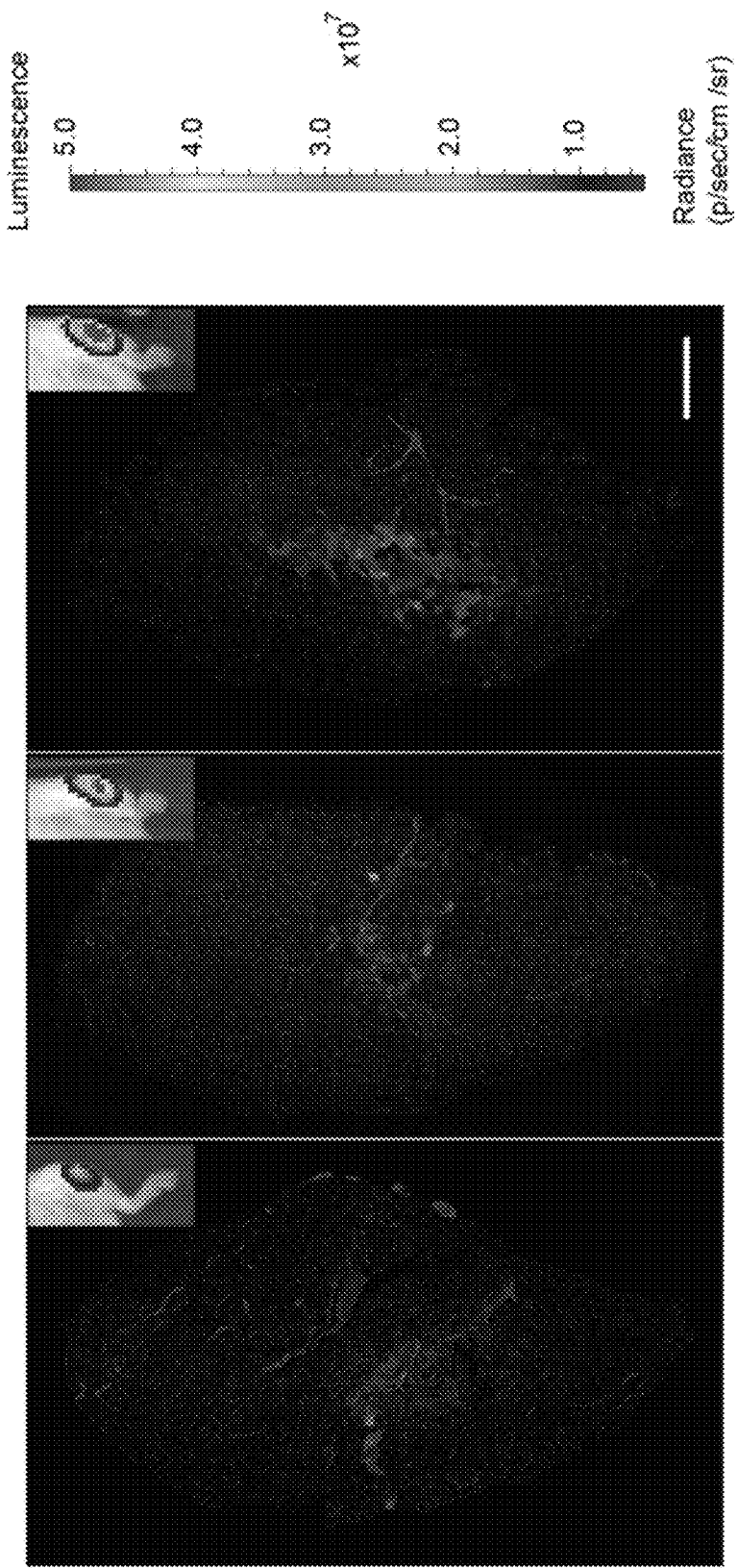

To this end, mouse satellite cells were again sorted from double-transgenic (luc+GFP+) mice and exposed them to NFA, LPA, or vehicle (DMSO) under the optimal dose conditions established using the fish model (see above; 4 h. treatment at 37° C. with 10 µM of NFA or 5 µM of LPA), prior to transplant. Compound-treated cells were then recovered and, after washing out the media containing the compounds (NFA, LPA or DMSO), counted and transplanted at 5000 cells per recipient into the pre-injured TA muscles of non-transgenic FVB hosts. The kinetics of muscle engraftment were subsequently assessed by weekly BLI imaging of transplanted limbs. Similar to the fish experiments, both NFA and LPA enhanced the engraftment efficiency of mouse satellite cells in these in vivo transplantation assays (FIGS. 14C and 14D), indicating conserved effects of these pro-myogenic compounds on mammalian muscle precursor cells.

NFA and LPA regulate expression of muscle development and calcium ion-dependent genes.

Figure 15A:
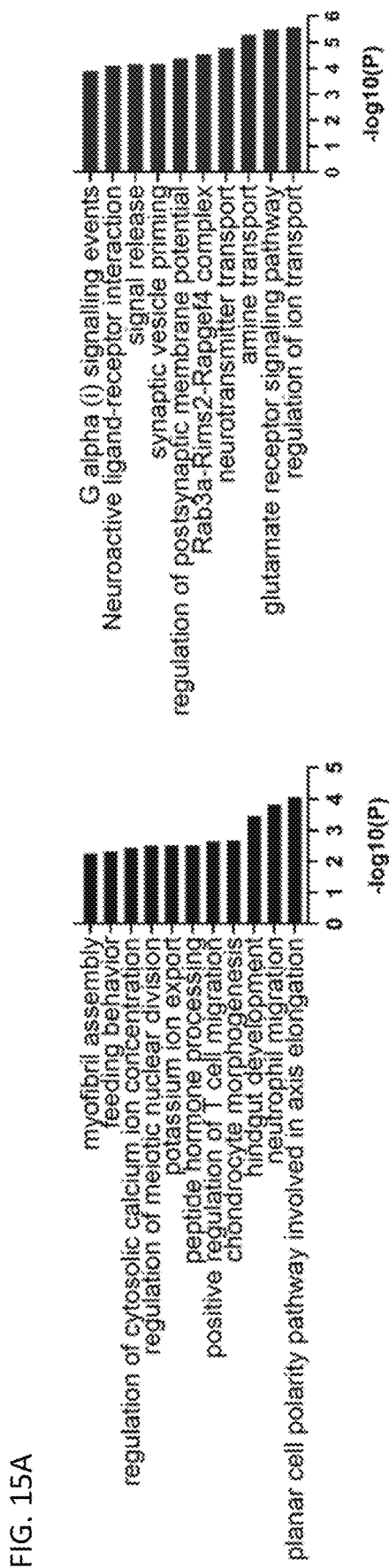
FIGS. 15A-15B show that differential gene expression patterns reveal the upregulation of calcium ion-dependent genes and downregulation of muscle development genes in NFA-treated and LPA-treated mouse satellite cells.
Figure 15B:
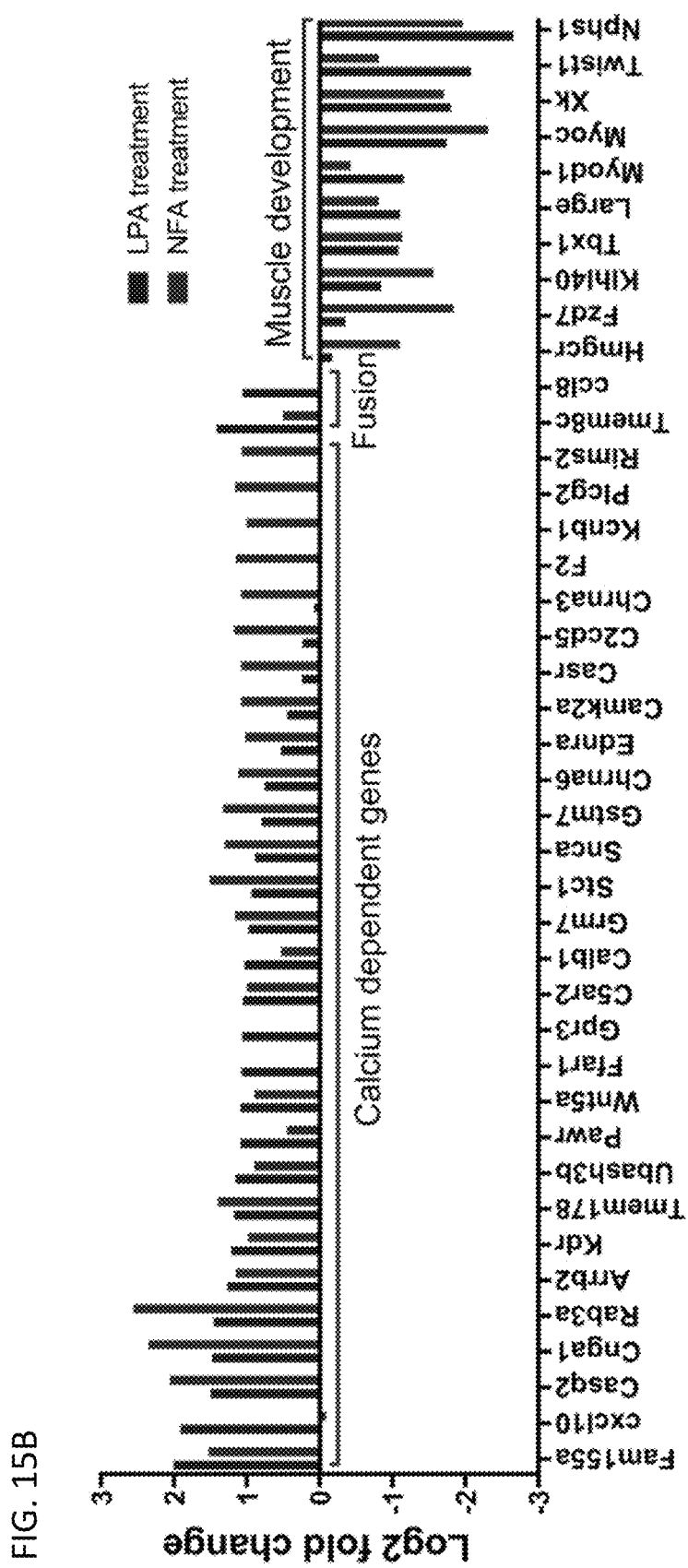

To gain insight into the mechanisms through which LPA and NFA treatment might enhance donor cell engraftment in vertebrate muscle, RNA sequencing analysis were next performed in treated ZeMPCs and in mouse satellite cells. Comparison of differential gene expression in NFA-treated or LPA-treated cells to vehicle-treated cells indicated upregulation of calcium-dependent genes in response to these compounds in both ZeMPCs (FIG. 21) and mouse satellite cells (FIGS. 15A and 15B). Interestingly, treatment of mouse satellite cells with LPA upregulated myoblast fusion related genes, including myomaker (Tmem8c) and Ccl8.

Figure 22:
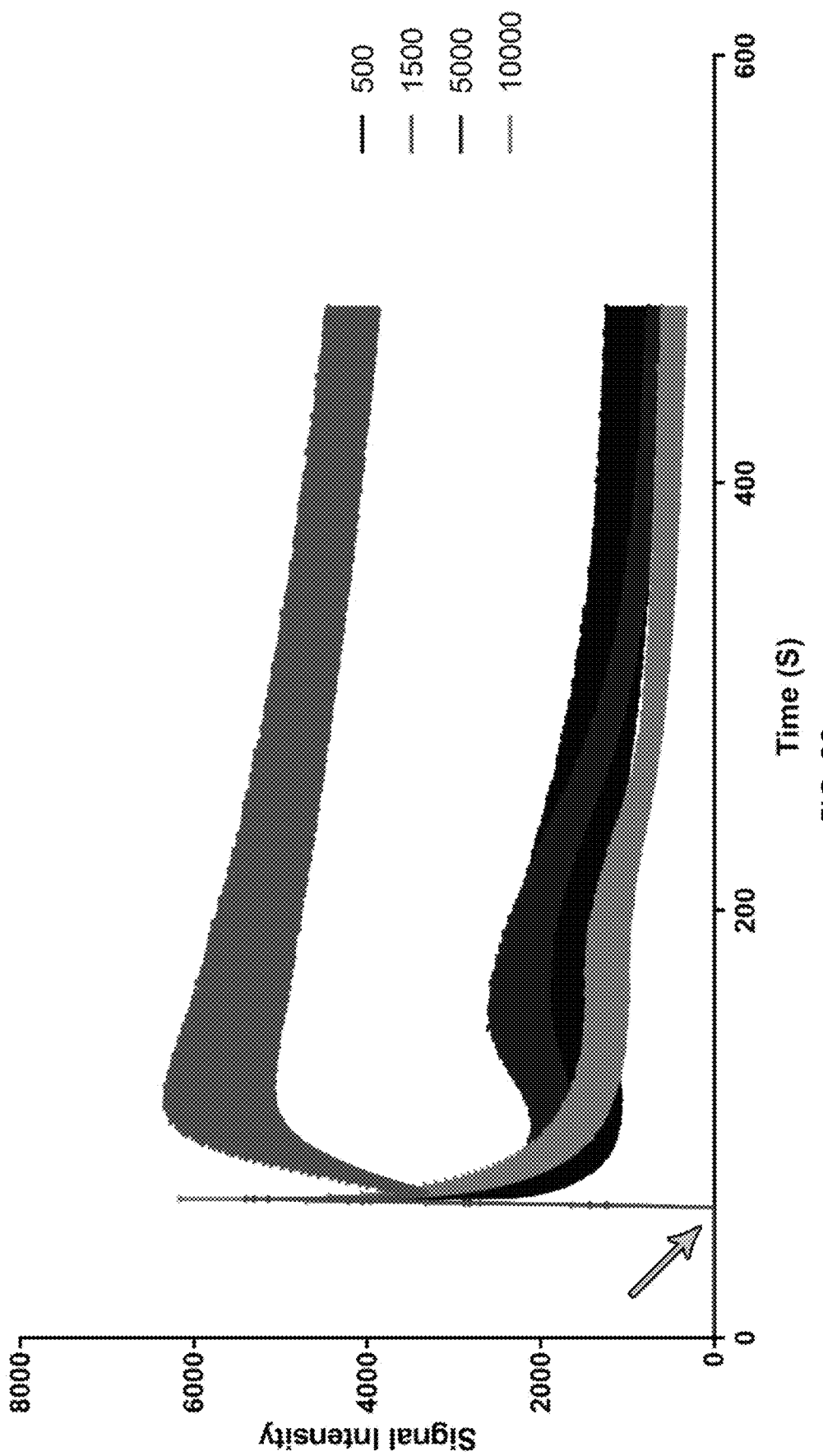
FIG. 22 show satellite cell density optimization for calcium imaging. Signal intensity was measured for different initial cell densities: 10,000 (blue), 5,000 (green), 1,500 (red), and 500 (black) mouse satellite cells, which were seeded in 384 well plate (n=8). The graph reports the signal intensity of the 8 replicates for each cell density. Media containing free calcium ions was added to all wells at the timepoint marked with an arrow. The sorted satellite cells in 384 well plates were incubated with Fluo4 AM for 45 minutes at 37° C., followed by imaging.
Figure 23:
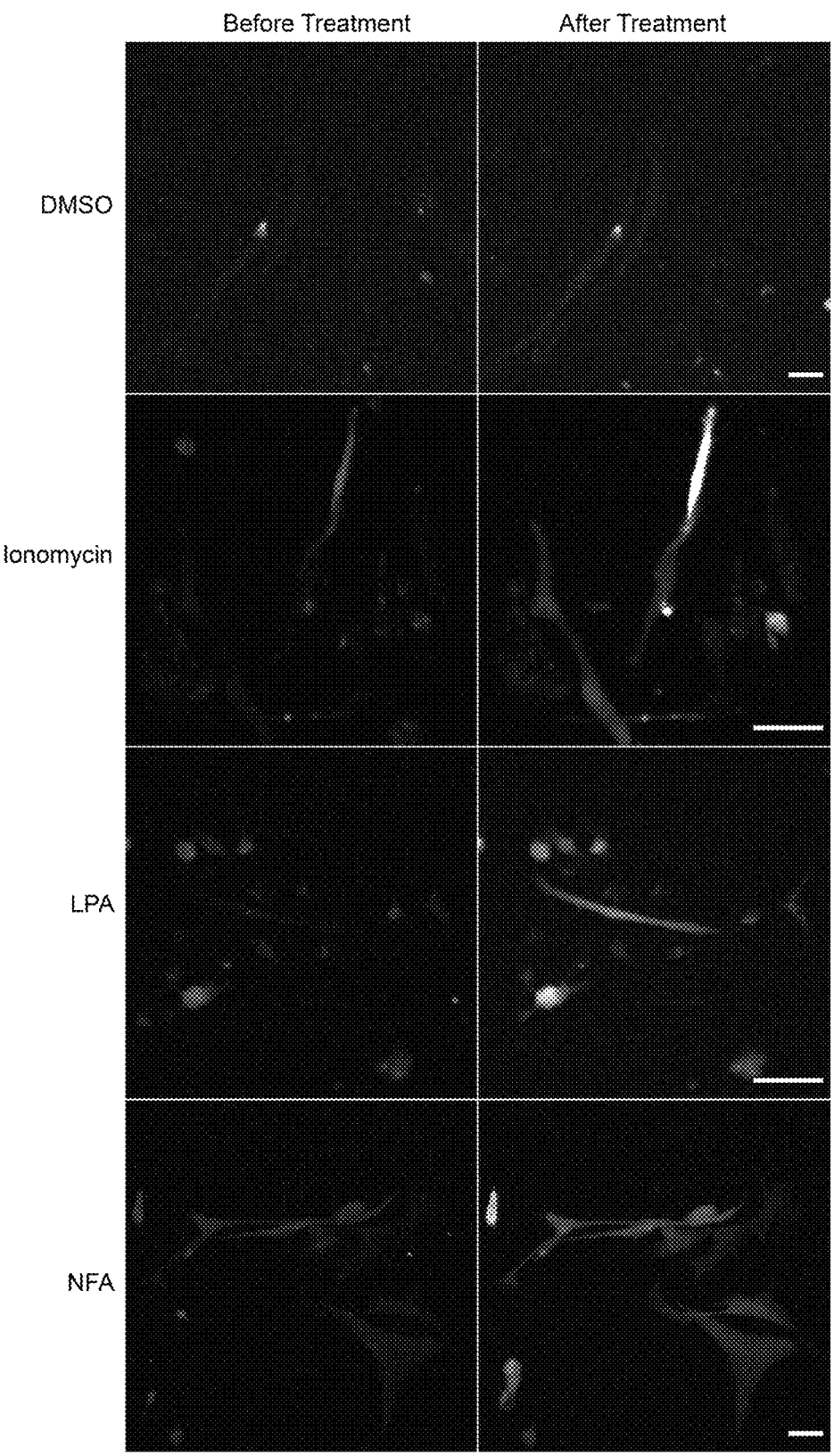
FIG. 23 shows intracellular calcium ion increases in response to NFA and LPA in in vitro expanded zebrafish muscle cells. Fura-2, AM treated ZeMPCs were exposed to 10 µM NFA, 5 µM LPA, 10 µM Ionomycin (as a positive control) and DMSO (as vehicle control) to visualize their effect on intracellular calcium ion concentration using single-cell imaging. Comparing signal intensity before loading the treatment (left column) to signal intensity 10-20 seconds after loading the treatment (right column), reveals NFA, LPA and ionomycin increase the intracellular calcium ion concentration. Scale bar 50 μm.

To further evaluate the possibility, suggested by these transcriptional studies, that NFA and LPA may act on myogenic progenitors by increasing cytosolic calcium ion concentration, mouse satellite cells were isolated for calcium imaging analysis in response to each compound. First, to establish optimal conditions, cells were sorted by FACS into 384 well plates at 10,000, 5,000, 1,500, or 500 cells per well, with 8 replicates for each cell density. Subsequent incubation with Fluo4 AM, a fluorescent calcium ion indicator, for 45 minutes at 37° C., showed maximal signal intensity at a density of 1,500 cells per well (FIG. 22). Based on these results, intracellular calcium ion concentration changes were next assessed in ZeMPCs, in the mouse myogenic cell line C2C12, and in primary mouse satellite cells plated at 1,500/well and exposed to varying doses of NFA and LPA (FIGS. 23, 24 and 25A). Cells were again incubated with Fluo4 AM for 45 minutes at 37° C. followed by imaging. Different concentrations of LPA, NFA, or both compounds combined, along with DMSO (vehicle control) and ionomycin (direct calcium ionophore), were added 60 seconds after the beginning of imaging to quantify both baseline calcium ion concentrations and calcium flux in response to the different treatment conditions. Calcium concentrations were calculated as area under the curve (AUC) of signal intensity and compared these values across different concentrations of each compound (FIG. 25A). Calcium ion concentrations were increased significantly, relative to vehicle-treated controls, in response to 1-5 µM of LPA and 2.5-10 µM of NFA, which, notably, overlaps with the concentrations determined to provide optimal muscle cell engraftment in zebrafish and in mice (5 µM LPA and 10 µM NFA, FIGS. 12 and 25B). The AUC of 0.25 µM NFA combined with 0.25 µM LPA showed a boost in intracellular calcium ion concentration in comparison to the response when each of these drugs was given individually at the same concentrations, correlating with the previously documented additive effect of NFA and LPA on engraftment (FIG. 13). Interestingly, ionomycin, included as a positive control for calcium ion influx in mouse satellite cells, also increased the engraftment efficiency of treated ZeMPCs (FIG. 25B), consistent with a direct, mechanistic role for increased calcium signaling in enhancing the myogenic activity of transplanted muscle progenitors.

Figure 16A:
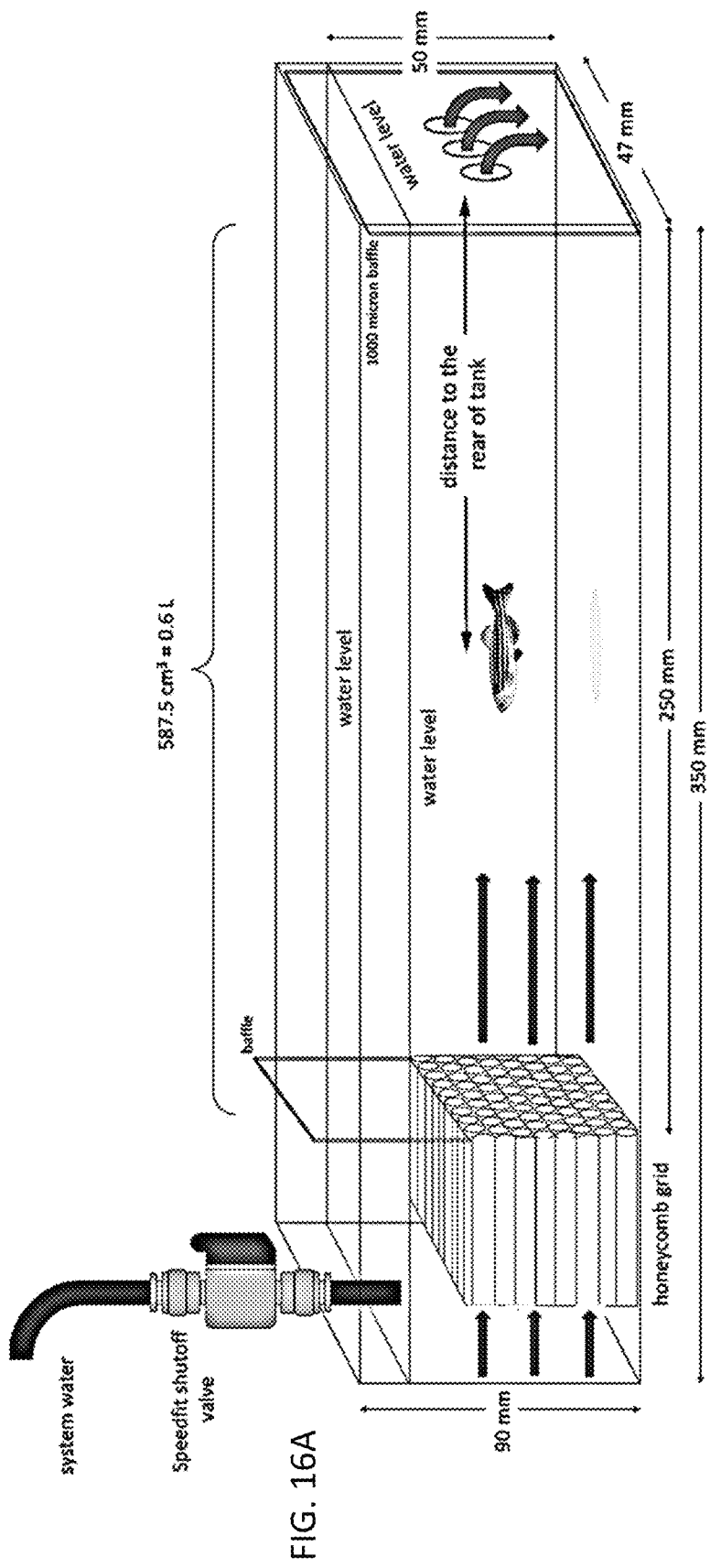
FIGS. 16A-16E show that engrafted cells improve swimming performance in mutant zebrafish.
Figure 16B:
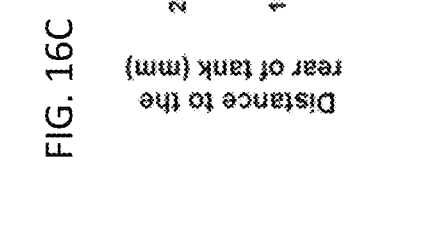
Figure 16C:
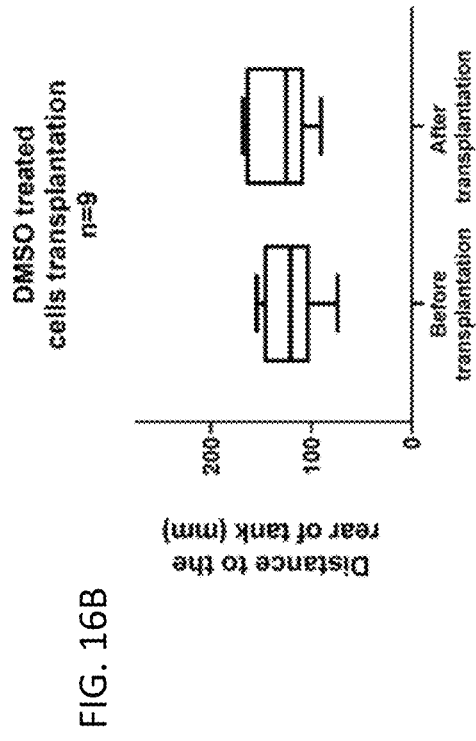
Figure 16D:
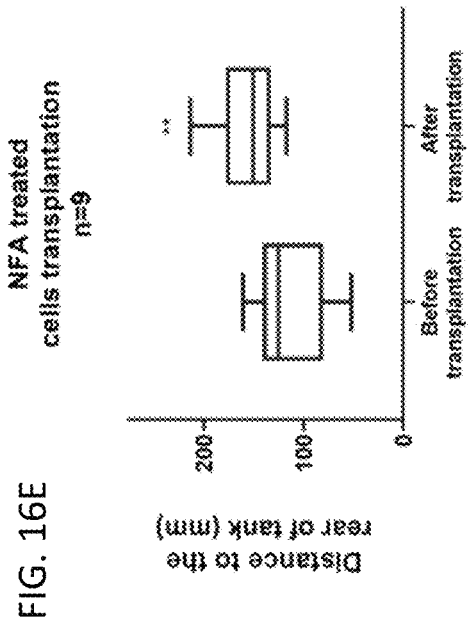
Figure 16E:
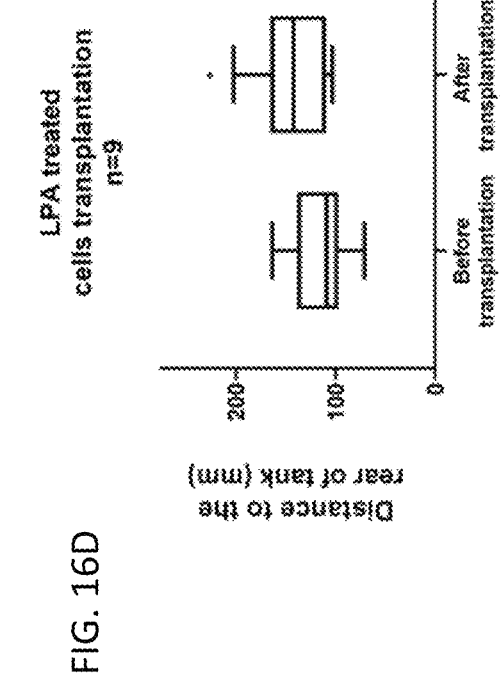

Transplantation of NFA-Treated or LPA-Treated ZeMPCs Improves Swimming Performance in Dystrophic Sapje-Like Zebrafish Finally, to assess the functionality of myogenic precursors exposed to NFA and/or LPA prior to muscle engraftment, the swimming performance of sapje-like fish was evaluated before and after transplantation. The sapje-like ($sap^{c/100}$) fish is a dystrophin mutant and an excellent genetic and phenotypic model of human Duchenne Muscular Dystrophy, demonstrating histological and physiological symptoms of profound muscle degeneration (Guyon et al., 2009) (FIG. 26). Recipient sapje-like fish were irradiated and injected with healthy ZeMPCs, exposed prior to transplant to NFA, LPA or vehicle alone, on both flanks at 3 dorsal points on each side—in the tail, beneath the dorsal fin, and in the trunk—with 25 cells per injection. Immediately prior to transplant, and again 7 days after transplant, muscle function was tested in a modified Blazka-type swim chamber, in which a flow rate of approximately 5.5 L/min was introduced to test swimming performance (FIG. 16A). Recipient fish that were transplanted with NFA-treated or LPA-treated cells, which reproducibly show a higher efficiency of myogenic engraftment (FIG. 12), performed significantly better in this test when compared to fish engrafted with vehicle-treated cells (FIG. 16B-E). Because only the treated cells were transplanted, after removal of the compounds, it was concluded from these studies that the swimming performance of these transplanted sapje-like fish was improved as a result of better engraftment by NFA-treated or LPA-treated ZeMPCs.

Discussion

Using the uniquely quantitative, rapid and integrated cross-species screening system described here, new regulators of vertebrate muscle cell engraftment were uncovered and a novel platform for discovery of pro-myogenic molecules that act directly on muscle precursor cells and target a stem cell-specific cellular function (in vivo engraftment) was established. Multiple studies, including this one, demonstrate the vastly superior capacity of the most primitive subset of muscle precursor cells to contribute productively to muscle repair in transplantation and regeneration assays, particularly in comparison to their differentiated daughters, despite the fact that the two types of cells often show equivalent proliferative capacity in ex vivo culture (Cerletti et al., 2012; Cerletti et al., 2008; Gurevich et al., 2016; Montarras et al., 2005; Sacco et al., 2008). Strategies that rely entirely on ex vivo screening for numeric increases in cell number (Billin et al., 2016; Nierobisz et al., 2013) could miss potent stem cell specific compounds whose effects are obscured by the presence of non-stem cells in these cultures. This might instead favor the identification of compounds that increase cell numbers overall but may not specifically expand or preserve the unique engraftment functions of the muscle stem cell compartment. On the other hand, the use of classical myogenic engraftment assays as a primary outcomes measure in chemical screening approaches has been eschewed by most in the research community due in large part to the prohibitive costs in terms of the time and resources it would require. Most studies to date that have identified single molecules capable of increasing the ex vivo yield of satellite cells or enhancing muscle regenerative potential have instead utilized candidate-based approaches, informed in some cases by genetic or transcriptional screening (Bernet et al., 2014; Kuang et al., 2007; Le Grand et al., 2009; Price et al., 2014; Tierney et al., 2014).

In this study, it was sought to overcome this barrier to direct screening on stem cell specific functions in muscle by developing a cross-species approach, first evaluating the myogenic effects of library compounds in a novel zebrafish transplantation system, and then further assessing "hits" in more standard mouse models. A significant advantage of this approach is the greater time efficiency and increased throughput afforded by use of the zebrafish system, which enables specification of myogenic progenitors within 2-3 days and readout of in vivo engraftment within a week. In contrast, analogous mouse and human systems require more than 1 month for each step (Xu et al., 2013). Furthermore, extensive data demonstrating the evolutionary conservation of vertebrate myogenesis and prior work documenting the strong predictive power of the zebrafish system to identify bioactive molecules that similarly regulate mammalian myogenesis (Xu et al., 2013), provided strong rationale for this cross-species approach. The specificity and rigor of this platform was further increased by incorporating highly sensitive limit dilution assays for quantitative assessment of engrafting cell frequencies within populations of compound-exposed cells. An unbiased assessment of all lipid mediators contained within a focused library of bioactive compounds was undertook, and by restricting compound exposure to ex vivo pre-transplantation treatment of myogenic progenitor cells, removing compounds by washing prior to transplant, any potential toxicity or indirect (bystander) effect of the compounds on the host environment was eliminated. These features resulted in a robust assay system for studying muscle engraftment.

Using this novel in vivo cross-systems strategy, 188 compounds were screened in zebrafish and the two top candidates—niflumic acid (NFA), an FDA-approved non-steroidal anti-inflammatory drug, and lysophosphatidic acid (LPA), a bioactive phospholipid, were selected for further testing in mice. Improved engraftment after pre-transplantation treatment with each of these lipid mediators in both zebrafish and mice was documented, and further identified overlapping cell physiological effects and transcriptional consequences of these two compounds. These observations reinforce the notion that this approach optimally leverages evolutionary similarities between vertebrates to enable more efficient drug identification.

LPA is a prominent member of the lysophospholipid (LP) family, an endogenous class of lipid mediators known to act through sets of specific G-protein-coupled receptors (GPCRs) named LPAR1-LPAR6 (Hecht et al., 1996). LPA may pass through the cell membrane (Stapleton et al., 2011) and may also be generated from membrane phospholipids (Budnik and Mukhopadhyay, 2002). Prior studies have implicated LPA in regulating intracellular calcium ion concentrations, consistent with the results presented here, as well as in the control of cell migration, adhesion, survival, development, and proliferation (Ishii et al., 2004; Sheng et al., 2015; Xu et al., 2008; Ye and Chun, 2010). In studies of cancer cells, LPA's effects on cell migration have been attributed to its stimulation of Rho activation and actin depolymerization via increases in intracellular calcium ion concentration (Ishii et al., 2004; Kim and Adelstein, 2011). In muscle cells, LPA also has been shown to stimulate the migration and proliferation of cultured myoblasts (Cencetti et al., 2014), with its effects mediated in part through sphingosine kinase and sphingosine-1-phosphate receptors; however, the impact of LPA on the regenerative activities of muscle satellite cells in vivo have not previously been assessed. The studies presented here reveal that LPA exposure significantly enhances the engraftment capacities of muscle progenitor cells from both zebrafish and mice, concomitant with increases in cytoplasmic calcium concentration and alterations of myogenic gene expression.

Like LPA, NFA exposure likewise enhanced the engraftment activities of muscle progenitors across species and induced similar calcium flux and transcriptional alterations. Unlike LPA, which is produced endogenously in fish and mice, NFA is a synthetic compound whose cellular receptor remains unknown. NFA is a member of the non-steroidal anti-inflammatory drug (NSAID) family and can inhibit both phospholipase A2 as well as cyclooxygenases such as COX-2. NFA is frequently used in the treatment of rheumatoid arthritis to reduce pain and suppress inflammation; however, its potential utility for augmenting the contributions of transplanted myogenic progenitors to regenerating muscle has not previously been assessed. Interestingly, prior studies testing the in vivo effects of NSAID administration on endogenous muscle repair have reported both pro-regenerative (Oh et al., 2016) and anti-regenerative (Ho et al., 2017) impact. This suggests differences in the specific actions of individual NSAIDs and/or pleiotropy of their action on different cell types in vivo. In this regard, the ex vivo exposure and transplantation strategy implemented here presents a distinct advantage, avoiding such complications by restricting compound exposure to only myogenic precursor cells and thereby revealing the particular effects of these molecules on stem cell-specific regenerative activities.

In these studies, both NFA and LPA were found to trigger rapid increases in intracellular calcium ion concentration within treated muscle progenitors, consistent with prior observations in other cell types (Liantonio et al., 2007; Xu et al., 2008). Notably, these effects of LPA and NFA were additive, potentially reflecting previously reported differences in the mechanisms by which they impact calcium flux. In particular, while NFA triggers increases in intracellular calcium by inducing the release of calcium ions from intracellular stores, increases of intracellular calcium seen with LPA treatment have been attributed to influx of calcium ions from extracellular sources (Poronnik et al., 1992; Rao et al., 2003). It is posited that exposure to NFA and LPA together enables mobilization of calcium from both intracellular and extracellular depots, resulting in an additive effect.

It was also found that LPA increases the expression of myoblast fusion regulators and effectors, including Ccl8 (Griffin et al., 2010) and Myomaker (also known as Mymk and Tmem8c) (Millay et al., 2013; Quinn et al., 2017). Such effects may promote the increased contribution of LPA-treated cells to the formation of multinucleated fibers in transplant recipients. Moreover, in addition to its effects promoting myogenic cell fusion, Ccl8 also has been implicated in promoting myogenic differentiation (Ge et al, 2013) and as a positive regulator of the release of sequestered calcium ions into the cytosol (Richardson et al., 2000). Thus, induction of Ccl8 by LPA may further enhance the calcium mobilizing and pro-myogenic activities of this compound.

As an ultimate test of the ability of compounds discovered in this screening system to stimulate productive contributions to regenerative myogenesis by transplanted muscle precursor cells, the impact on muscle function in dystrophic sapje-like fish of engraftment with NFA-treated or LPA-treated cells, simulating a clinical cell therapy scenario, was examined. Engraftment with either NFA-treated or LPA-treated muscle progenitors resulted in significant improvements in swimming performance of the recipient fish, in comparison to control fish receiving equivalent numbers of vehicle-treated ZeMPCs. Given the consistent observation that LPA and NFA treatment increases the engraftment efficiency of donor ZeMPCs, together with the fact that compound exposure was restricted to the pre-transplantation period, with careful washing to remove any residual compound prior to cell injection, it was concluded from these studies that the improvement in swimming performance reflects an improved engraftment efficiency, with no direct effect on the recipient muscle tissue. Such ex vivo chemical treatment approaches could be applied in clinical cell therapy approaches, as a strategy to boost the per cell regenerative output of ex vivo expanded or pluripotent cell derived human muscle progenitors.

In summary, this work establishes a novel screening platform for the discovery of pro-myogenic compounds that act specifically on muscle stem cells and target a muscle stem cell-specific function—myogenic engraftment after in vivo transplantation. Applying this platform to interrogate a relatively understudied class of bioactive molecules, lipid mediators, two—NFA and LPA—were discovered that enhanced the in vivo engraftment efficiency of both in vitro expanded embryo-derived zebrafish muscle cells and freshly isolated mouse muscle satellite cells. It was further showed that LPA and NFA also significantly increased intracellular calcium ion concentration in zebrafish muscle cells, C2C12 mouse muscle cells, and mouse satellite cells. It was discovered that the combination of these two lipids at low concentrations had an additive effect and increased muscle progenitor cell engraftment efficiency. Finally, the functionality of transplanted cells was evaluated and transplantation of NFA- and LPA-treated ZeMPCs was shown to improve zebrafish muscle function as measured by swimming performance, in comparison to vehicle-treated cells. This study indicates that pre-transplantation drug treatment can be an essential step toward improving muscle cell therapy approaches and rescuing muscle function through progenitor cell engraftment in muscular dystrophies.

Experimental Procedure

Culture and Myogenesis of Dissociated Zebrafish Blastomere Cells

Myogenic progenitor cells were generated in vitro from mylz2-GFP embryos using published protocols (Xu et al., 2013) with minor changes. mylz2-GFP transgenic line blastomere cells were dissociated and grown in a zESC medium composed of 70% LDF medium (50% Leibowitz's L-15 (Invitrogen), 35% DMEM (Invitrogen), and 15% Ham's F-12 (Invitrogen)), with 20% embryo extract and 10% FBS; these were supplemented with 2 ng/ml recombinant human FGF basic protein (Sigma-Aldrich), 15 mM sodium bicarbonate, 15 mM HEPES (Invitrogen),1% L-glutamine (Invitrogen), 10 nM sodium selenite (Sigma-Aldrich), 1% N2 (Invitrogen), 2% B27 (Invitrogen), and 0.1 mg/ml Primocin (Invivogen). Cells were cultured at 28° C. without $CO_2$ for 48 hours.

Chemical Treatments and Zebrafish In Vivo Screen

Lipids from the ICCB Known Bioactives Library (enzolifesciences.com/BML-2840/iccb-known-bioactives-library) were diluted at a 1:100 ratio in transplantation media (zESC medium without bFGF and FBS) and added to prewashed in vitro expanded muscle cells. NFA (Cayman and Santa Cruz Biotechnology) and LPA (Cayman and Santa Cruz Biotechnology) were used for the secondary confirmation screening experiments. Zebrafish cells were incubated with lipids for 4 hours at 28.5° C., followed by washing out the media and drugs, harvesting the cells, and splitting into 3 cell doses for transplantation. 4- to 8-month-old casper recipients received split-dose irradiation of 15 Gy each, either 2 days or 1 day before transplantation. For LDA screening, cells were transplanted into each side of 5 pre-irradiated casper recipient fish or 5 non-irradiated prkdc-mutant recipient zebrafish. At 7 dpt, the recipients were anaesthetized using a previously described method (Dang et al., 2016) and imaged using a fluorescent stereo microscope (Leica M165 FC). Successful engraftment was defined as the presence of GFP+ fibers. Variation in different experiments is caused by inherent variability in the in vitro ZeMPC derivation procedure, which results in differences in engrafting cell frequency across different derivation attempts. To mitigate the impact of such experimental variation on screening results, only LDA results for cells derived from the same cultures were compared. Comparison to a vehicle-treated experimental control was included in every transplantation experiment. Next, the chemical treated cell potency and vehicle-treated cell potency was measured using the Extreme Limiting Dilution Analysis (ELDA) software (Hu and Smyth, 2009). The ratio of the treated cell potency and vehicle-treated cell potency determine the engraftment efficiency fold increase value.

Zebrafish Tissue Sampling, Staining, and Imaging

Adult zebrafish recipients were euthanized at 7 dpt. The dissected body trunks were fixed in 4% paraformaldehyde, followed by cryoprotection with 30% sucrose solution at 4° C. overnight. Tissue specimens were embedded with Leica OTC tissue-freezing medium (Leica 14020108926) and rapidly frozen in liquid nitrogen, then sectioned with a cryostat at −25° C. (Leica CM1860). The sections were transferred to a room temperature Opaque-coated slide (VWR® Superfrost® Plus Micro Slide 48311-703), followed by air-drying overnight. Sections were demembranated, blocked, and stained with 0.5% Triton X-100, 3% BSA, and DAPI, respectively. The sections were protected by embedding in mounting medium (Vectashield H-1400) and covered with a coverslip. The mounted slides were stored at 4° C. in a light-protected condition to preserve the fluorescence before imaging. The images were acquired using Zeiss Axio Scan.Z1 and Zeiss 880 in the Harvard Center for Biological Imaging. The captured images were processed quantitatively with Zen, ImageJ, and MATLAB.

Fish Housing and Husbandry

All fish used in the experiment were housed in 3.5 L tanks with recirculating water and kept at 10 fish per liter. Water quality was kept at a constant 1250 µS, pH 7.5, and a water temperature of 28.5° C. Fish were fed Gemma Micro 500 at approximately 5% body weight per day and housed under a photoperiod of 14 hr-light, 10 hr-dark cycle.

Functional Assay Setup and Swimming Performance Measurement

Juvenile zebrafish from a sapje-like transgenic line were fin-clipped and genotyped to identify heterozygotes. A flow-through modified Blazka-type swim chamber was creating using a horizontal acrylic tank with dimensions of 350 mm 1×47 mm w×90 mm d. System water, equal in quality to recirculating water in housing tanks, was introduced into one side of the swim chamber at a flow rate of approximately 5.5 L min$^{-1}$. Water flow funneled through a honeycombed grid composed of 50 vinyl tubes (6.35 mm OD, 3.97 mm ID×50 mm 1). This created a laminar flow through the remaining 250 mm length of the swim chamber×50 mm deep×47 mm wide, delimiting fish to a swimming area of approximately 587.5 cubic cm=0.6 L. Another 1000-micron baffle was positioned downstream of the tunnel to prevent any fish from flowing out of the three drainage points located at the far end of the swim chamber. Adult sapje-like fish were netted out of their holding tanks and placed inside the already flowing swim chamber before and 7 days after transplantation. A high-definition Nikon D3100 digital camera was used to record individual fish's swimming performance, filmed at 30 frames per second for a total of 3 minutes. If a fish reached a point of fatigue where it could no longer maintain its position in the swim chamber, the fish was swept downstream onto the 1000-micron baffle located at the far end of the tank. A plastic transfer pipette was used to assist the fish off the baffle if it could not free itself and continue swimming. The raw digital file was then analyzed for movement within the swim area. The distance from the flow source was quantified using MATLAB (MathWorks).

Mouse Husbandry and Handling

FVB-Tg(CAG-luc,–GFP) mice (Stock 008450), Tg(CAG-EGFP) mice (Stock 003516), and FVB/NJ mice (Stock 001800) were obtained from the Jackson Laboratory. All mice were housed in the Animal Facility of Harvard University and all the experiments and protocols were performed in compliance with the institutional guidelines of Harvard University. These studies used adult (8-16 weeks of age) male mice.

Mouse Satellite Cell Isolation, Treatment, and Transplantation

Mouse satellite cells were isolated as previously described (Maesner et al., 2016; Sherwood et al., 2004; Xu et al., 2013). 25 µl (0.03 mg/ml) of cardiotoxin (CDTX) (Latoxan) was injected 24 h prior to transplantation into the TA muscle of recipient mice (FVB/NJ). Luc-GFP tagged satellite cells were isolated and plated on a collagen/laminin-coated plate and treated with NFA (10 µM), LPA (5 µM) or DMSO, as the vehicle control, in culture media for 4 hours at 37° C. The culture media contained 78% F10 (GIBCO), 20% horse serum (Atlanta Biologics), 1% penicillin-streptomycin (Invitrogen), 1% GlutaMAX (Invitrogen), and 5 ng/ml bFGF (Sigma). After 4 hours, cells were washed with DPBS, harvested, and counted, followed by transplantation of 5000 satellite cells intramuscularly into the CDTX pre-injured TA of FVB recipients.

Bioluminescence Imaging (BLI)

Mice were anesthetized with isoflurane and weighed. 150 mg/kg of luciferin (Goldbio) was administered by IP injection. BLI was acquired using IVIS Spectrum every 2 minutes, at F-stop=1.0 at 5 min after luciferin injection. The acquired images were analyzed and the highest captured radiance in the region of interest (ROI) was measured.

Mouse TA Sampling, Cryosectioning, Staining, and Imaging

The transplanted TAs were dissected and fixed in 4% paraformaldehyde, followed by cryoprotection with a 30% sucrose solution. Next, the TAs were washed with DPBS and frozen in pre-incubated isopentane in liquid nitrogen for 30 seconds followed by a 30-second incubation in liquid nitrogen. The frozen TA muscles were sectioned using a cryostat at −25° C. (Leica CM1850) at 10 μm thickness. The sections were stained with WGA (Thermo Fischer) and DAPI (Thermo Fischer) and embedded in mounting medium (Vectashield, vector laboratories). The images were acquired using Axio Scan.Z1 (Zeiss) and Zeiss 880 in the Harvard Center for Biological Imaging. The captured images were processed quantitatively with ZEN and ImageJ.

Calcium Imaging in ZeMPCs and C2C12 Cells

The ZeMPCs and C2C12 cells were incubated with Fura-2, AM (Thermo Fisher Sci F1225), a cell permeant fluorescent calcium ion indicator, for 45 minutes at 28.5° C. and 37° C., respectively, followed by imaging with Celldiscoverer7 Microscope (Zeiss). 20 seconds after imaging initiation the treatment was added to the cells and continued for a total of 2-3 minutes.

Calcium Imaging in Mouse Satellite Cells

Satellite cells were isolated from wild-type mice (FVB/NJ) and sorted into 384 well plates in culture media. The cells were incubated overnight at 37° C. The next day, the cells were incubated with Fluo-4 AM (Thermo Fisher Sci F14201), a fluorescent calcium ion indicator, for 45 minutes at 37° C., followed by imaging of the entire plate with the FDSS 7000 ex functional drug screening system (Hamamatsu) in the BCH assay development and screening facility.

RNA Sequencing

Isolated mouse muscle satellite cells and ZeMPCs were used to prepare RNA after in vitro chemical treatment. Total RNA was isolated by the micro RNeasy kit (QIAGEN). cDNA was prepared using SMART Seq v4 Ultra Low RNA-Seq kit for 48 reactions (Takara) and a Nextera kit was used for library construction. Sequencing data FASTQ files for samples were processed in tophat-cufflinks workflow in a Linux server operating system to output gene-level abundance estimates and statistical inference as gene-level raw counts. Those raw counts for samples were input into the cuffdiff for differential gene expression analysis. The assigned GEO accession number for the RNA sequencing data is GSE143801.

REFERENCES

Bernet, J. D., Doles, J. D., Hall, J. K., Kelly Tanaka, K., Carter, T. A., and Olwin, B. B. (2014). p38 MAPK signaling underlies a cell-autonomous loss of stem cell self-renewal in skeletal muscle of aged mice. Nature medicine 20, 265-271.

Berridge, M. J., Lipp, P., and Bootman, M. D. (2000). The versatility and universality of calcium signalling. Nature Reviews Molecular Cell Biology 1, 11.

Billin, A. N., Bantscheff, M., Drewes, G., Ghidelli-Disse, S., Holt, J. A., Kramer, H. F., McDougal, A. J., Smalley, T. L., Wells, C. I., Zuercher, W. J., et al. (2016). Discovery of Novel Small Molecules that Activate Satellite Cell Proliferation and Enhance Repair of Damaged Muscle. ACS Chemical Biology 11, 518-529.

Bischoff, R. (1975). Regeneration of single skeletal muscle fibers in vitro. The Anatomical record 182, 215-235.

Budnik, L. T., and Mukhopadhyay, A. K. (2002). Lysophosphatidic Acid and Its Role in Reproduction. Biology of Reproduction 66, 859-865.

Carlson, B. M. (1973). The regeneration of skeletal muscle. A review. The American journal of anatomy 137, 119-149.

Carlson, B. M., and Faulkner, J. A. (1996). The regeneration of noninnervated muscle grafts and marcaine-treated muscles in young and old rats. The journals of gerontology Series A, Biological sciences and medical sciences 51, B43-49.

Castiglioni, A., Hettmer, S., Lynes, M. D., Rao, T. N., Tchessalova, D., Sinha, I., Lee, B. T., Tseng, Y. H., and Wagers, A. J. (2014). Isolation of progenitors that exhibit myogenic/osteogenic bipotency in vitro by fluorescence-activated cell sorting from human fetal muscle. Stem cell reports 2, 92-106.

Cencetti, F., Bruno, G., Blescia, S., Bernacchioni, C., Bruni, P., and Donati, C. (2014). Lysophosphatidic acid stimulates cell migration of satellite cells. A role for the sphingosine kinase/sphingosine 1-phosphate axis. FEBS Journal 281, 4467-4478.

Cerletti, M., Jang, Y. C., Finley, L. W., Haigis, M. C., and Wagers, A. J. (2012). Short-term calorie restriction enhances skeletal muscle stem cell function. Cell stem cell 10, 515-519.

Cerletti, M., Jurga, S., Witczak, C. A., Hirshman, M. F., Shadrach, J. L., Goodyear, L. J., and Wagers, A. J. (2008). Highly Efficient, Functional Engraftment of Skeletal Muscle Stem Cells in Dystrophic Muscles. Cell 134, 37-47.

Collins, C. A., Olsen, I., Zammit, P. S., Heslop, L., Petrie, A., Partridge, T. A., and Morgan, J. E. (2005). Stem cell function, self-renewal, and behavioral heterogeneity of cells from the adult muscle satellite cell niche. Cell 122, 289-301.

Conboy, I. M., Conboy, M. J., Smythe, G. M., and Rando, T. A. (2003). Notch-mediated restoration of regenerative potential to aged muscle. Science (New York, NY) 302, 1575-1577.

Cox, G. A., Cole, N. M., Matsumura, K., Phelps, S. F., Hauschka, S. D., Campbell, K. P., Faulkner, J. A., and Chamberlain, J. S. (1993). Overexpression of dystrophin in transgenic mdx mice eliminates dystrophic symptoms without toxicity. Nature 364, 725-729.

Dang, M., Henderson, R. E., Garraway, L. A., and Zon, L. I. (2016). Long-term drug administration in the adult zebrafish using oral gavage for cancer preclinical studies. Dis Model Mech 9, 811-820.

Ervasti, J. M. (2007). Dystrophin, its interactions with other proteins, and implications for muscular dystrophy. Biochimica et Biophysica Acta (BBA)—Molecular Basis of Disease 1772, 108-117.

Fukada, S.-i., Higuchi, S., Segawa, M., Koda, K.-i., Yamamoto, Y., Tsujikawa, K., Kohama, Y., Uezumi, A., Imamura, M., Miyagoe-Suzuki, Y., et al. (2004). Purification and cell-surface marker characterization of quiescent satellite cells from murine skeletal muscle by a novel monoclonal antibody. Experimental Cell Research 296, 245-255.

Griffin, C. A., Apponi, L. H., Long, K. K., and Pavlath, G. K. (2010). Chemokine expression and control of muscle cell migration during myogenesis. J Cell Sci 123, 3052-3060.

Gurevich, D. B., Nguyen, P. D., Siegel, A. L., Ehrlich, O. V., Sonntag, C., Phan, J. M., Berger, S., Ratnayake, D., Hersey, L., Berger, J., et al. (2016). Asymmetric division of clonal muscle stem cells coordinates muscle regeneration in vivo. Science (New York, NY) 353, aad9969.

Guyon, J. R., Goswami, J., Jun, S. J., Thorne, M., Howell, M., Pusack, T., Kawahara, G., Steffen, L. S., Galdzicki, M., and Kunkel, L. M. (2009). Genetic isolation and characterization of a splicing mutant of zebrafish dystrophin. Human Molecular Genetics 18, 202-211.

Hecht, J. H., Weiner, J. A., Post, S. R., and Chun, J. (1996). Ventricular zone gene-1 (vzg-1) encodes a lysophosphatidic acid receptor expressed in neurogenic regions of the developing cerebral cortex. The Journal of cell biology 135, 1071-1083.

Ho, A. T. V., Palla, A. R., Blake, M. R., Yucel, N. D., Wang, Y. X., Magnusson, K. E. G., Holbrook, C. A., Kraft, P. E., Delp, S. L., and Blau, H. M. (2017). Prostaglandin E2 is essential for efficacious skeletal muscle stem-cell function, augmenting regeneration and strength. Proceedings of the National Academy of Sciences 114, 6675-6684.

Hu, Y., and Smyth, G. K. (2009). ELDA: Extreme limiting dilution analysis for comparing depleted and enriched populations in stem cell and other assays. Journal of Immunological Methods 347, 70-78.

Huxley, H. E. (1963). Electron microscope studies on the structure of natural and synthetic protein filaments from striated muscle. Journal of Molecular Biology 7, 281-IN230.

Ishii, I., Fukushima, N., Ye, X., and Chun, J. (2004). Lysophospholipid receptors: signaling and biology. Annual review of biochemistry 73, 321-354.

Ju, B., Chong, S. W., He, J., Wang, X., Xu, Y., Wan, H., Tong, Y., Yan, T., Korzh, V., and Gong, Z. (2003). Recapitulation of fast skeletal muscle development in zebrafish by transgenic expression of GFP under the mylz2 promoter. Dev Dyn 227, 14-26.

Judson, R. N., Quarta, M., Oudhoff, M. J., Soliman, H., Yi, L., Chang, C. K., Loi, G., Vander Werff, R., Cait, A., Hamer, M., et al. (2018). Inhibition of Methyltransferase Setd7 Allows the In Vitro Expansion of Myogenic Stem Cells with Improved Therapeutic Potential. Cell stem cell 22, 177-190.e177.

Kim, J. H., and Adelstein, R. S. (2011). LPA(1)-induced migration requires nonmuscle myosin II light chain phosphorylation in breast cancer cells. Journal of cellular physiology 226, 2881-2893.

Konigsberg, U. R., Lipton, B. H., and Konigsberg, I. R. (1975). The regenerative response of single mature muscle fibers isolated in vitro. Developmental biology 45, 260-275.

Kuang, S., Kuroda, K., Le Grand, F., and Rudnicki, M. A. (2007). Asymmetric Self-Renewal and Commitment of Satellite Stem Cells in Muscle. Cell 129, 999-1010.

Lahvic, J. L., Ammerman, M., Li, P., Blair, M. C., Stillman, E. R., Fast, E. M., Robertson, A. L., Christodoulou, C., Perlin, J. R., Yang, S., et al. (2018). Specific oxylipins enhance vertebrate hematopoiesis via the receptor GPR132. Proceedings of the National Academy of Sciences 115, 9252-9257.

Le Grand, F., Jones, A. E., Seale, V., Scime, A., and Rudnicki, M. A. (2009). Wnt7a activates the planar cell polarity pathway to drive the symmetric expansion of satellite stem cells. Cell stem cell 4, 535-547.

Li, P., Lahvic, J. L., Binder, V., Pugach, E. K., Riley, E. B., Tamplin, O. J., Panigrahy, D., Bowman, T. V., Barrett, F. G., Heffner, G. C., et al. (2015). Epoxyeicosatrienoic acids enhance embryonic haematopoiesis and adult marrow engraftment. Nature 523, 468-471.

Liantonio, A., Giannuzzi, V., Picollo, A., Babini, E., Pusch, M., and Conte Camerino, D. (2007). Niflumic acid inhibits chloride conductance of rat skeletal muscle by directly inhibiting the CLC-1 channel and by increasing intracellular calcium. British journal of pharmacology 150, 235-247.

Maesner, C. C., Almada, A. E., and Wagers, A. J. (2016). Established cell surface markers efficiently isolate highly overlapping populations of skeletal muscle satellite cells by fluorescence-activated cell sorting. Skeletal Muscle 6.

Mauro, A. (1961). Satellite cell of skeletal muscle fibers. The Journal of biophysical and biochemical cytology 9, 493-495.

Michalczyk, A., Budkowska, M., Dołęgowska, B., Chlubek, D., and Safranow, K. (2017). Lysophosphatidic acid plasma concentrations in healthy subjects: circadian rhythm and associations with demographic, anthropometric and biochemical parameters. Lipids Health Dis 16, 140-140.

Millay, D. P., O'Rourke, J. R., Sutherland, L. B., Bezprozvannaya, S., Shelton, J. M., Bassel-Duby, R., and Olson, E. N. (2013). Myomaker is a membrane activator of myoblast fusion and muscle formation. Nature 499, 301-305.

Montarras, D., Morgan, J., Collins, C., Relaix, F., Zaffran, S., Cumano, A., Partridge, T., and Buckingham, M. (2005). Direct isolation of satellite cells for skeletal muscle regeneration. Science (New York, NY) 309, 2064-2067.

Moore, J. C., Tang, Q., Yordan, N. T., Moore, F. E., Garcia, E. G., Lobbardi, R., Ramakrishnan, A., Marvin, D. L., Anselmo, A., Sadreyev, R. I., et al. (2016). Single-cell imaging of normal and malignant cell engraftment into optically clear prkdc-null SCID zebrafish. J Exp Med 213, 2575-2589.

Nierobisz, L. S., Cheatham, B., Buehrer, B. M., and Sexton, J. Z. (2013). High-content screening of human primary muscle satellite cells for new therapies for muscular atrophy/dystrophy. Current chemical genomics and translational medicine 7, 21-29.

Oh, J., Sinha, I., Tan, K. Y., Rosner, B., Dreyfuss, J. M., Gjata, O., Tran, P., Shoelson, S. E., and Wagers, A. J. (2016). Age-associated NF-kappaB signaling in myofibers alters the satellite cell niche and re-strains muscle stem cell function. Aging 8, 2871-2896.

Okazaki, K., and Holtzer, H. (1966). Myogenesis: fusion, myosin synthesis, and the mitotic cycle. Proceedings of the National Academy of Sciences of the United States of America 56, 1484-1490.

Partridge, T. A., Grounds, M., and Sloper, J. C. (1978). Evidence of fusion between host and donor myoblasts in skeletal muscle grafts. Nature 273, 306-308.

Poronnik, P., Ward, M. C., and Cook, D. I. (1992). Intracellular Ca2+ release by flufenamic acid and other blockers of the non-selective cation channel. FEBS letters 296, 245-248.

Price, F. D., von Maltzahn, J., Bentzinger, C. F., Dumont, N. A., Yin, H., Chang, N. C., Wilson, D. H., Frenette, J., and Rudnicki, M. A. (2014). Inhibition of JAK-STAT signaling stimulates adult satellite cell function. Nature medicine 20, 1174-1181.

Quinn, M. E., Goh, Q., Kurosaka, M., Gamage, D. G., Petrany, M. J., Prasad, V., and Millay, D. P. (2017). Myomerger induces fusion of non-fusogenic cells and is required for skeletal muscle development. Nature communications 8, 15665.

Rao, T. S., Lariosa-Willingham, K. D., Lin, F. F., Palfreyman, E. L., Yu, N., Chun, J., and Webb, M. (2003). Pharmacological characterization of lysophospholipid receptor signal transduction pathways in rat cerebrocortical astrocytes. Brain research 990, 182-194.

Richardson, R. M., Pridgen, B. C., Haribabu, B., and Snyderman, R. (2000). Regulation of the human chemokine receptor CCR1. Cross-regulation by CXCR1 and CXCR2. The Journal of biological chemistry 275, 9201-9208.

Sacco, A., Doyonnas, R., Kraft, P., Vitorovic, S., and Blau, H. M. (2008). Self-renewal and expansion of single transplanted muscle stem cells. Nature 456, 502-506.

Sheng, X., Yung, Y. C., Chen, A., and Chun, J. (2015). Lysophosphatidic acid signalling in development. Development (Cambridge, England) 142, 1390-1395.

Sherwood, R. I., Christensen, J. L., Conboy, I. M., Conboy, M. J., Rando, T. A., Weissman, I. L., and Wagers, A. J. (2004). Isolation of Adult Mouse Myogenic Progenitors: Functional Heterogeneity of Cells within and Engrafting Skeletal Muscle. Cell 119, 543-554.

Sinha, M., Jang, Y. C., Oh, J., Khong, D., Wu, E. Y., Manohar, R., Miller, C., Regalado, S. G., Loffredo, F. S., Pancoast, J. R., et al. (2014). Restoring systemic GDF11 levels reverses age-related dysfunction in mouse skeletal muscle. Science (New York, NY) 344, 649-652.

Stapleton, C. M., Mashek, D. G., Wang, S., Nagle, C. A., Cline, G. W., Thuillier, P., Leesnitzer, L. M., Li, L. O., Stimmel, J. B., Shulman, G. I., et al. (2011). Lysophosphatidic Acid Activates Peroxisome Proliferator Activated Receptor-γ in CHO Cells That Over-Express Glycerol 3-Phosphate Acyltransferase-1. PLOS ONE 6, e18932.

Tabebordbar, M., Wang, E. T., and Wagers, A. J. (2013). Skeletal Muscle Degenerative Diseases and Strategies for Therapeutic Muscle Repair. In Annu Rev Pathol Mech Dis, pp. 441-475.

Tanaka, K. K., Hall, J. K., Troy, A. A., Cornelison, D. D., Majka, S. M., and Olwin, B. B. (2009). Syndecan-4-expressing muscle progenitor cells in the SP engraft as satellite cells during muscle regeneration. Cell stem cell 4, 217-225.

Tierney, M. T., Aydogdu, T., Sala, D., Malecova, B., Gatto, S., Puri, P. L., Latella, L., and Sacco, A. (2014). STAT3 signaling controls satellite cell expansion and skeletal muscle repair. Nature medicine 20, 1182-1186.

Xu, C., Tabebordbar, M., Iovino, S., Ciarlo, C., Liu, J., Castiglioni, A., Price, E., Liu, M., Barton, E. R., Kahn, C. R., et al. (2013). A zebrafish embryo culture system defines factors that promote vertebrate myogenesis across species. Cell 155, 909-921.

Xu, Y.-J., Tappia, P. S., Goyal, R. K., and Dhalla, N. S. (2008). Mechanisms of the lysophosphatidic acid-induced increase in [Ca(2+)](i) in skeletal muscle cells. Journal of cellular and molecular medicine 12, 942-954.

Ye, X., and Chun, J. (2010). Lysophosphatidic acid (LPA) signaling in vertebrate reproduction. Trends in endocrinology and metabolism: TEM 21, 17-24.

Yin, H., Price, F., and Rudnicki, M. A. (2013). Satellite Cells and the Muscle Stem Cell Niche. Physiological Reviews 93, 23-67.

What is claimed is:

1. A composition comprising myogenic progenitor cells and one or more agents that enhances engraftment of the myogenic progenitor cells into muscle tissue, wherein the agent is selected from a compound that increases intracellular $Ca^{2+}$ levels in myogenic progenitor cells, meclofenamic acid (MFA) at a concentration of about 1-50 uM, lysophosphatidic acid (LPA) at a concentration of about 0.1-10 uM, and niflumic acid (NFA) at a concentration of about 0.1 to 150 uM.

2. The composition of claim 1, wherein the one or more agents comprise NFA and LPA.

3. The composition of claim 1, wherein the myogenic progenitor cells are human myogenic progenitor cells.

* * * * *